(12) United States Patent
Van Gelder et al.

(10) Patent No.: US 7,795,255 B2
(45) Date of Patent: Sep. 14, 2010

(54) RIGIDIFIED COMPOUNDS FOR MODULATING HEPARANASE ACTIVITY

(75) Inventors: Joel M. Van Gelder, Jerusalem (IL); Joseph Y. Klein, Haifa (IL); Yochai Basel, Rechovot (IL); Anat Reizelman, Rechovot (IL); Susanna Tchilibon, Jerusalem (IL); Orly Mouallem, Rechovot (IL)

(73) Assignee: InSight Biopharmaceuticals Ltd., Rehovot (IL)

( * ) Notice: Subject to any disclaimer, the term of this patent is extended or adjusted under 35 U.S.C. 154(b) by 162 days.

(21) Appl. No.: 11/794,764

(22) PCT Filed: Jan. 5, 2006

(86) PCT No.: PCT/IL2006/000023

§ 371 (c)(1),
(2), (4) Date: Jul. 5, 2007

(87) PCT Pub. No.: WO2006/072953

PCT Pub. Date: Jul. 13, 2006

(65) Prior Publication Data

US 2008/0039456 A1    Feb. 14, 2008

Related U.S. Application Data

(60) Provisional application No. 60/681,463, filed on May 17, 2005, provisional application No. 60/641,444, filed on Jan. 6, 2005.

(51) Int. Cl.
| | | |
|---|---|---|
| A61K 31/5377 | (2006.01) |
| A61K 31/53 | (2006.01) |
| A61K 31/496 | (2006.01) |
| A61K 31/41 | (2006.01) |
| A61K 31/4188 | (2006.01) |
| C07D 413/14 | (2006.01) |
| C07D 253/08 | (2006.01) |
| C07D 403/14 | (2006.01) |
| C07D 257/04 | (2006.01) |
| C07D 491/147 | (2006.01) |

(52) U.S. Cl. .............. 514/233.2; 514/241; 514/254.06; 514/382; 514/387; 544/139; 544/220; 544/370; 548/250; 548/302.4

(58) Field of Classification Search .............. 514/233.2, 514/241, 243, 293, 367, 373, 387, 254.06; 544/139, 184, 220, 370; 546/83; 548/153, 548/208, 302.4
See application file for complete search history.

(56) References Cited

OTHER PUBLICATIONS

Carter et al., Photochemically enhanced binding of small molecules to the tumor necrosis factor receptor-1 inhibits the binding of TNF-alpha, Oct. 9, 2001, PNAS, vol. 98, No. 21, pp. 11879-11884.*
Patani et al., Bioisosterism: A Rational Approach in Drug Design, 1996, Chem. Rev., 96, 3147-3176.*
Joel R. Huff, 1991, HIV Protease: A Novel Chemotherapetic Target for AIDS, Journal of Medicinal Chemistry, vol. 34, No. 8, pp. 2305-2314.*
Golub et al., Molecular Classification of Cancer: Class Discovery and Class Prediction by Gene Expression Monitoring, 1999, Science, vol. 286, pp. 531-537.*
Lala et al., Role of nitric oxide in tumor progression: Lessons from experimental tumors, 1998, Cancer and Metatasis Reviews, 17, 91-106.*
Gossauer et al. "Syntheses of Bile Pigments. Part 16. Synthesis of A Vinyl-Substituted 2,3-Dihydrobilinedione: Possible Role of this New Class of Bile Pigments in Phycobilin Biosynthesis", Helvetica Chimica Acta, 72(3): 518-529, 1989. Esp. p. 518-522.

* cited by examiner

Primary Examiner—Kamal A Saeed
Assistant Examiner—Kristin Bianchi

(57) ABSTRACT

Disclosed are novel rigidified compounds having a rhodanine-like residue and at least one aryl or heteroaryl residue linked to the rhodanine-like residue, whereby a core structure of these compounds, as defined in the specification, is characterized as having one or zero free-to-rotate bonds. Also disclosed are pharmaceutical compositions containing these rigidified compounds and uses thereof for modulating the activity of heparanase and hence in the treatment of heparanase-associated diseases and disorders, and uses thereof for modulating the activity of heparin-binding proteins and hence in the treatment of heparin-binding proteins-associated diseases and disorders as well as in the treatment of medical conditions that are at least partially treatable by rhodanine or a rhodanine analog.

27 Claims, No Drawings

RIGIDIFIED COMPOUNDS FOR MODULATING HEPARANASE ACTIVITY

RELATED APPLICATIONS

This Application is a National Phase of PCT Patent Application No. PCT/IL2006/000023 having International Filing Date of Jan. 5, 2006, which claims the benefit of U.S. Provisional Patent Application Nos. 60/681,463 filed on May 17, 2005; and 60/641,444 filed on Jan. 6, 2005. The contents of the above Applications are all incorporated herein by reference.

FIELD AND BACKGROUND OF THE INVENTION

The present invention relates to novel, rigidified compounds and uses thereof and, more particularly, to uses thereof for modulating the activity of heparanase and hence in the treatment of heparanase-associated diseases and disorders, to uses thereof for modulating the activity of heparin-binding proteins and hence in the treatment of heparin-binding proteins-associated diseases and disorders as well as to uses thereof in the treatment of medical conditions that are treatable by rhodanine or a rhodanine analog.

Proteoglycans (PGs):

Proteoglycans (previously named mucopolysaccharides) are remarkably complex molecules and are found in every tissue of the body. They are associated with each other and also with the other major structural components such as collagen and elastin. Some PGs interact with certain adhesive proteins, such as fibronectin and laminin. The long extended nature of the polysaccharide chains of PGs, the glycosaminoglycans (GAGs), and their ability to gel, allow relatively free diffusion of small molecules, but restrict the passage of large macromolecules. Because of their extended structures and the huge macromolecular aggregates they often form, they occupy a large volume of the extracellular matrix relative to proteins (Murry R K and Keeley F W; Biochemistry, Ch. 57. pp. 667-85).

Heparin Sulfate Proteoglycans (HSPGs):

HSPGs are acidic polysaccharide-protein conjugates associated with cell membranes and extracellular matrices. HSPGs bind avidly to a variety of biologic effector molecules, including extracellular matrix components, growth factor, growth factor binding proteins, cytokines, cell adhesion molecules, proteins of lipid metabolism, degradative enzymes, and protease inhibitors. Owing to these interactions, HSPGs play a dynamic role in biology; in fact most functions of the proteoglycans are attributable to the heparan sulfate (HS) chains, contributing to cell-cell interactions and cell growth and differentiation in a number of systems. HS maintains tissue integrity and endothelial cell function. It selves as an adhesion molecule and presents adhesion-inducing cytokines (especially chemokines), facilitating localization and activation of leukocytes. HS modulates the activation and the action of enzymes secreted by inflammatory cells. The functions of HS changes during the course of the immune response are due to changes in the metabolism of HS and to the differential expression of and competition between HS-binding molecules. (Selvan R S et al; Ann. NY Acad. Sci. 1996, 797: 127-39).

HSPGs are also prominent components of blood vessels (Wight T N et al; Arteriosclerosis, 1989, 9: 1-20). In large vessels HSPGs are concentrated mostly in the intima and inner media, whereas in capillaries HSPGs are found mainly in the subendothelial basement membrane, where they support proliferating and migrating endothelial cells and stabilize the structure of the capillary wall. The ability of HSPGs to interact with extracellular matrix (ECM) macromolecules such as collagen, laminin and fibronectin, and with different attachment sites on plasma membranes suggests a key role for this proteoglycan in the self-assembly and insolubility of ECM components, as well as in cell adhesion and locomotion.

Heparanase—A GAGs Degrading Enzyme:

Degradation of GAGs is carried out by a battery of lysosomal hydrolases. One important enzyme involved in the catabolism of certain GAGs is heparanase. It is an endo-β-glucuronidase that cleaves heparan sulfate at specific inter-chain sites.

The enzymatic degradation of glycosaminoglycans is reviewed By Ernst et al. (Critical Reviews in Biochemistry and Molecular Biology, 30(5):387-444 (1995). The common feature of GAGs structure is repeated disaccharide units consisting of a uronic acid and hexosamine. Various GAGs differ in the composition of the disaccharide units and in type and level of modifications, such as C5-epimerization and N or O-sulfation. Sulfated GAGs include heparin, heparan sulphate, chondroitin sulphate, dermatan sulphate and keratan sulphate. Heparan sulphate and heparin are composed of repeated units of glucosamine and glucuronic/iduronic acid, which undergo modifications such as C5-epimerization, N-sulfation and O-sulfation. Heparin is characterized by a higher level of modifications than heparan sulphate.

GAGs can be depolymerized enzymatically either by eliminative cleavage with lyases (EC 4.2.2.-) or by hydrolytic cleavage with hydrolases (EC 3.2.1.-). Often, these enzymes are specific for residues in the polysaccharide chain with certain modifications. GAGs degrading lyases are mainly of bacterial origin. In the eliminative cleavage, C5 hydrogen of uronic acid is abstracted, forming an unsaturated C4-5 bond, whereas in the hydrolytic mechanism a proton is donated to the glycosidic oxygen and creating an O5 oxonium ion followed by water addition which neutralizes the oxonium ion and saturates all carbons (Linhardt et al. 1986, Appl. Biochem. Biotech. 12:135-75). The lyases can only cleave linkages on the non-reducing side of the of uronic acids, as the carboxylic group of uronic acid participates in the reaction. The hydrolases, on the other hand, can be specific for either of the two bonds in the repeating disaccharides. In pages 414 and 424 of the review, tables 8 and 14, Ernst et al. list the known GAG degrading enzymes. These tables describe substrate specificity, cleavage mechanism, cleavage linkage, product length and mode of action (endo/exolytic). Heparanase is defined as a GAG hydrolase which cleaves heparin and heparan sulphate at the β1,4 linkage between glucuronic acid and glucosamine. Heparanase is an endolytic enzyme and the average product length is 8-12 saccharides. The other known heparin/heparan sulphate degrading enzymes are beta-glucuronidase, alpha-L iduronidase and alpha-N acetylglucosaminidase, which are exolytic enzymes, each one cleaves a specific linkage within the polysaccharide chain and generate disaccharides. In table 8 the authors list two heparanases; platelet heparanase and tumor heparanase, which share the same substrate and mechanism of action. These two were later on found to be identical at the molecular level (Freeman et al. Biochem J. (1999) 342, 361-268, Vlodavsky et al. Nat. Med. 5(7):793-802, 1999, Hullet et al. Nat. Med. 5(7):803-809, 1999).

Heparin and heparan sulphate fragments generated via heparanase catalyzed hydrolysis are inherently characterized by saturated non-reducing ends, derivatives of N-acetyl-glucosamine. The reducing sugar of heparin or heparan sulphate fragments generated by heparanase hydrolysis contains a hydroxyl group at carbon 4 and it is therefore UV inactive at 232 nm.

Interaction of T and B lymphocytes, platelets, granulocytes, macrophages and mast cells with the subendothelial extracellular matrix (ECM) is associated with degradation of heparan sulphate by heparanase activity. The enzyme is released from intracellular compartments (e.g., lysosomes, specific granules) in response to various activation signals (e.g., thrombin, calcium ionophore, immune complexes, antigens and mitogens), suggesting its regulated involvement in inflammation and cellular immunity. (Vlodavsky I et al; Invasion Metas. 1992; 12(2): 112-27). In contrast, various tumor cells appear to express and secrete heparanase in a constitutive manner in correlation with their metastatic potential. (Nakajima M et al; J. Cell. Biochem. 1988 February; 36(2): 157-67). Important processes in the tissue invasion by leukocytes include their adhesion to the luminal surface of the vascular endothelium, their passage through the vascular endothelial cell layer and the subsequent degradation of the underlying basal lamina and extracellular matrix with a battery of secreted and/or cell surface protease and glycosidase activities. Cleavage of HS by heparanase may therefore result in disassembly of the subendothelial ECM and hence may play a decisive role in extravasation of normal and malignant blood-borne cells (Vlodavsky I et al; Inv. Metast. 1992, 12: 112-27, Vlodavsky I et al; Inv. Metast. 1995, 14: 290-302).

It has been previously demonstrated that heparanase may not only function in cell migration and invasion, but may also elicit an indirect neovascular response (Vlodavsky I et al; Trends Biochem. Sci. 1991, 16: 268-71). The ECM HSPGs provide a natural storage depot for β-FGF. Heparanase mediated release of active β-FGF from its storage within ECM may therefore provide a novel mechanism for induction of neovascularization in normal and pathological situations (Vlodavsky I et al; Cell. Molec. Aspects. 1993, Acad. Press. Inc. pp. 327-343, Thunberg L et al; FEBS Lett. 1980, 117: 203-6). Degradation of heparan sulphate by heparanase results in the release of other heparin-binding growth factors, as well as enzymes and plasma proteins that are sequestered by heparan sulphate in basement membranes, extracellular matrices and cell surfaces. (Selvan R S et al; Ann. NY Acad. Sci. 1996, 797: 127-39).

Expression of Heparanase DNA in Animal Cells:

Stably transfected CHO cells express the human heparanase gene products in a constitutive and stable manner. Several CHO cellular clones are particularly productive in expressing heparanase, as determined by protein blot analysis and by activity assays. Although the heparanase DNA encodes for a large 543 amino acids protein (expected molecular weight about 65 kDa, SEQ ID NO: 8) the results clearly demonstrate the existence of three proteins, one of about 60 kDa (H60, SEQ ID NO: 34), another of about 45 kDa (H45, SEQ ID NO: 33) and yet another one of about 8 kDa (H8, SEQ ID NO: 35). It was found that active heparanase is a mature processed form with an apparent molecular weight of 53 kDa (H53), proteolytically cleaved from the latent heparanase precursor of about 60 kDa. This proteolytic cleavage occurs at two cleavage sites $Glu^{109}$-$Ser^{110}$ (SEQ ID NO: 1) and $Gln^{157}$-$Lys^{158}$ (SEQ ID NO: 2), yielding a 8 kDa polypeptide at the N-terminus, a 45 kDa polypeptide at the C-terminus and a 6 kDa linker polypeptide (H6, SEQ ID NO: 36) that is released due to the cleavage. The formation of the heterodimer between the 8 and 45 kDa subunits is essential for heparanase enzymatic activity (M B Fairbanks et al. J. Biol. Chem. 274, 29587, 1999).

Further details pertaining to heparanase, heparanase gene and their uses can be found in, for example, PCT/US99/09256; PCT/US98/17954; PCT/US99/09255; PCT/US99/25451; PCT/IL00/00358; PCT/US99/15643; PCT/US00/03542; PCT/US99/06189; PCT/US00/03353; PCT/US00/03542; PCT/IL01/00830; PCT/IL01/00950' PCT/IL01/00864; PCT/IL01/01169 and PCT/IL02/00362; and in U.S. Pat. Nos. 6,242,238; 5,968,822; 6,153,187; 6,177,545; and 6,190,875, the contents of all of which are hereby incorporated by reference.

Heparanase Activation:

Heparanase maturation involves the removal of the signal peptide, transforming the 65 kDa pre-pro-heparanase into a 60 kDa pro-heparanase (also referred to herein as latent heparanase or mature heparanase). The 60 kDa latent/mature heparanase is activated into an active heparanase as follows: The 60 kDa latent/mature heparanase is proteolytically cleaved twice into a 45 kDa major subunit, a 8 kDa small subunit and a 6 kDa linker that links the 45 kDa major subunit and the 8 kDa small subunit in the latent enzyme. The 45 kDa major subunit and the 8 kDa small subunit hetero-complex to form the 53 kDa active form of heparanase.

The nature of the protease(s) responsible for activating heparanase is yet unknown.

It will, nevertheless, be appreciated that by modulating the activity of these proteases one can modulate the rate of heparanase activation, hence the rate of heparanase activity and hence the rate of biological processes which depend on heparanase activity.

There is thus a widely recognized need for and it would be highly advantageous to have compounds which can efficiently modulate heparanase activation, by e.g., inhibiting or increasing heparanase activation.

Rhodanine-Based Compounds as Heparanase Inhibitors:

In U.S. patent application Ser. No. 10/916,598, filed Aug. 12, 2004, by the present assignee, which is incorporated by reference as if fully set forth herein, it is taught that heparin plays a critical role in the activation of pro-heparanase and that use of, or interference with, any one of the components or processes involved in heparanase activation may be enough to modulate biological processes, which are governed by heparanase activity. A cell-based assay, which allows the identification of numerous inhibitors of heparanase activation is further taught in this patent application. Based on the above, a comprehensive list of inhibitors, which may be used for inhibiting heparanase activation, was disclosed.

U.S. patent application Ser. No. 10/916,598 particularly teaches several families of compounds that are capable of interfering with heparanase activity. These include, for example, a family of rhodanine analogs, a family of planar aromatic molecules and a family of peptidomimetic molecules.

Rhodanine is a five-membered heterocyclic compound having the following structure:

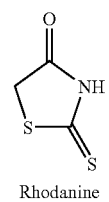

Rhodanine

U.S. patent application Ser. No. 10/916,598 also teaches that inhibition of heparin binding to pro-heparanase may be effected by a heparin-binding agent (or heparan-sulphate binding agent) or by a pro-heparanase binding agent.

Preferred pro-heparanase binding agents, according to the teachings of U.S. patent application Ser. No. 10/916,598, can be collectively represented by the general formula:

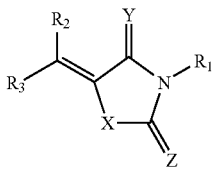

wherein:

X is O, S, $NR_4$ or $NR_5$—C(=D);

Y, Z and D are each independently O, S or $NR_4$;

$R_1$ is selected from the group consisting of hydrogen, alkyl, cycloalkyl, alkenyl, allyl, aryl, heteroaryl, heteroalicyclic and an acid-containing moiety; and at least one of $R_2$ and $R_3$ being a substituted or unsubstituted aryl or heteroaryl, and further wherein:

$R_4$ and $R_5$ are each independently selected from the group consisting of hydrogen, alkyl, cycloalkyl and a aryl.

Particularly promising pro-heparanase binding agents, according to the teachings of U.S. patent application Ser. No. 10/916,598, were found to be rhodanine derivatives having a rhodanine skeleton, such that in the general formula above X is S; Y is O; and Z is S.

It was found, however, that derivatives of rhodanine analogs also act as potent pro-heparanase binding agents. Representative example of rhodanine analogs include, without limitation, compounds having the general formula above, in which X is S; Y is O; and Z is O, and in which X is $NR_5$—C=D; Y is O; Z is O or S; and D is O or S (2-thio/oxo-dihydro-pyrimidine-4,6-dione).

It was further found that another component which may affect the binding potency of these compounds is the substituent $R_1$. Thus, it was found that derivatives of rhodanine or rhodanine analogs in which $R_1$ in the general Formula above is an acid-containing moiety, or a heteroaryl such as, for example, terahydrothiophenyl-1,1-dioxide and 1,5-dimethyl-2-phenyl-1,2-dihydro-3-one-pyrazolyl. Preferred acid-containing moieties were found to include aliphatic carboxylic acid residues having a chain of 2-6 carbon atoms.

More particular promising pro-heparanase binding agents, according to the teachings of U.S. patent application Ser. No. 10/916,598, were found to be derivatives of rhodanine or rhodanine analogs, as shown in the general Formula above, which are substituted by a methylidene group, which in turn, is substituted by a heteroaryl such as furan. The furan is preferably substituted by an aryl group such as a substituted phenyl. Suitable substituents of the phenyl ring include, for example, hydrogen, alkyl, hydroxy, thiohydroxy, alkoxy, thioalkoxy, halo, nitro, trihaloalkyl, C-carboxy, O-carboxy, C-amido, N-amido, S-sulfonamido and N-sulfonamido, or, alternatively, at least two substituents form a five- or six-membered cyclic, heteroalicyclic, aromatic or heteroaromatic ring. Preferred substituents are hydrogen, halo (e.g., chloro) and/or nitro.

Furthermore, the nature of the substituents on the phenyl ring was found to affect the binding potency of these agents. Hence, the substituents at the ortho positions with respect to the furan are preferably hydrogen, and/or an electron donating-group such as alkyl, cycloalkyl, hydroxy, alkoxy, thiohydroxy, thioalkoxy, aryloxy and thioaryloxy, whereby the substituent at the meta and para positions are preferably hydrogen and/or an electron-withdrawing group such as halo, nitro, trihaloalkyl and C-carboxy. The C-carboxy substituent is preferably a carboxylic acid group.

The most promising agents, according to the teachings of U.S. patent application Ser. No. 10/916,598, can therefore be collectively represented by the following general Formula:

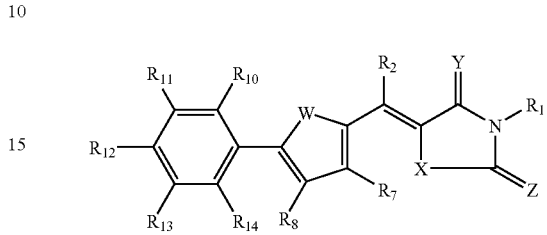

wherein X, Y, Z and $R_1$ are as described above, W is O or S, defining a furan ring or a thiophene ring; $R_2$, $R_7$ and $R_8$ are each independently hydrogen, alkyl, cycloalkyl, aryl and heteroaryl, preferably hydrogen; and $R_{10}$ to $R_{14}$ are each independently a substituent as described hereinabove.

Some of the compounds described above as pro-heparanase binding agents were found to have a dual activity, such that in addition to inhibiting pro-heparanase activation, they inhibit heparanase activity. Preferred compounds in this category are those bearing a carboxylic acid group, either as the $R_1$ substituent or as one of the $R_{10}$-$R_{14}$ substituents.

The most preferred compounds according to the teachings of U.S. patent application Ser. No. 10/916,598, can be described by the general formula:

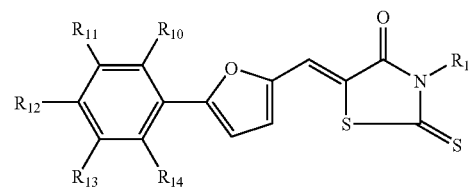

wherein:

$R_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic and an acid-containing moiety having the general formula:

—$(CH_2)n$-$CH(R_6)$-$Q_1$(OH), whereas, n is integer that equals 0-20;

$R_6$ is selected from the group consisting of hydrogen, alkyl and $Q_2$(OH); and $Q_1$ and $Q_2$ are each independently selected from the group consisting of C=O and S(=O)$_2$; and $R_{10}$-$R_{14}$ are each independently selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxy, O-carboxy, oxo, C-amido, N-amido, S-sulfonamido and N-sulfonamido, whereby either $R_1$ is the acid-containing moiety or at least one of the $R_{10}$-$R_{14}$ is C-carboxy.

Alternatively, both $R_1$ and one or more of the substituents $R_{10}$-$R_{14}$ include an acidic moiety.

Although the above-described compounds were found effective in modulating heparanase activity and heparin-binding proteins activity, the present inventors have envisioned that structurally-related compounds which are characterized by a lower number of free-to-rotate bonds and hence by a rigidified structure could exhibit higher affinity to the target and thus would exhibit improved performance.

Rhodanine-based compounds are also known as efficient agents for treating a wide scope of other medical conditions. These include, for example, CNS disorders such as Alzheimer's disease and schizophrenia, atherosclerosis, autoimmune diseases, bacterial infections such as anthrax, cholera, and tuberculosis, blood coagulation, bone disorders, cancer, cardiovascular diseases, diabetes, fungal infections, gastrointestinal disorders, hair loss, hypercholesterolemia, inflammation, pain, and viral diseases and infections such as hepatitis C, herpes, HIV, and smallpox.

The wide scope of medical conditions that is treatable by rhodanine-based compounds is indicative of the beneficial merits of such compounds as a concept for drug development in general. However, such a wide scope of activities may also imply that rhodanine-based compounds might exert toxic and other adverse effects due to lack of specificity.

The present inventors have therefore further envisioned that rhodanine-based compounds which are characterized by a lower number of free-to-rotate bonds and hence by a rigidified structure would exhibit higher specificity to the targeted organ or system and could further be efficiently utilized in the treatment of these conditions.

While some rhodamine-based compounds that have a rigidified structure have been reported, the biological activity of these compounds has been questionable. Thus, compounds having a N-(3-morpholino)propyl rhodanine analog residue being covalently attached to a 5-(3-methoxyphenyl)thiophene group and a 5-(3-nitrophenyl)thiophene group have been disclosed by Carter et al. (in Proc. Natl. Acad. Sci., 98, 11879, 2001). These compounds, along with other, non-rigid rhodanine-based compounds, were tested for their binding to tumor necrosis factor-alpha (TNF-alpha), and were found active only when exposed to light. 5-Arylidene-2-thioxodihydropyrimidine-4,6(1H,5H)-diones and 3-thioxo-2,3-dihydro-1H-imidazolo[1,5-a]indol-1-ones were also reported to act as light-dependent TNF-alpha antagonists (Voss et al., Bioorg. Med. Chem. Lett., 13, 533-538, 2003).

The light-dependency activity of these compounds as TNF-alpha antagonists suggests that the compounds disclosed in these publications are artifacts, having artificial properties that cannot be exhibited in a human body (where there is no light). Thus, no definite biological activity of rigid rhodanine-based compounds in taught in these publication. In addition, while these publications teach the artificial binding of these compounds to TNF-alpha, these publications are completely silent with respect to the activity of such compounds as modulators of heparanase activity, of heparin-binding proteins activity and as active agents that affect other biological pathways.

There is thus a widely recognized need for, and it would be highly advantageous to have, novel rhodanine-based compounds, having a rigidified structure, which could be efficiently utilized for modulating heparanase and/or heparin-binding proteins activities, as well as other biological processes, preferably in a non light-dependent manner.

SUMMARY OF THE INVENTION

While reducing the present invention to practice, a plurality of rigidified compounds, being derivatives of rhodanine or rhodanine analogs, have been designed and successfully prepared. These compounds have shown heparanase, pro-heparanase, heparin-binding protein and cell invasion inhibition activities.

Thus, according to one aspect of the present invention there is provided a rigidified compound comprising a rhodanine or a rhodanine analog residue and a core structure which comprises:

(a) the rhodanine or the rhodanine analog residue being covalently attached to a first aryl or heteroaryl residue, such that the core structure has one or zero free-to-rotate bonds, wherein the aryl is a five-membered or seven-membered aryl; and/or (b) a first aryl or heteroaryl residue which is covalently attached to a second aryl or heteroaryl residue, such that the core structure has one or zero free-to-rotate bonds.

Excluded from the scope of this aspect of the present invention are the compounds 2-(3-methoxy-phenyl)-5-(3-morpholin-4-yl-propyl)-4-thioxo-4,5-dihydro-1-thia-3b,5-diaza-cyclopenta[a]pentalen-6-one and 5-(3-morpholin-4-yl-propyl)-2-(3-nitro-phenyl)-4-thioxo-4,5-dihydro-1-thia-3 b,5-diaza-cyclopenta[a]pentalen-6-one.

According to further features in preferred embodiments of the invention described below, the core structure further comprises at least one linking moiety connecting at least two radicals in the core structure.

According to still further features in the described preferred embodiments the rhodanine or rhodanine analog residue has a general Formula I:

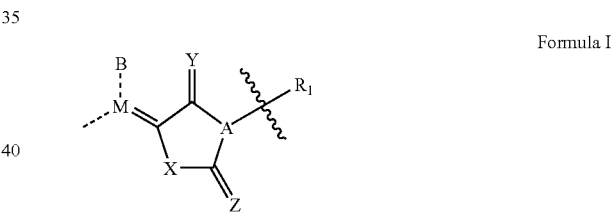

Formula I whereas:

the wavy line indicates a part of the rhodanine or rhodanine analog residue which is included in the core structure;

the dashed lines indicate either a Z-configuration or an E-configuration of B with respect to Y;

A is N or CRa;

X is O, S, NRb, NRb—C(=D), CRbRc or CRbRc-C(=D);

Y and Z are each independently O, S, Se, NRd, CRdRe or RdC=CRe;

M is N, P, C or Si;

B is selected from the group consisting of a lone pair of electrons, hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl;

Ra, Rb, Rc, Rd, and Re are each independently selected from the group consisting of hydrogen, a substituted or unsubstituted alkyl, a substituted or unsubstituted cycloalkyl, and a substituted or unsubstituted aryl;

$R_1$ is selected from the group consisting of hydrogen, a substituted or unsubstituted alkyl, a substituted or unsubsti-tuted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic and a moiety having the general Formula II:

—(CH$_2$)$n$-CH(Rq)-Q$_1$;   Formula II and further whereas:

D is O, S, NRm or CRmRp;

Rm and Rp are each independently selected from the group consisting hydrogen, a substituted or unsubstituted alkyl, a substituted or unsubstituted cycloalkyl, and a substituted or unsubstituted aryl;

n is integer that equals 0-20;

Rq is selected from the group consisting of hydrogen, alkyl and Q$_2$;

Q$_1$ and Q$_2$ are each independently selected from the group consisting of hydrogen, C-carboxylate, amide, sulfonate, sulfonamide, phosphonate, phosphonamide, borate and silyl; and each of the substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide.

According to still further features in the described preferred embodiments the first aryl or heteroaryl residue has a general Formula selected from the group consisting of Formula IIIa, IIIb, IIIc and IIId:

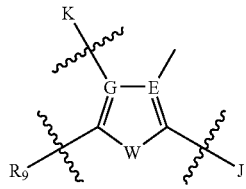

Formula IIIc whereas:

the wavy lines indicate a part of the aryl or heteroaryl residue which is included in the core structure which comprises the rhodanine or rhodanine analog residue;

W is O, S, NRd, CRdRe or RdC=CRe;

E and G are each independently N or CRs;

J and K are each independently a lone pair of electrons, ORi, SRi, NRiRj, CRiRjRk, hydrogen, alkyl, hydroxy, thiohydroxy, alkoxy, thioalkoxy, halo, nitro, trihaloalkyl, C-carboxylate, O-carboxylate, C-amide, N-amide, S-sulfonamide, N-sulfonamide or absent, or, alternatively, J and K form a five- or six-membered ring;

Rd, Re, Ri, Rj, Rk and Rs are each independently hydrogen, a substituted or unsubstituted alkyl, a substituted or unsubstituted cycloalkyl, and a substituted or unsubstituted aryl; and R$_9$ is selected from the group consisting of hydrogen, a substituted or unsubstituted alkyl, a substituted or unsubstituted cycloalkyl, a substituted or unsubstituted aryl and a substituted or unsubstituted heteroaryl, or, alternatively, at least two of J, K and R$_9$ form a 5- or 6-membered ring, and further whereas each of the substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide.

According to still further features in the described preferred embodiments R$_9$ is a second aryl or heteroaryl having the general Formula IV:

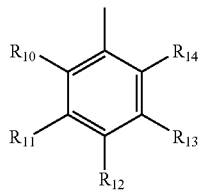

Formula IV wherein each of R$_{10}$-R$_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of R$_{10}$-R$_{14}$ form a five- or six-membered cyclic, heteroalicyclic, aromatic or heteroaromatic ring.

According to still further features in the described preferred embodiments each of the first and the second aryl residue independently has a general Formula selected from the group consisting of Formula IVa and Formula IVb:

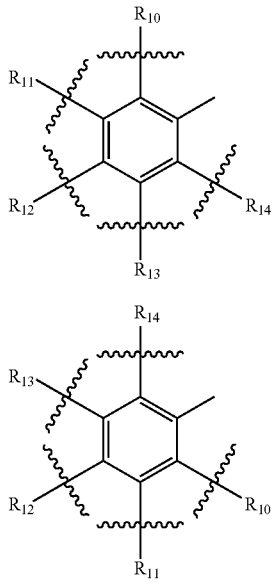

Formula IVa

Formula IVb whereas:

the wavy lines indicate a part of the aryl or heteroaryl residue which is included in the core structure; and each of $R_{10}$-$R_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of $R_{10}$-$R_{14}$ form a five- or six-membered ring.

According to still further features in the described preferred embodiments the core structure which comprises the rhodanine or the rhodanine analog residue being covalently attached to the first aryl or heteroaryl residue has the general Formula selected from the group consisting of Formula Va and Formula Vb:

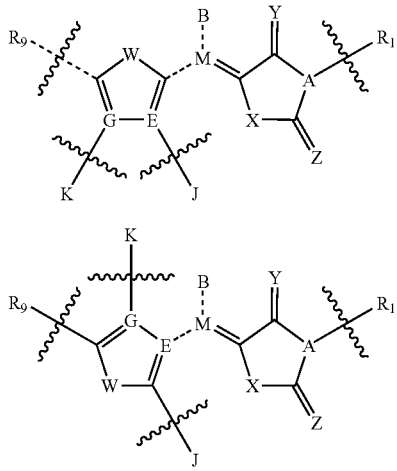

Formula Va

Formula Vb wherein:

the wavy lines indicate a part of the rhodanine or rhodanine analog residue and a part of the first aryl or heteroaryl residue which are included in the core structure;

the dashed lines indicate either a Z-configuration or an E-configuration of B with respect to Y; and (ii) a first aryl or heteroaryl residue having the Formula IIIa, IIIb, IIIc or IIId;

A is N or CRa;

X is O, S, NRb, NRb—C(=D), CRbRc or CRbRc-C(=D);

Y, Z, and W are each independently O, S, Se, NRd, CRdRe or RdC=CRe;

M is N, P, C or Si;

B is selected from the group consisting of a lone pair of electrons, hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl;

E and G are each independently N or CRs;

J and K are each independently a lone pair of electrons, ORi, SRi, NRiRj, CRiRjRk, hydrogen, alkyl, hydroxy, thiohydroxy, alkoxy, thioalkoxy, halo, nitro, trihaloalkyl, C-carboxylate, O-carboxylate, C-amide, N-amide, S-sulfonamide, N-sulfonamide or absent, or, alternatively, J and K form a five- or six-membered ring;

Ra, Rb, Rc, Rd, Re, Ri, Rj, Rk and Rs are each independently hydrogen, a substituted or unsubstituted alkyl, a substituted or unsubstituted cycloalkyl, and a substituted or unsubstituted aryl;

$R_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic and a moiety having the general Formula II;

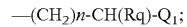  Formula II and $R_9$ is selected from the group consisting of hydrogen, a substituted or unsubstituted alkyl, a substituted or unsubstituted cycloalkyl, a substituted or unsubstituted aryl and a substituted or unsubstituted heteroaryl, or, alternatively, at least two of E, G and $R_9$ form a 5- or 6-membered alicyclic, heteroalicyclic, aromatic or heteroaromatic ring;

whereas:

D is O, S, NRm or CRmRp;

Rm and Rp are each independently selected from the group consisting hydrogen, a substituted or unsubstituted alkyl, a substituted or unsubstituted cycloalkyl, and a substituted or unsubstituted aryl; and n is integer that equals 0-20;

Rq is selected from the group consisting of hydrogen, alkyl and $Q_2$;

$Q_1$ and $Q_2$ are each independently selected from the group consisting of hydrogen, C-carboxylate, amide, sulfonate, sulfonamide, phosphonate, phosphonamide, borate and silyl; and each of the substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide, and further wherein:

the core structure further comprises at least one linking moiety connecting at least two radicals of A, B, E, G, J, K, X, Y and/or W.

According to still further features in the described preferred embodiments $R_9$ is an aryl having a general Formula selected from the group consisting of Formula IVa or IVb:

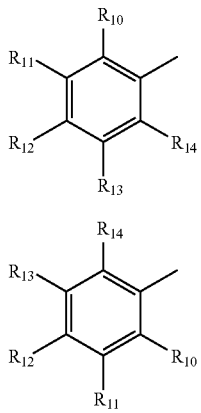

Formula IVa

Formula IVb whereas:

each of $R_{10}$-$R_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of $R_{10}$-$R_{14}$ form a five- or six-membered ring.

According to still further features in the described preferred embodiments the core structure which comprises the first aryl or heteroaryl residue being covalently attached to the second aryl or heteroaryl residue has a general formula selected from the group consisting of Formula VIa and Formula VIb:

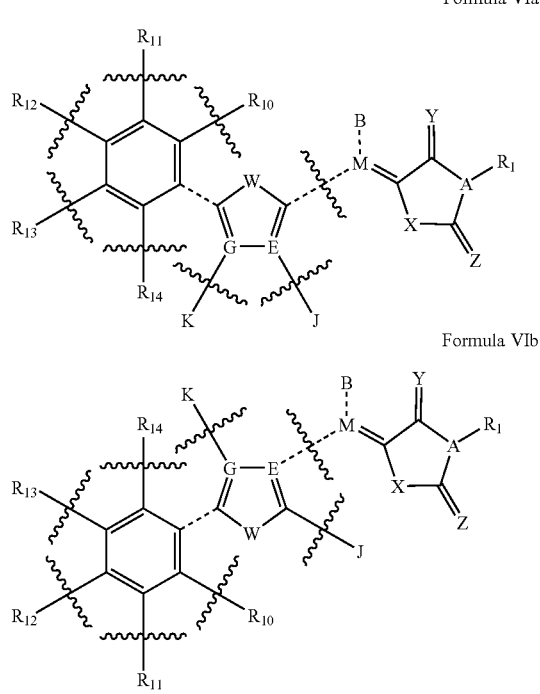

Formula VIa

Formula VIb wherein:

the wavy lines indicates parts of the first and the second aryl or heteroaryl residues which are included in the core structure;

the dashed lines indicate (i) either a Z-configuration or an E-configuration of B with respect to Y; (ii) a first aryl or heteroaryl residue having the Formula IIIa, IIIb, IIIc or IIId; and (iii) a second aryl or heteroaryl residue having the Formula IVa or IVb;

A is N or CRa;

X is O, S, NRb, NRb—C(=D), CRbRc or CRbRc-C(=D);

Y, Z, and W are each independently O, S, Se, NRd, CRdRe or RdC=CRe;

M is N, P, C or Si;

B is selected from the group consisting of a lone pair of electrons, hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl;

E and G are each independently N or CRs;

J and K are each independently a lone pair of electrons, ORi, SRi, NRiRj, CRiRjRk, hydrogen, alkyl, hydroxy, thiohydroxy, alkoxy, thioalkoxy, halo, nitro, trihaloalkyl, C-carboxylate, O-carboxylate, C-amide, N-amide, S-sulfonamide, N-sulfonamide or absent, or, alternatively, J and K form a five- or six-membered ring;

Ra, Rb, Rc, Rd, Re, Ri, Rj, Rk and Rs are each independently hydrogen, a substituted or unsubstituted alkyl, a substituted or unsubstituted cycloalkyl, and a substituted or unsubstituted aryl;

$R_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic and a moiety having the general Formula II:

$$-(CH_2)n\text{-}CH(Rq)\text{-}Q_1;\qquad\text{Formula II}$$

and $R_9$ is selected from the group consisting of hydrogen, a substituted or unsubstituted alkyl, a substituted or unsubstituted cycloalkyl, a substituted or unsubstituted aryl and a substituted or unsubstituted heteroaryl, or, alternatively, at least two of E, G and $R_9$ form a 5- or 6-membered alicyclic, heteroalicyclic, aromatic or heteroaromatic ring; and $R_{10}$-$R_{14}$ are each independently absent or is selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide, and N-sulfonamide, or absent or, alternatively, at least two of $R_{10}$-$R_{14}$ form a five- or six-membered cyclic, heteroalicyclic, aromatic or heteroaromatic ring.

whereas:

D is O, S, NRm or CRmRp;

Rm and Rp are each independently selected from the group consisting hydrogen, a substituted or unsubstituted alkyl, a substituted or unsubstituted cycloalkyl, and a substituted or unsubstituted aryl; n is integer that equals 0-20;

Rq is selected from the group consisting of hydrogen, alkyl and $Q_2$;

$Q_1$ and $Q_2$ are each independently selected from the group consisting of carboxylate, amide, sulfonate, sulfonamide, phosphonate, borate and silyl; and each of the substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide, and further wherein:

the core structure further comprises at least one linking moiety connecting at least two radicals of W, E, J, K and/or $R_{10}$-$R_{14}$.

According to still further features in the described preferred embodiments the at least one linking moiety is selected from the group consisting of a single bond and a double bond.

According to still further features in the described preferred embodiments the core structure comprises 1-5 linking moieties.

According to still further features in the described preferred embodiments at least one of the linking moieties connects radicals of B and Y.

According to still further features in the described preferred embodiments the radical of B is S and the radical of Y is N.

According to still further features in the described preferred embodiments the radical of B is O and the radical of Y is N.

According to still further features in the described preferred embodiments at least one of the linking moieties connects radicals of W and X.

According to still further features in the described preferred embodiments the radical of W is N and the radical of X is N.

According to still further features in the described preferred embodiments at least one of the linking moieties corrects radicals of W and Y.

According to still further features in the described preferred embodiments each of the radicals of W and Y is N.

According to still further features in the described preferred embodiments at least one of the linking moieties connects radicals of J and Y.

According to still further features in the described preferred embodiments at least one of the linking moieties connects radicals of J and B.

According to still further features in the described preferred embodiments at least one of the linking moieties connects radicals of W and B.

According to still further features in the described preferred embodiments at least one of the linking moieties connects radicals of E and X.

According to still further features in the described preferred embodiments the radical of X is N and the radical of E is C.

According to still further features in the described preferred embodiments at least one of the linking moieties connects radicals of J and X.

According to still further features in the described preferred embodiments the radical of X is N and the radical of J is C=O.

According to still further features in the described preferred embodiments one of the linking moieties connects radicals of B and Y and one of the linking moieties connects radicals of E and X.

According to still further features in the described preferred embodiments the radical of B is S; the radical of Y is N; the radical of X is N and the radical of E is C.

According to still further features in the described preferred embodiments the radical of B is O; the radical of Y is N; the radical of X is N and the radical of E is C.

According to still further features in the described preferred embodiments B is selected from the group consisting of alkoxy, thioalkoxy and amine; Y and W are each independently NRd; and X is NRb.

According to still further features in the described preferred embodiments one of the linking moieties connects radicals of B and Y and one of the linking moieties connects radicals of W and X.

According to still further features in the described preferred embodiments at least one of the linking moieties connects radicals of E and Y.

According to still further features in the described preferred embodiments the radical of E is C and the radical of Y is N.

According to still further features in the described preferred embodiments $R_1$, in any of the compounds described herein, is a moiety having the general Formula II, wherein, preferably, n equals 2-5.

According to still further features in the described preferred embodiments $R_1$, in any of the compounds described herein, is a substituted or unsubstituted heteroaryl or a substituted or unsubstituted aryl.

According to still further features in the described preferred embodiments W, in any of the compounds described herein, is O or S.

According to still further features in the described preferred embodiments $R_{10}$ and $R_{14}$ are each independently selected from the group consisting of hydrogen, alkyl, cycloalkyl, hydroxy, alkoxy, thiohydroxy, thioalkoxy, aryloxy and thioaryloxy; and $R_{11}$-$R_{13}$ are each independently selected from the group consisting of hydrogen, halo, nitro, trihaloalkyl and C-carboxylate.

According to still further features in the described preferred embodiments $R_9$ is a substituted or unsubstituted benzothiazole.

According to still further features in the described preferred embodiments the rigidified compound described herein is selected from the group consisting of the compounds set forth in Table 2.

According to still further features in the described preferred embodiments a rigidified compound as described herein is capable of modulating heparanase activity.

According to still further features in the described preferred embodiments a rigidified compound as described herein is capable of modulating heparin-binding protein activity.

According to still further features in the described preferred embodiments the modulating is effected in the presence or in the absence of light.

According to another aspect of the present invention there is provided a pharmaceutical composition comprising, as an active ingredient, the rigidified compound as described herein and a pharmaceutically acceptable carrier.

According to further features in preferred embodiments of the invention described below, the pharmaceutical composition is packaged in a packaging material and identified in print, in or on the packaging material, for use in the treatment of a medical condition selected from the group consisting of a medical condition in which regulating, modulating and/or inhibiting an activity of heparanase is beneficial, a heparanase associated disease or disorder, a heparin binding protein associated disease or disorder and a medical condition at least partially treatable by a compound having a rhodanine skeleton.

According to yet another aspect of the present invention there is provided a use of a rigidified compound which comprises a rhodanine or a rhodanine analog residue and a core structure, for the preparation of a medicament, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds, as described hereinabove.

According to further features in preferred embodiments of the invention described below, the medicament is for regulating a biological process depending at least in part on heparanase activity.

According to still further features in the described preferred embodiments the medicament is for treating a heparanase associated disease or disorder.

According to still further features in the described preferred embodiments the medicament is for treating a heparin binding protein associated disease or disorder.

According to still further features in the described preferred embodiments the medicament is for treating a medical condition at least partially treatable by a rhodanine and/or a rhodanine analog.

According to still another aspect of the present invention there is provided a method of regulating a biological process depending at least in part on heparanase activity, the method comprising inhibiting heparanase activity by a rigidified compound which comprises a rhodanine or a rhodanine analog residue and a core structure, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds, as described herein.

According to further features in preferred embodiments of the invention described below, the biological process is selected from the group consisting of cell migration, cell invasion, cell implantation, cell transplantation, cell extravasation, bone formation, cell adhesion, embryo implantation, neurodegenerative disorders, autoimmune diseases, atherosclerosis, viral infections, restenosis, skeletal muscle calcium kinetics, diabetic nephropathy, epidermal differentiation and desquamation, HS-involved metabolic disorders, prion diseases, hair growth, angiogenesis, neovascularization, cancer development, metastases formation, wound healing, inflammation and immune recognition.

According to an additional aspect of the present invention there is provided a method of treating a heparanase associated disease or disorder in a subject, the method comprising administering to the subject in need thereof a therapeutically effective amount of a rigidified compound which comprises a rhodanine or a rhodanine analog residue and a core structure, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds, as described herein.

According to yet an additional aspect of the present invention there is provided a method of inhibiting heparanase activation, the method comprising contacting an inactive heparanase with a rigidified compound which comprises a rhodanine or a rhodanine analog residue and a core structure, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds, as described herein.

According to still an additional aspect of the present invention there is provided a method of inhibiting heparanase activity, the method comprising contacting the heparanase with a rigidified compound which comprises a rhodanine or a rhodanine analog residue and a core structure, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds, as described herein.

According to a further aspect of the present invention there is provided a method of inhibiting heparin binding protein, the method comprising contacting the heparin binding protein with a rigidified compound which comprises a rhodanine or a rhodanine analog residue and a core structure, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds, as described herein.

According to yet a further aspect of the present invention there is provided a method for inhibiting heparin binding protein, the method comprising contacting heparin with a rigidified compound which comprises a rhodanine or a rhodanine analog residue and a core structure, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds.

According to still a further aspect of the present invention there is provided a method for treating a heparin binding protein associated disease or disorder, the method comprising administering to a subject in need thereof a therapeutically effective amount of a rigidified compound which comprises a rhodanine or a rhodanine analog residue and a core structure, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds, as described herein.

According to a further aspect of the present invention there is provided a method of treating a medical condition at least partially treatable by a rhodanine and/or a rhodanine analog, the method comprising administering to a subject in need thereof a therapeutically effective amount of a rigidified compound which comprises a rhodanine or a rhodanine analog residue and a core structure, wherein the core structure comprises:

(a) the rhodanine or the rhodanine analog residue being covalently attached to a first aryl or heteroaryl residue, such that the core structure has one or zero free-to-rotate bonds; and/or (b) a first aryl or heteroaryl residue which is covalently attached to a second aryl or heteroaryl residue, such that the core structure has one or zero free-to-rotate bonds, as described herein.

Representative examples of medical conditions that are at least partially treated by rhodanine include, without limitation, Alzheimer's disease, schizophrenia, atherosclerosis, an autoimmune disease or disorder, a bacterial infection, a blood coagulation disease or disorder, a bone disease or disorder, cancer, a cardiovascular disease or disorder, a CNS disease or disorder, diabetes, a fungal infection, a gastro-intestinal disease or disorder, hair loss, hypercholesterolemia, inflammation, pain and a viral infection.

According to further features in preferred embodiments of the invention described below, the rigidified compound utilized in each of the methods and uses described herein comprises a first aryl or heteroaryl residue is which the aryl residue is a five-membered aryl residue or a seven-membered aryl residue.

According to still further features in the described preferred embodiments each of the method or uses described herein is effected in the presence or in the absence of light.

The present invention successfully addresses the shortcomings of the presently known configurations by providing novel rigidified rhodanine-based compounds which are highly potent inhibitors of heparanase activity, heparanase activation, heparin-binding proteins and cell invasion and can therefore be efficiently utilized in various therapeutic applications.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The term "active ingredient" refers to a pharmaceutical agent including any natural or synthetic chemical substance that subsequent to its application has, at the very least, at least one desired pharmaceutical or therapeutic effect.

The term "therapeutically effective amount" or "pharmaceutically effective amount" denotes that dose of an active ingredient or a composition comprising the active ingredient that will provide the therapeutic effect for which the active ingredient is indicated, herein, modulating and preferably elevating an NO level.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

DESCRIPTION OF THE PREFERRED EMBODIMENTS

The present invention is of novel rigidified compounds which have a rhodanine or a rhodanine analog residue and one or more aryl or heteroaryl residue(s), and a core structure that is characterized by a minimized number of free-to-rotate bonds (e.g., one or zero). The present invention is further of pharmaceutical compositions containing these rigidified compounds and of uses thereof in the treatment of a variety of medical conditions. Thus, the present invention is of rhodanine- or rhodanine analog-based rigidified compounds which can be used for modulating the activity of heparanase and hence in the treatment of heparanase-associated diseases and disorders, for modulating the activity of heparin-binding proteins and hence in the treatment of heparin-binding proteins-associated diseases and disorders and/or in the treatment of other medical conditions that are treatable by rhodanine or a rhodanine analog.

As discussed hereinabove, it has been recently found that rhodanine-based compounds can serve as efficient modulators of heparanase activity, a key GAG-degrading enzyme, and hence can be used in the treatment of medical conditions wherein heparanase activity modulation is beneficial. A family of such rhodanine-based compounds is disclosed in U.S. patent application Ser. No. 10/916,598, by the present assignee, which is incorporated by reference as if fully set forth herein. The effect of the various substituents present in various positions of these rhodanine-based compounds on the nature and aptitude of the activity of these compounds have also been demonstrated. Thus, for example, it was found that compounds wherein $R_1$ (see, discussion of the rhodanine-based compounds taught in U.S. patent application Ser. No. 10/916,598, set forth hereinabove) is an acid-containing alkyl-chain moiety (e.g. carboxylic acid or sulfonic acid) having a chain length of three or more carbons, and/or at least one of the $R_{10}$-$R_{14}$ is an acidic moiety, exhibited high activity. It was also found that introducing a hydrophobic group in the 5-position of the furan group, such as a phenyl ring, improves the biological activity of these rhodanine-based compounds. For optimal activity, electron-withdrawing substituents (e.g. Cl, Br, $NO_2$) at the meta or para position on the phenyl ring attached to the 5-position of the furan group, are preferred.

While the compounds disclosed in U.S. patent application Ser. No. 10/916,598 exhibited a fairly good efficacy as modulators of heparanase activity, more potent agents are still required.

As further discussed hereinabove, rhodanine-based compounds are also known to affect a wide scope of other medical conditions, including, for example, CNS diseases and disorders, blood and bone disorders, autoimmune diseases, fungal, bacterial and viral infections, cancer, gastro-intestinal diseases and disorders, inflammation and pain. While such a wide-scoped biological activity can be harnessed in drug-development, it is well-known in the art that such an indiscriminate activity may lead to toxic and other adverse effects due to lack of specificity. Such lack of specificity may be attributed to the multiple molecular conformations that rhodanine-based compounds can potentially exhibit.

As is well-known in the art, the binding of a small molecule, such as the rhodanine-based compounds taught in U.S. patent application Ser. No. 10/916,598, to a binding site of a target such as a protein (e.g., an enzyme or a receptor) is governed not only by the number and strength of the interactions between chemical groups of both the small molecule and the binding side, but also by the thermodynamic balances of free energy and entropy of the small molecule. Accordingly, the interactions of flexible molecules, having numerous free-to-rotate bonds and thus numerous molecular conformations, with a binding site are characterized by high free energy and entropy and hence by high overall binding energy. The interactions of rigid molecules, having a minimized number or no free-to-rotate bonds and thus a limited number or even a single molecular conformation, with the binding site are characterized by low free energy and entropy and hence by low overall binding energy. Consequently, flexible molecules have a lower affinity to the target as compared with rigid compounds that have the same chemical groups but reduced number of free-to-rotate bonds and hence reduced number of molecular conformations.

The phrase "free-to-rotate bond", as used herein, describes a bond that connects two moieties in a compound, which is capable of rotating around an axis, whereby such a rotation affects the relative positions of these moieties, and results in numerous (e.g., two or more) three-dimensional molecular conformations of the compound. A free-to-rotate bond, according to the present invention, includes a single (sigma) bond which has an ability to rotate along its axis, a partial double bond which may isomerize (spontaneously or not) from a Z-configuration to an E-configuration, as these are defined hereunder, a double bond which can exhibit a fixed Z-configuration or an E-configuration or any bond which is not substantially restricted from having more than one conformation. The existence of a free-to-rotate bond in a compound introduces the capacity of the compound to exist in more than one three-dimensional structure (molecular conformation), hence the reduction of the number of free-to-rotate bonds in a compound reduces the number of possible conformations, preferably to a single molecular conformation.

In a search for rhodanine-based compounds that would exhibit improved performance, either as heparanase and/or heparin-binding protein activity modulators or as agents for treating other conditions, as described hereinabove, the present inventors have envisioned that such an improved performance could be achieved by enhancing the binding affinity of the compounds to a designated target, whereby such an enhancement could be obtained by rigidification of rhodanine-based compounds. More particularly, it was envisioned that by such a rigidification, the number of free-to-rotate bonds within the compounds would be reduced, leading to a reduced degree of freedom and restricted molecular conformations of these compounds as compared with non-rigidified compounds and thus to a pre-determined, fixed three-dimensional structure of the resulting rigidified compound. It was thus further envisioned that rhodanine-based compounds having such a fixed three-dimensional structure could be designed so as to more efficiently and selectively bind to a designated target.

While reducing the present invention to practice, a plurality of rigidified rhodanine- and rhodanine analog-based compounds was designed following the underlying principles outlined in U.S. patent application Ser. No. 10/916,598, and were readily synthesized. As is demonstrated in the Examples section that follows, several models of rigidification were successfully practiced to thereby produce rhodanine-based and rhodanine analog-based compounds having a rigidified core structure "decorated" with a variety of substituents. As further demonstrated in the Examples section that follows, these compounds were indeed found active in modulating heparanase activation, as well as in inhibiting β-FGF and VEGF binding to heparin.

Thus, according to one aspect of the present invention, each of the rigidified compounds presented herein has structural features similar to the rhodanine-based compounds that were previously found as active heparanase activity modulators (see, U.S. patent application Ser. No. 10/916,598), namely, has a rhodanine-like residue covalently linked to an aryl or a heteroaryl residue, which in turn, may optionally be linked to another aryl or heteroaryl residue. However, each of the rigidified compounds described herein is further characterized by one or two rigid core-structure(s) each having one or zero free-to-rotate bond.

As used herein throughout, the phrase "rhodanine-based compounds" describes compounds having a rhodanine or a rhodanine analog residue, as these terms are defined herein.

The phrase "rhodanine-like residue" and the phrase "rhodanine or rhodanine analog residue" are used herein interchangeably.

More specifically, each of the rigidified compounds presented herein comprises a rhodanine or a rhodanine analog residue and one or more of the following rigidified core structures:

(i) a core structure which comprises the rhodanine or rhodanine analog residue being covalently attached to a first aryl or a heteroaryl residue, such that the core structure has one or zero free-to-rotate bonds (also referred to hereinafter as core structure I); and/or (ii) a first aryl or a heteroaryl residue which is covalently attached to a second aryl or a heteroaryl residue, such that the core structure has one or zero free-to-rotate bonds (also referred to hereinafter as core structure II).

Excluded from the scope of this aspect of the present invention are compounds having a core structure which comprises the rhodanine or rhodanine analog residue being covalently attached to a first aryl or a heteroaryl residue, such that the core structure has one or zero free-to-rotate bonds, in which the aryl residue is a six-membered aryl residue. Some compounds that have such a structure are known in the art (e.g., 2-methyl-3-thioxo-2,3-dihydro-imidazo[1,5-a]indol-1-one, see, for example, Katritzky et al., J. Org. Chem., 69, 9313, 2004), while the biological effect of these compounds, particularly as modulators of heparanase activity and/or modulators of heparin-binding protein activity, has not been demonstrated.

Other compounds that have such a structure have been described in Voss et al. (supra). However, as discussed hereinabove, these compounds were found to act as artifacts, being active as TNF-alpha antagonists only in the presence of light.

Further excluded from the scope of this aspect of the present invention are two compounds having a N-(3-morpholino)propyl rhodanine analog residue being covalently attached to a 5-(3-methoxyphenyl)thiophene group and a 5-(3-nitrophenyl)thiophene group, which have been disclosed in Carter et al. (Proc. Natl. Acad. Sci., 98, 11879, 2001, see, compounds denoted IW927 and IV703). These compounds are also taught as being active as TNF-alpha antagonists only in the presence of light.

While the reported biological activity of the compounds disclosed in Carter et al. and Voss et al. (supra) is questionable, being light-dependent and directed to binding TNF-alpha, these compounds are not excluded from the scope of other aspects of the present invention, detailed hereinunder, particularly in light of the findings that the compounds of present embodiments were found biologically active both in the presence and absence of light, as detailed hereinbelow.

In compounds having a core structure in which a first aryl or a heteroaryl residue is covalently attached to a second aryl or a heteroaryl residue, such that the core structure has one or zero free-to-rotate bonds, the first and the second aryl residue can be of any ring-order, e.g. be a 4-, 5-, 6-, 7- or 8-membered aryl residue.

In each of the rigidified compounds presented herein, the core structures preferably comprises one or more linking moieties, as these are defined hereinbelow, connecting at least two radicals, as these are defined hereinbelow, in the core structure. By connecting radicals in the core structures, rigidification is effected, as is detailed and exemplified hereinbelow.

The phrase "core structure" as used herein refers to that part of the compound which comprises the basic structures of the rhodanine-like residue and the aryl or heteroaryl residue(s), whereby by "basic structure" it is meant the ring structure itself, excluding the substituents that might be present at each of these residues. As is taught in U.S. patent application Ser. No. 10/916,598, the activity of the compounds disclosed therein is attributed to the presence of these basic structures and hence these basic structures constitute the core structure of the compounds described herein. Due to the attribute of the core structure to the activity of the compounds, rigidification of the core structure beneficially affects their binding properties. Thus, the phrase "core structure" as used herein further refers to the part of the compound in which rigidification is effected, namely, the part of the compound which has a rigid scaffold, as compared to a corresponding non-rigidified compound. The various rigid core structures described herein are presented either as the already rigidified structures or by generally presenting a pre-rigidified structure which is rigidified via one or more of the rigidification strategies described hereinbelow.

Following the guidelines of the structural features determined in U.S. patent application Ser. No. 10/916,598 for the rhodanine-based active agents, each of the compounds described herein are derived from a compound that has a rhodanine or a rhodanine analog residue.

The phrase "rhodanine or rhodanine analog residue", as used herein, describes a rhodanine-like residue of a corresponding pre-rigidified compound and encompasses residues of various derivatives of a compound that has a rhodanine skeleton or a rhodanine analog skeleton, as is detailed hereinbelow. Thus, while the rigidification of some of the compounds described herein involves that part of the compound which includes the rhodanine-like residue (e.g., as in core structure I), such a rigidification may involve chemical and structural changes in the rhodanine-like residue. Nevertheless, these changes where designed so as not to affect the structural and chemical features that are essential for the activity of these compounds.

The term "analog" as used herein with regard to a certain (original) compound or a residue refers to a compound or a residue which has similar, yet different, structural features as compared with the original compound or the residue, respectively, but which maintains the structural features that are required for its activity.

The term "rhodanine analog", as used herein, therefore refers to a compound which is analogous to rhodanine, i.e., share resemblance of several chemical and structural characteristics of rhodanine, yet can exhibit some differences and alterations with respect to, for example, the type of heteroatoms, the ring order and the location and nature of its substituents.

The term "residue", as used herein, refers to a major portion of a molecule, which is chemically linked to one or more other molecules.

The term "derivative" describes a compound which has been subjected to a chemical modification while maintaining its main structural features (e.g., its skeleton). Thus, such chemical modifications can include, for example, changes of one or more substituents.

The phrase "rhodanine or rhodanine analog residue", as used herein, therefore describes a residue of rhodanine or a rhodanine analog, as well as various derivatives thereof, which can be collectively represented by the general Formula I:

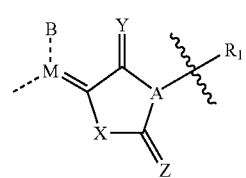

Formula I wherein:

A is N or CRa;

X is O, S, NRb, NRb—C(=D), CRbRc or CRbRc-C(=D);

Y and Z are each independently O, S, Se, NRd, CRdRe or RdC=CRe;

M is N, P, C or Si;

B is selected from the group consisting of a lone pair of electrons, hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl, as these terms are defined hereinbelow;

Ra, Rb, Rc, Rd, and Re are each independently selected from the group consisting of hydrogen, a substituted or unsubstituted alkyl, a substituted or unsubstituted cycloalkyl, and a substituted or unsubstituted aryl, as these terms are defined hereinbelow;

$R_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic, as these terms are defined hereinbelow, and a moiety having the general Formula II:

$$-(CH_2)n\text{-}CH(Rq)\text{-}Q_1;$$ Formula II and further whereas:

D is O, S, NRm or CRmRp;

Rm and Rp are each independently selected from the group consisting hydrogen, a substituted or unsubstituted alkyl, a substituted or unsubstituted cycloalkyl, and a substituted or unsubstituted aryl, as these terms are defined hereinbelow;

n is integer that equals 0-20;

Rq is selected from the group consisting of hydrogen, alkyl and $Q_2$;

$Q_1$ and $Q_2$ are each independently selected from the group consisting of hydrogen, C-carboxylate, amide, sulfonate, sulfonamide, phosphonate, phosphonamide, borate and silyl, as these terms are defined hereinbelow; and each of the substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide, as these terms are defined hereinbelow.

The wavy line delineates that part of the rhodanine-like residue that is included in the rigidified core structure, in cases where the rigidified compound comprises the core structure I.

The dashed lines in Formula I indicate either a Z-configuration or an E-configuration of the bond between the ring and M, as determined by B with respect to X.

The terms "Z-configuration" and "E-configuration" as these are used herein are the same stereodescriptors defined by the Chemical Abstract Service to resolve cases where cis/trans terminology of stereoisomeric alkenes is ambiguous. Briefly, the chemical group of highest CIP priority attached to one of the terminal doubly bonded atoms of the alkene, oxime, cumulene and the likes is compared with the group of highest precedence attached to the other. The stereoisomer is designated as having a Z-configuration (Z stands for "zusammen" which translate from German to "together") if the groups lie on the same side of a reference plane passing through the double bond and perpendicular to the plane containing the bonds linking the groups to the double-bonded atoms. The other stereoisomer is designated as having an E-configuration (E stands for "entgegen" which translate from German to "opposite"). The descriptors may be applied to structures with a fractional bond order between one and two and to double bonds involving elements other than carbon. The CIP Priority rules define the conventional order of chemical groups established for the purpose of unambiguous designation of stereoisomers. It is deduced by application of sequence rules, the authoritative statement of which appears in R. S. Cahn, C. K. Ingold and V. Prelog, Angew. Chem. 78, 413-447 (1966), Angew. Chem. Internat. Ed. Eng. 5, 385-415, 511 (1966); and V. Prelog and G. Helmchen, Angew. Chem. 94, 614-631 (1982), Angew. Chem. Internat. Ed. Eng. 21, 567-583 (1982).

Specifically, the various conformations of the rhodanine or the rhodanine analog residue can be represented by formula Ia and Ib:

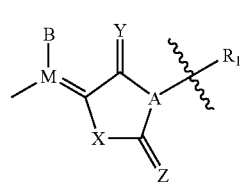

Formula Ia

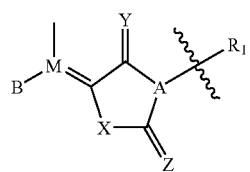

Formula Ib whereby each of Formula Ia and Formula Ib represents either the Z-conformer or the E-conformer, as determined by the CIP priorities of the chemical groups attached to the doubly bonded atoms.

In cases where the rhodanine-like residue is derived from rhodanine derivatives having a rhodanine skeleton, in Formulae I, Ia and Ib above X is S; Y is O; Z is S; A in N; M is C and B is hydrogen. Compounds having such a rhodanine residue in the corresponding pre-rigidified compounds are preferred compounds according to the present embodiments.

In cases where the rhodanine-like residue is derived from derivatives of a rhodanine analog, in Formulae I, Ia and Ib, preferred compounds are those deriving from a pre-rigidified compound in which, for example, X is S; Y is O; and Z is O, or in which X is $NR_5$—C=D; Y is O; Z is O or S; and D is O or S (2-thio/oxo-dihydro-pyrimidine-4,6-dione).

As discussed in detail in U.S. patent application Ser. No. 10/916,598, it is assumed that the carbonyl moiety (Y) or the carbonyl/thiocarbonyl (Z), which is present in the skeleton of all such compounds, interacts, via hydrogen bonding, with one of the heparin-binding domains of pro-heparanase.

As is further discussed and shown in detail in U.S. patent application Ser. No. 10/916,598 and is further demonstrated herein, another component which may impact the binding potency of the compounds described herein is the substituent $R_1$. As shown in Formula I hereinabove and in additional formulae presented herein, this substituent is not part of the core structure and hence may present additional free-to-rotate bonds to the compound as a whole (while not affecting the number of free-to-rotate bonds in the core structure).

Preferred compounds according to the present embodiments have a rhodanine-like skeleton, as described hereinabove, and an $R_1$ substituent which has Formula II as presented hereinabove.

Specifically, compounds wherein $R_1$ is an unsubstituted or a substituted alkyl-chain, terminally substituted by one or more acidic moieties such as, for example, a carboxylic acid (C-carboxylate), a sulfonic acid (sulfonate), a phosphonic acid (phosphonate) or a boronic acid (borate), and derivatives thereof, such as esters, amides and hydroxyamides thereof were shown to have improved efficacy.

As mentioned above, the length of the alkyl chain was also found to have an effect of the biological activity of these compounds, therefore n in Formula II is preferably two or more, and more preferably n equals to 2, 3, 4 or 5.

As is shown in the Examples section that follows, it has further been found that acidic derivatives of a 3,3-dimethyl-butyl are highly efficacious and are therefore preferred.

Particularly efficacious compounds were found to have a 3,3-dimethyl-butyramide as $R_1$.

Preferred amide derivatives of the carboxylic moiety in $R_1$ in general and 3,3-dimethyl-butyramides in particular, include amides of a corresponding acid and substituted amines such as, for example, dialkylamines, morpholino, piperazine, and amino acid residues.

Amino acid residues form an amide (e.g., a 3,3-dimethyl-butyramide) with a corresponding acid (e.g., butyric acid) via the amino-end thereof. Amides of amino acid residues may include one or more amino acid residues, preferably 1-4 amino acid residues, being linked to one another so as to form a short peptide that forms an amide bond with the acid. The amino acid residues can be residues of naturally occurring amino acids and/or modified amino acids, and includes residues of both D- and L-amino acids. Exemplary amino acid residues that have been successfully utilized to form a butyramide as the $R_1$ substituent include glycine and proline.

Exemplary preferred $R_1$ substituents, according to the present embodiments, include, without limitation, butyric acid, butyric acid ethyl ester, N-methoxy-N-methyl-butyramide, N,N-diethyl-butyramide, 3,3-dimethyl-butyric acid, 3,3-dimethyl-butyric acid ethyl ester, N-hydroxy-3,3-dimethyl-butyramide, 3,3-dimethyl-butyric acid 4-oxo-4H-benzo[d][1,2,3]triazin-3-yl ester, N,N-diethyl-3,3-dimethyl-butyramide, N-(2-dimethylamino-ethyl)-3,3-dimethyl-butyramide, N-(3-dimethylamino-propyl)-3,3-dimethyl-butyramide, 3,3-dimethyl-1-(4-methyl-piperazin-1-yl)-butan-1-one, 3,3-dimethyl-1-morpholin-4-yl-butan-1-one, (3,3-dimethyl-butyrylamino)-acetic acid, (3,3-dimethyl-butyrylamino)-acetic acid tert-butyl ester, [(3,3-dimethyl-butyryl)-methyl-amino]-acetic acid, [(3,3-dimethyl-butyryl)-methyl-amino]-acetic acid methyl ester, 1-(3,3-dimethyl-butyryl)-pyrrolidine-2-carboxylic acid, N,N-diethyl-2-(1-methyl-cyclohexyl)-acetamide, propyl-phosphonic acid diethyl ester and 1-methoxy-propane.

Alternatively, $R_1$ can be an unsubstituted phenyl, a phenyl substituted at the meta position by an electron-withdrawing group (e.g., halo, trihalomethyl and nitro), or an alkyl, preferably substituted by an alkoxy group. Preferred compounds are those in which $R_1$ is phenyl, 3-halophenyl, 3-trihalomethylphenyl or 3-nitrophenyl.

Further alternatively, $R_1$ can be a substituted or unsubstituted heteroaryl. Preferred compounds are those in which $R_1$ is tetrahydro-thiophene-3-yl-1,1-dioxide or 1,5-dimethyl-2-phenyl-1,2-dihydro-pyrazolyl-3-one.

As stated hereinabove, the rigidified compounds presented herein have a rhodanine-like residue attached to an aryl or a heteroaryl residue, which is optionally further attached to another aryl or heteroaryl residue. The rigid core structure(s) in these compounds can comprise either the rhodanine-like residue and the first aryl or heteroaryl residue and/or the two aryl or heteroaryl residues, whereby the rigidification is effected by one or more linking moieties that connect two or more radicals in these structures.

The phrase "linking moiety", as used herein, refers to a chemical moiety which connects two or more radicals in a compound. The linking moiety, according to the present embodiments, is selected such that by connecting these radicals, the rotatability of one or more bonds in the compounds is restricted and thus the number of free-to-rotate bonds in the compound is reduced. The number of linking moieties in any given rigidified compound presented herein may vary from one to five, depending on the desired degree of rigidification.

The linking moiety or moieties can be selected, for example, from a covalent bond, including, for example, a single bond, a double bond or a triple bond, and a bridging moiety that comprises one or more additional atoms and which bridges between the two radicals and is preferably a single bond.

The term "radical", as used herein, refers to an atom or a chemical group which forms a part of a compound, and which shares one or more electrons with another atom or chemical group. Non-limiting examples include, a —NR— group, which is linked, for example, to another —NR— group, to a —CR$_2$— group or to a —C(=O)— group, to thereby form a —N—N— bond, a —N—C— bond or an amide bond, respectively; an —O— or —S— atom, deriving, for example from a hydroxy or thiohydroxy group, respectively, which is linked to a —CR$_2$— group or to a —NR— group, to thereby form a —O—C— bond or a —S—C— bond, or a O—N— bond or —S—O— bond, respectively; and so on, where R herein generally represents any compatible to substituent.

The term "radical" as used herein refers an atom or a chemical group which shares one or more electrons with another atom or chemical group, and which is derived or stems from a corresponding atom or a chemical group in a corresponding pre-rigidified. Thus, the term "radical" is interchangeably presented herein as a radical that is derived or stems from such an atom or a chemical group. For example, —O— or —S— radicals can stem from a hydroxy or thiohydroxy groups, respectively, in a corresponding pre-rigidified compound; a —NR— radical can stem from a free amine group or from an amine that forms a part of a heterocyclic ring structure in a corresponding pre-rigidified compound; a —CR$_2$— radical can stem from an alkyl group, being a substituent or forming a part of a ring structure.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine, as these terms are defined hereinbelow.

The term "alkenyl" refers to an alkyl group which consists of at least two carbon atoms and at least one carbon-carbon double bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine.

As used herein, the term "amine" describes a —NR'R" group wherein R' and R" are each independently hydrogen, alkyl, cycloalkyl, aryl, as these terms are defined hereinabove. The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine.

The term "halo", which is also referred to herein as "halide", describes fluorine, chlorine, bromine or iodine.

The term "sulfonate" describes a —S(=O)$_2$—R' where R' is as defined herein.

The term "sulfoxide" or "sulfinyl" describes a —S(=O)R' where R' is as defined hereinabove.

The term "phosphonate" describes a —P(=O)(OR')(OR") with R' and R" as defined herein.

The term "phosphonamide" describes a —P(=O)(NR')(NR") with R' and R" as defined herein.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy", which is also referred to as "thiol" or "mercapto", describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "nitro" describes an —NO$_2$ group.

The term "azo" or "diazo" describes an —N=NR' with R' as defined hereinabove.

The term "S-sulfonamide" and "sulfonamide" describes a —S(=O)$_2$—NR'R" group or a —S(=O)$_2$—NR'— group with R' and R" as defined herein.

The term "N-sulfonamide" describes an R'S(=O)$_2$—NR"— group or a —S(=O)$_2$—NR'— group where R' and R" are as defined herein.

The term "carbonyl" or "carbonate" as used herein, describes a —C(=O)—R' group or a —C(=O)— group, with R' as defined herein.

The term "C-carboxylate" describes a —C(=O)—OR' group, where R' is as defined herein.

The term "O-carboxylate" describes a —OC(=O)R' where R' is as defined herein.

The term "O-thiocarbamate" describes a OC(=S)—NR'R" with R' and R" as defined herein.

The term "N-thiocarbamate" describes an R"OC(=S)NR'— with R' and R" as defined herein.

The term "urea", which is also referred to herein as "ureido", describes an NR'C(=O)—NR"R''' group or a NR'C(=O)—NR"— group, where R' and R" are as defined herein and R''' is as defined herein for R' and R".

The term "thiourea", which is also referred to herein as "thioureido", describes a —NR'—C(=S)—NR"R''' group or a —NR'—C(=S)—NR"— group, with R', R" and R''' as defined herein.

The term "N-carbamate" describes an R"OC(=O)—NR' group or a OC(=O)—NR'— group with R' and R" as defined herein.

The term "O-carbamate" describes an —OC(=O)—NR'R" group or an —OC(=O)—NR'— group with R' and R" as defined herein.

The term "C-amide" describes a —C(=O)—NR'R" group or a —C(=O)—NR'— group where R' and R" are as defined herein.

The term "N-amide" describes a R'C(=O)—NR"— group or a R'C(=O)—N— group where R' and R" are as defined herein.

The term "guanyl" describes a R'R"NC(=N)— group or a —R'NC(=N)— group where R' and R" are as defined herein.

The term "guanidine" describes a —R'NC(=N)—NR"R'" end group or a —R'NC(=N)—NR"— group where R', R" and R'" are as defined herein.

The term "hydrazine" describes a —NR'—NR"R'" group or a —NR'—NR"— group with R', R", and R'" as defined herein.

The term "borate" describes a —O—B(OR')(OR") group or a —O—B(OR')(O—) group with R' and R" are as defined herein.

The term "silyl" describes a —SiR'R" group whereby each of R' and R" are as defined herein.

As mentioned above, the rhodanine or rhodanine analog residue of the rigidified compound presented herein is covalently attached to an aryl or a heteroaryl residue. This aryl or heteroaryl residue is referred to herein as a first aryl or heteroaryl residue. In cases where the compound comprises a heteroaryl residue, such a residue in a corresponding pre-rigidified compound can adapt two optional conformations with respect to the rhodanine-like residue, which stem from a free to rotate bond that links the heteroaryl residue to the rhodanine residue.

Preferred first aryl or heteroaryl residues according to the present embodiments can be therefore represented by the following general Formula III:

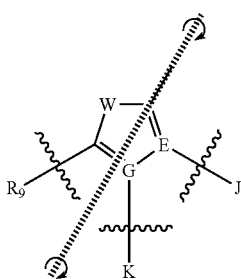

Formula III whereas the wavy lines indicates a part of the aryl or heteroaryl residue which is included in the core structure, in cases where the rigidified compound has the core structure I;

W is O, S, NRd, CRdRe or RdC=CRe;

E and G are each independently N or CRs;

J and K are each independently a lone pair of electrons in cases where E and/or G are N); or J and K are each independently ORi (e.g., alkoxy), SRi (e.g., thioalkoxy), NRiRj (e.g., amine), CRiRjRk, hydrogen, alkyl, hydroxy, thiohydroxy, alkoxy, thioalkoxy, halo, nitro, trihaloalkyl, C-carboxylate, O-carboxylate, C-amide, N-amide, S-sulfonamide, N-sulfonamide or absent, or, alternatively, J and K form a five- or six-membered ring (in cases where E and/or G are CRs and J and K represent, each independently the Rs substituent);

Rd, Re, Ri, Rj, Rk and Rs are each independently hydrogen, a substituted or unsubstituted alkyl, a substituted or unsubstituted cycloalkyl, and a substituted or unsubstituted aryl; and $R_9$ is selected from the group consisting of hydrogen, a substituted or unsubstituted alkyl, a substituted or unsubstituted cycloalkyl, a substituted or unsubstituted aryl and a substituted or unsubstituted heteroaryl, or, alternatively, at least two of E, G and $R_9$ form a 5- or 6-membered ring, and further whereas each of the substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide.

The non-substituted bond in Formula III denotes that bond correcting the aryl or heteroaryl residue to the rhodanine-like residue.

The hashed line and round arrows in Formula III indicate an axis of 180 degrees rotation of the aryl or heteroaryl residue along the bond connecting the aryl or heteroaryl residue to the rhodanine-like residue. Preferred aryl or heteroaryl residues in this context of the present invention can be therefore represented by Formulae IIIa and IIIb as follows:

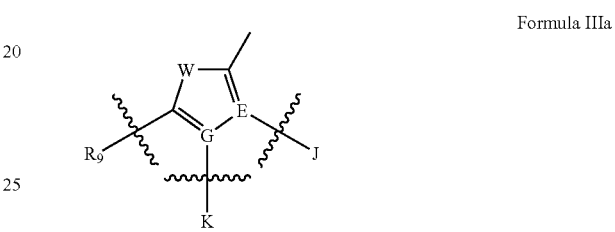

Formula IIIa

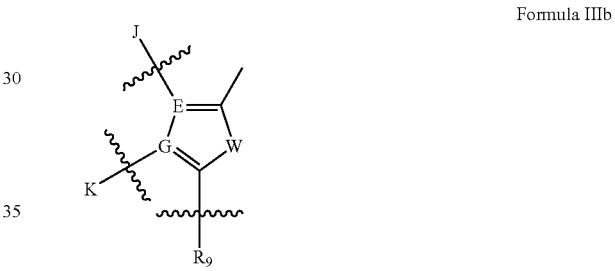

Formula IIIb

Alternatively, preferred aryl or heteroaryl residues according to the present embodiments can be represented by the following general Formula III*:

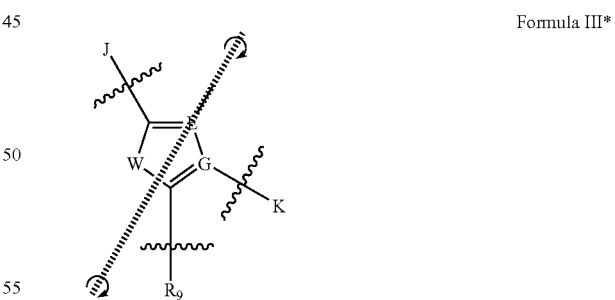

Formula III*

In Formula III*, the aryl or heteroaryl residue is linked to the rhodanine-like residue via a position different than that presented in Formula III above.

The hashed line and round arrows in Formula III indicate an axis of 180 degrees rotation of the heteroaryl residue along the bond connecting the heteroaryl residue to the rhodamine-like residue. Preferred heteroaryl residues in this context of the present invention can be therefore represented by Formulae IIIc and IIId as follows:

Formula IIIc

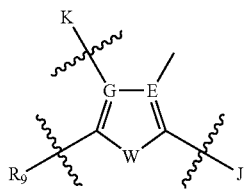

Formula IIId

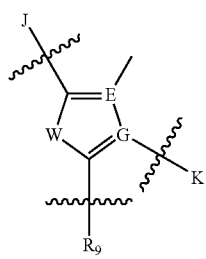

Preferably, W is O or S, such that the first aryl or heteroaryl residue is a heteroaryl. Further preferably, E and G are both CRs, such that the heteroaryl residue is derived from a furan or a thiophene residue.

According to preferred embodiments of the present invention, $R_9$ is a second aryl or heteroaryl residue. As taught in U.S. patent application Ser. No. 10/916,598, preferred compounds are those having a hydrophobic substituent at this position of the first aryl or heteroaryl and hence, preferably $R_9$ is aryl.

Further preferably, $R_9$ is an aryl having the general Formula IV:

Formula IV

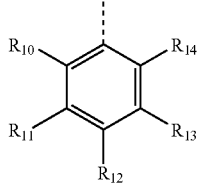

wherein each of $R_{10}$-$R_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of $R_{10}$-$R_{14}$ form a five- or six-membered ring.

This second aryl residue in a pre-rigidified compound can adapt two optional conformations with respect to the first aryl or heteroaryl residue, which stem from a free-to-rotate bond that links the two residues.

Thus, such a second aryl residue can be represented by Formula IV*:

Formula IV*

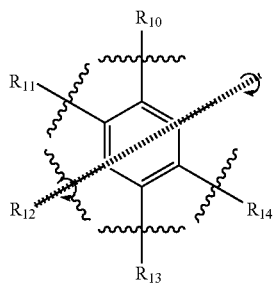

The wavy lines indicate the part of the aryl residue that is included in the core structure, in cases where the rigidified compound comprises the core structure II.

The hashed line and round arrows in Formula IV* indicate an axis of 180 degrees rotation of the aryl along the bond connecting it to the first heteroaryl residue which is connected to the rhodamine-like residue. Preferred aryls in this context of the present invention can be therefore represented by Formulae IVa and IVb as follows:

Formula IVa

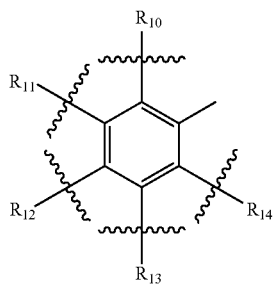

Formula IVb

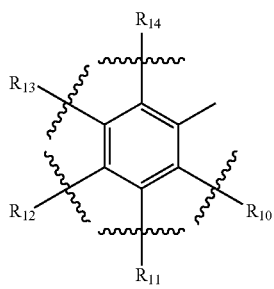

In further preferred embodiments of the present invention, $R_{10}$ and $R_{14}$ are each independently selected from the group consisting of hydrogen, alkyl, cycloalkyl, hydroxy, alkoxy, thiohydroxy, thioalkoxy, aryloxy and thioaryloxy; and $R_{11}$-$R_{13}$ are each independently selected from the group consisting of hydrogen, halo, nitro, trihaloalkyl and C-carboxylate.

Specifically, an electron-withdrawing substituent such as, for example, Cl, Br or $NO_2$ in the meta or para position of the second aryl/heteroaryl residue is preferred. In contrast, electron-withdrawing substituents in ortho positions are less favorable.

Alternatively, $R_9$ can be a substituted or unsubstituted benzothiazole.

According to preferred embodiments of the present invention, the rigidified compound presented herein has a core structure I, which includes the rhodanine or rhodanine analog residue being covalently attached to the first aryl or heteroaryl residue, as described hereinabove. Core structure I can therefore be represented by the following general Formula Va or Vb:

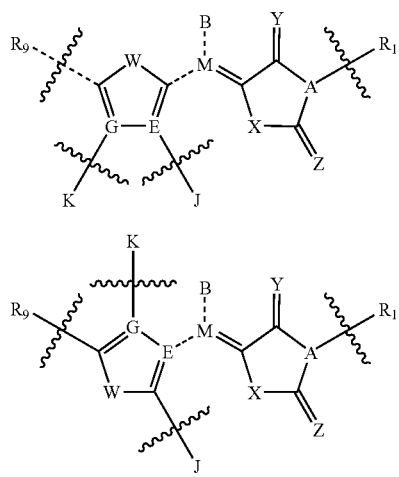

Formula Va

Formula Vb wherein the wavy lines indicate those parts of the rhodanine or rhodanine analog residue and of the aryl or heteroaryl residue which are included in the core structure; and the dashed lines indicate various conformations of the residues at these positions, as is outlined herein.

Specifically, such a core structure can be represented by the following Formula Va* and Formula Vb*:

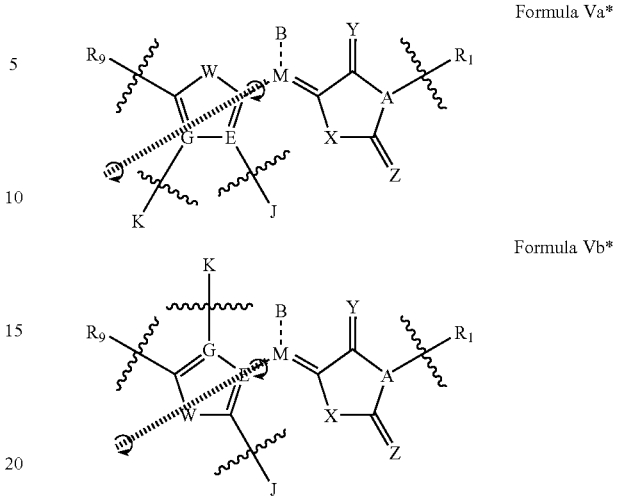

Formula Va*

Formula Vb* wherein the hashed line and round arrows in these formulae indicate an axis of 180 degrees rotation of the first aryl or heteroaryl residue along the bond connecting it to the rhodanine-like residue.

The dual stereoisomerism involving the Z- and E-configurations in the rhodanine/rhodanine analog residue, and the dual configuration of the first aryl or heteroaryl attached thereto constitute eight sub-formulae of the rigidified compounds presented herein, as depicted in the following schemes:

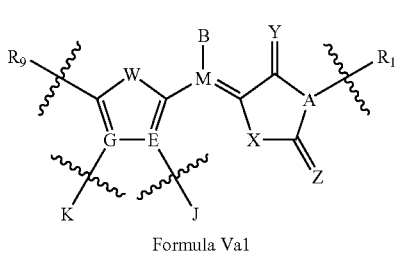

Formula Va1

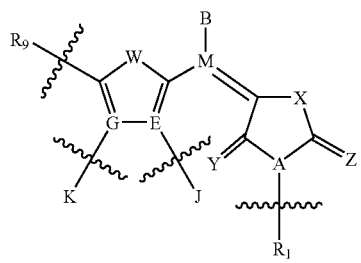

Formula Va2

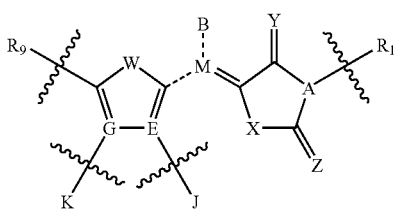

Formula Va

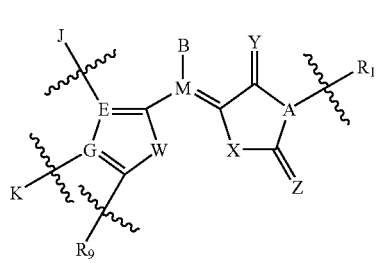
Formula Va3
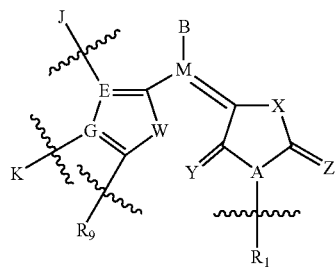
Formula Va4
and
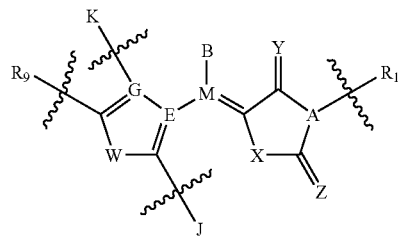
Formula Vb1
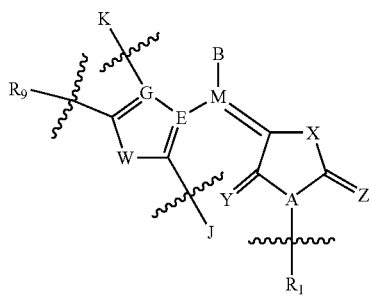
Formula Vb2
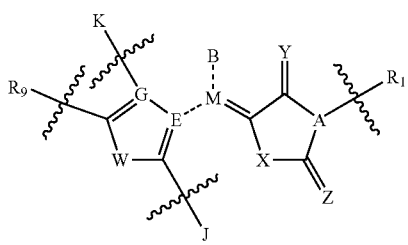
Formula Vb
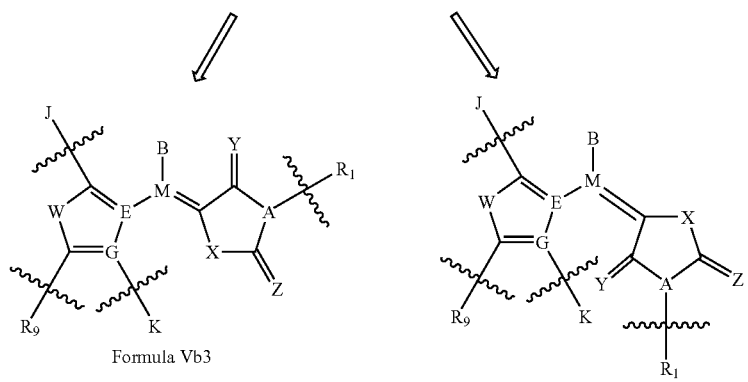
Formula Vb3
Formula Vb4

Each formula in the above schemes represents an embodiment of the rigidified compounds presented herein wherein the wavy lines indicate those parts of the rhodanine or rhodanine analog residue and of the first aryl or heteroaryl residue which are included in the core structure I.

In each of the optional core structures I presented herein, each of A, X, Y, Z, W, M, B, E, G, J, K, $R_1$ and $R_9$ are as defined hereinabove.

Preferably, $R_9$ is a substituted aryl or heteroaryl and more preferably, it is an aryl having Formula IV as described hereinabove wherein $R_{10}$-$R_{14}$ are as defined hereinabove.

More importantly, each of the optional core structures I presented herein by Formulae Va and Vb, and each of the sub-formulae thereof, further comprises one or more linking moieties connecting at least two radicals of A, B, E, G, J, K, X, Y and/or W, as is detailed hereinunder.

According to further embodiments of the present invention, the rigidified compound has core structure II. Such compounds can be comprised of a first and a second aryl or heteroaryl residues whereby each of these residues can be independently represented by Formulae III and IV hereinabove. Preferably, the first aryl or heteroaryl residue has the Formula III presented above and the second aryl or heteroaryl residue has the formula IV presented hereinabove, such that preferred compounds having core structure II can be collectively represented by the following Formulae VIa and VIb:

Formula VIa

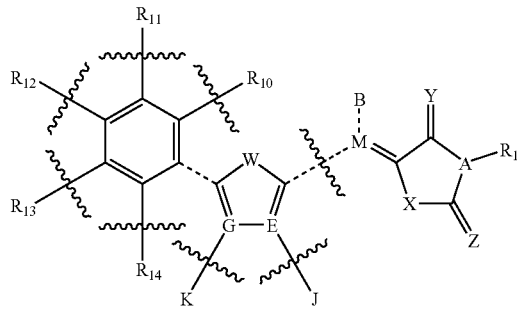

Formula VIb

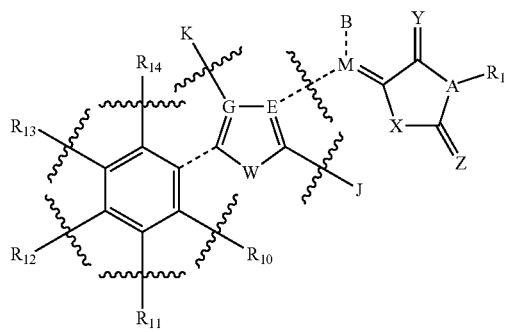

wherein the wavy lines indicate those parts of the first and second aryl or heteroaryl residues which are included in the core structure II, and the dashed lines indicate various conformations of the residues at these positions, as is outlined herein;

and A, X, Y, Z, W, M, B, E, G, J, K, $R_1$, $R_{10}$-$R_{14}$ are as defined hereinabove;

and further wherein the core structure further comprises at least one linking moiety connecting at least two radicals of W, E, G, J, K and/or $R_{10}$-$R_{14}$.

Specifically, such a core structure can be represented by the following Formula VIa* and Formula VIb**:

Formula VIa*

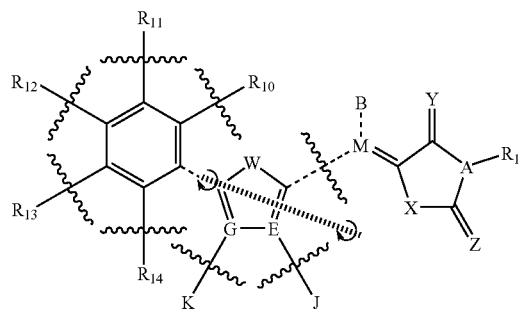

Formula VIb*

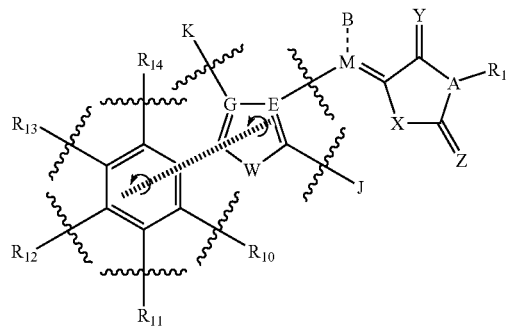

wherein the hashed line and round arrows indicate an axis of 180 degrees rotation of the second aryl or heteroaryl residue along the bond it to the first aryl or heteroaryl residue.

As in the embodiments presented above, the same dual stereoisomerism involving the configurations of the first aryl/heteroaryl attached to the rhodanine-like residue, and the dual configuration between the first and second aryl or heteroaryl residues also constitute four sub-formulae of the core structure of the rigidified compounds presented herein, as depicted in the following scheme:

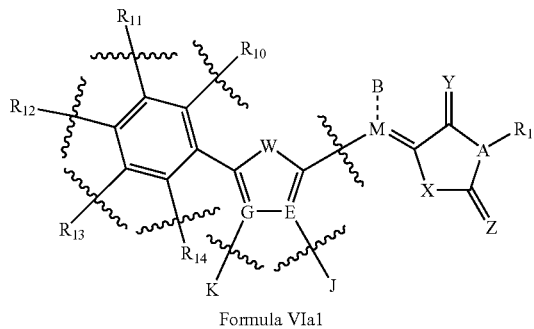

Formula VIa1

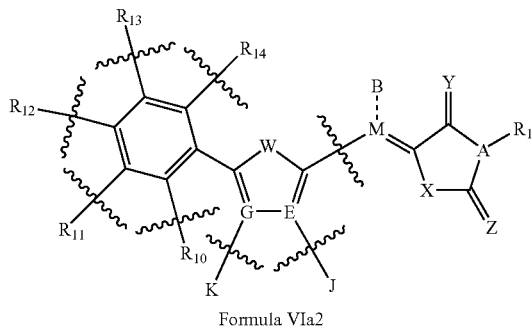

Formula VIa2

Formula VI

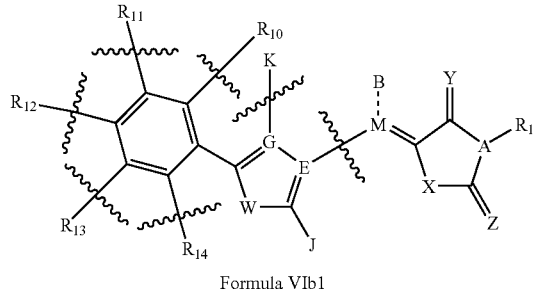

Formula VIb1

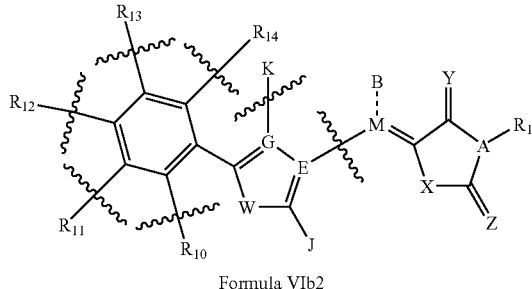

Formula VIb2

Each formula in the above scheme represents an embodiment of the rigidified compounds presented herein wherein the wavy lines indicates those parts of the first aryl or heteroaryl and the second aryl or heteroaryl residue which are included in the core structure II.

More importantly, each of the optional core structures II presented herein by Formulae VIa, VIb and the subformulae thereof, further comprises one or more linking moieties connecting at least two radicals of W, G, E, J, K and/or $R_{10}$-$R_{14}$, as is detailed hereunder.

The structures presented in the various formulae hereinabove generally present rigidified compounds according to the present embodiments which may include core structure I and/or II, each having one or zero free-to-rotate bond, and in which the number of free-to-rotate bonds is reduced as compared with a corresponding non-rigidified compound due to the presence of a linking moiety that connects two or more radicals in the core structure and thus converts a free-to-rotate bond to a conformationally-restricted bond.

There is a great number of models by which the compounds presented herein can be rigidified according to any of the abovementioned embodiments, each depending on the absolute configuration between the residues which form a part of the compound, the type and number of the linking moieties and the radicals being connected.

Table 1 below presents several representative exemplary and non-limiting rigidification models, or plausible rigidification strategies. The optional linking moieties in each rigidification strategy are represented by bold bond-lines.

TABLE 1
| | |
|---|---|
| Rigidification Strategy 1 | 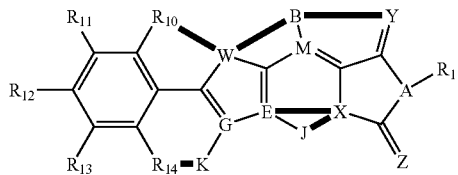 |
| Rigidification Strategy 2 | 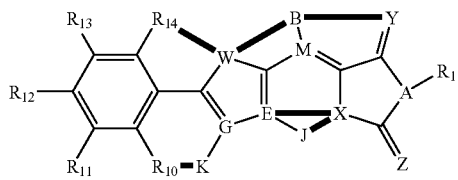 |
| Rigidification Strategy 3 | 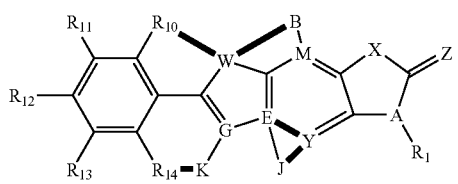 |
| Rigidification Strategy 4 | 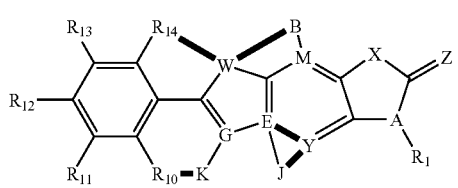 |
| Rigidification Strategy 5 | 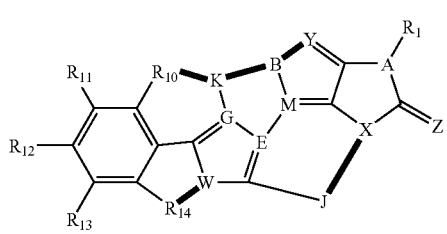 |
| Rigidification Strategy 6 | 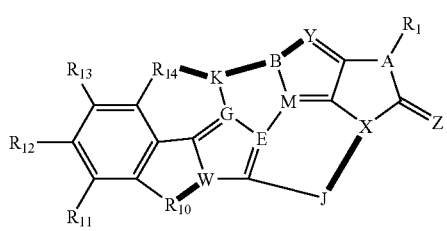 |
| Rigidification Strategy 7 | 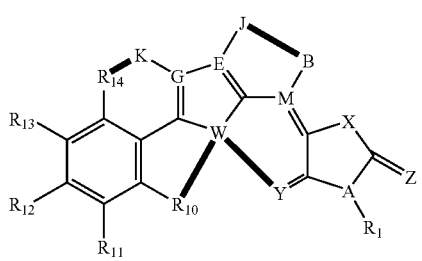 |

TABLE 1-continued

Rigidification Strategy 8

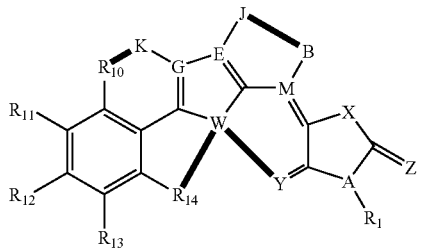

Rigidification Strategy 9

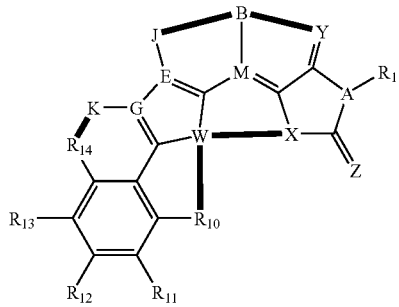

Rigidification Strategy 10

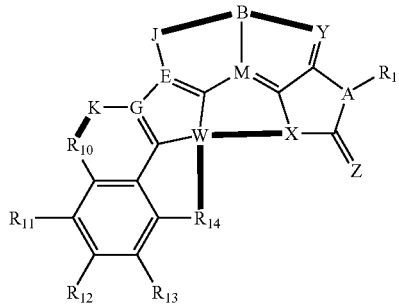

Each of the above rigidification strategies may have one or more of the linking moieties connecting various radicals therein as depicted in Table 1 above.

Following are non-limiting exemplary rigidification possibilities, pertaining to core structure I.

In an embodiment of the present invention, the rigidified compound presented herein may have one of the linking moieties connecting the radicals which stem from B and Y. In one particular, non-limiting, example B is hydroxy and Y is NRd, and the rigidification results in a —O—N— bond linking radicals of B and Y. In another non-limiting example B is thiohydroxy and Y is NRd, and the rigidification results in a —S—N— bond linking radicals of B and Y. Such a rigidification is depicted in Rigidification Scheme I below wherein the linking moieties in marked in a bold line. An exemplary compound in this category is Compound 45 (see, the Examples section that follows).

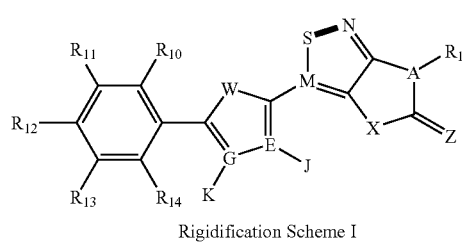

Rigidification Scheme I

As shown in Rigidification Scheme I, in core structure I, the free rotation of the bond connecting M to the rhodanine ring, which may enable a conformational change between an E-configuration and a Z-configuration of the rhodanine-like residue, is eliminated by the rigidification. The bond connecting the first aryl or heteroaryl residue and the rhodanine-like residue may exhibit a 180 degrees rotation, as delineated hereinabove, and constitutes the single free-to-rotate bond in the core structure.

In another embodiment, the rigidified compound presented herein may have one of the linking moieties connecting the radicals which stem from W and X. In one particular, non-limiting, example W is NRd and X is NRb, and the rigidification results in a —N—N— bond linking radicals of W and X. Such a rigidified compound is depicted in Rigidification Scheme II below wherein the linking moieties in marked in a bold line.

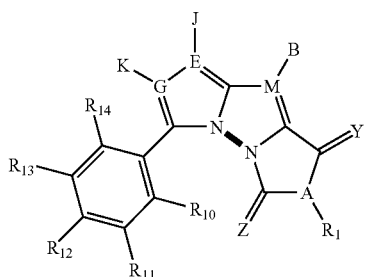

Rigidification Scheme II

As shown in Rigidification Scheme II, in core structure I, the free rotation of the bond connecting M to the rhodanine ring, which may enable a conformational change between an E-configuration and a Z-configuration of the rhodanine-like residue, as well as the free rotation of the bond connecting the first aryl or heteroaryl residue and the rhodanine-like residue, which may enable a 180 degrees rotation, as delineated hereinabove, have both been eliminated by the rigidification, resulting in zero free-to-rotate bonds in the core structure.

In yet another embodiment, the rigidified compound may have one of the linking moieties connecting the radicals which stem from W and Y. In one particular, non-limiting, example each of W and Y are each independently NRd, resulting in a —N—N— bond linking radicals of W and Y, as depicted in Rigidification Scheme III below wherein the linking moieties in marked in a bold line.

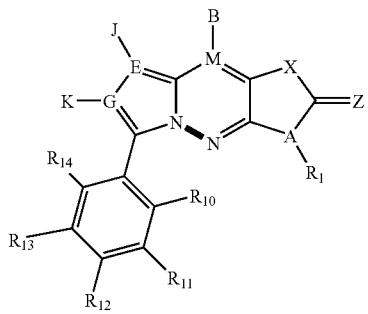

Rigidification Scheme III

As shown in Rigidification Scheme III, in core structure I, the free rotation of the bond connecting M to the rhodanine ring, which may enable a conformational change between an E-configuration and a Z-configuration of the rhodanine-like residue, as well as the free rotation of the bond connecting the first aryl or heteroaryl residue and the rhodanine-like residue, which may enable a 180 degrees rotation, as delineated hereinabove, have both been eliminated by the rigidification, resulting in zero free-to-rotate bonds in the core structure.

In yet another embodiment, the rigidified compound may have one of the linking moieties connecting the radicals which stem from E and X. In one particular, non-limiting, example X is NRb and E is CRs, and the rigidification results in a —C—N— bond linking radicals of E and X, as depicted in Rigidification Scheme IV below wherein the linking moieties in marked in a bold line. Exemplary compounds in this category are Compounds 1-32 (see, the Examples section that follows).

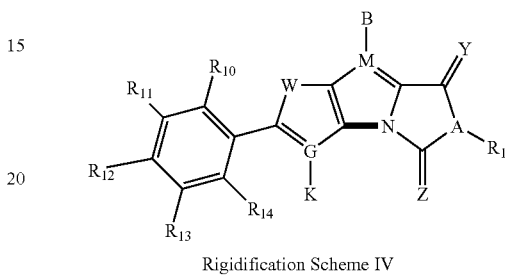

Rigidification Scheme IV

As shown in Rigidification Scheme IV, in core structure I, the free rotation of the bond connecting M to the rhodanine ring, which may enable a conformational change between an E-configuration and a Z-configuration of the rhodanine-like residue, as well as the free rotation of the bond connecting the first aryl or heteroaryl residue and the rhodanine-like residue, which may enable a 180 degrees rotation, as delineated hereinabove, have both been eliminated by the rigidification, resulting in zero free-to-rotate bonds in the core structure.

In yet another embodiment, the rigidified compound may have one of the linking moieties connecting the radicals which stem from J and X. In one particular, non-limiting, example J is C=O and X is NRb and E is CRs, and the rigidification results in a —C(=O)—N— bond linking radicals of J and X, as depicted in Rigidification Scheme V below wherein the linking moieties in marked in a bold line. An exemplary compound in this category is Compounds 48 (see, the Examples section that follows).

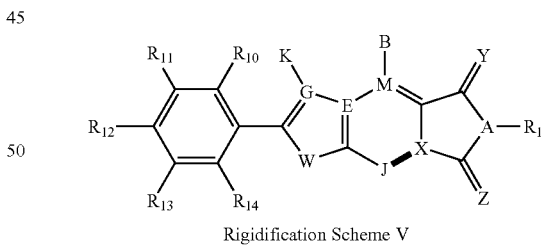

Rigidification Scheme V

As shown in Rigidification Scheme V, in core structure I, the free rotation of the bond connecting M to the rhodanine ring, which may enable a conformational change between an E-configuration and a Z-configuration of the rhodanine-like residue, as well as the free rotation of the bond connecting the first aryl or heteroaryl residue and the rhodanine-like residue, which may enable a 180 degrees rotation, as delineated hereinabove, have both been eliminated by the rigidification, resulting in zero free-to-rotate bonds in the core structure.

In still another embodiment, the rigidified compound may have one of the linking moieties connecting the radicals which stem from J and Y. In one particular, non-limiting, example J is thiohydroxy and Y is NRd, and the rigidification results in a —S—N— bond linking radicals of J and Y, as depicted in Rigidification Scheme VI below wherein the linking moieties in marked in a bold line.

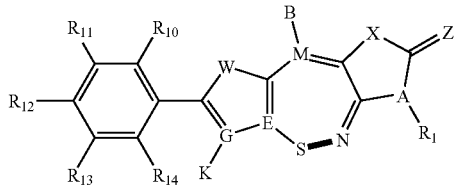

Rigidification Scheme VI

As shown in Rigidification Scheme VI, in core structure I, the free rotation of the bond connecting M to the rhodanine ring, which may enable a conformational change between an E-configuration and a Z-configuration of the rhodanine-like residue, as well as the free rotation of the bond connecting the first aryl or heteroaryl residue and the rhodanine-like residue, which may enable a 180 degrees rotation, as delineated hereinabove, have both been eliminated by the rigidification, resulting in zero free-to-rotate bonds in the core structure.

In another embodiment, the rigidified compound may have one of the linking moieties connecting the radicals which stem from J and B. In one particular, non-limiting, example J is CRiRjRk or NRiRj and B is a thiohydroxy, and the rigidification results in a —C—S— bond or a —N—S— bond, respectively, linking radicals of J and B, as depicted in Rigidification Scheme VII below wherein the linking moieties in marked in a bold line.

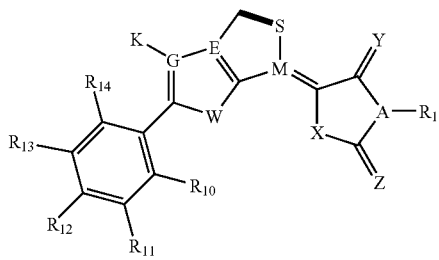

Rigidification Scheme VII

As shown in Rigidification Scheme VII, in core structure I, the free rotation of the bond connecting the first aryl or heteroaryl residue and the rhodanine-like residue, which may enable a 180 degrees rotation, as delineated hereinabove, has been eliminated. The free rotation of the bond connecting M to the rhodanine ring, which may enable a conformational change between an E-configuration and a Z-configuration of the rhodanine-like residue, constitutes the single free-to-rotate bond in the core structure.

In still another embodiment, the rigidified compound may have one of the linking moieties connecting the radicals which stem from W and B. In one particular, non-limiting, example W is NRd and B is methyl, and the rigidification results in a —N—C— bond linking radicals of W and B, as depicted in Rigidification Scheme VIII below wherein the linking moieties in marked in a bold line.

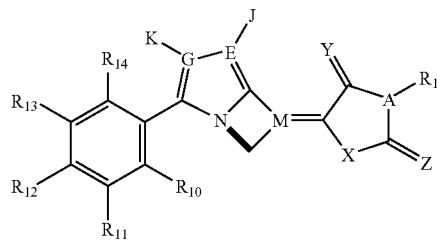

Rigidification Scheme VIII

As shown in Rigidification Scheme VIII, in core structure I, the free rotation of the bond connecting the first aryl or heteroaryl residue and the rhodanine-like residue, which may enable a 180 degrees rotation, as delineated hereinabove, has been eliminated. The free rotation of the bond connecting M to the rhodanine ring, which may enable a conformational change between an E-configuration and a Z-configuration of the rhodanine-like residue, constitutes the single free-to-rotate bond in the core structure.

In still another embodiment, the rigidified compound may have one of the linking moieties connecting the radicals which stem from B and Y and another linking moiety connecting the radicals which stem from E and X. In one particular, non-limiting, example B is hydroxy; Y is NRd; X is NRb and E is CRs, and the rigidification results in a —O—N— bond linking radicals of B and Y, and a —C—N— bond linking radicals of X and E. In another non-limiting example B is thiohydroxy; Y is NRd; X is NRb and E is CRs, and the rigidification results in a —S—N— bond linking radicals of B and Y, and a —C—N— bond linking radicals of X and E, as depicted in Rigidification Scheme IX below wherein the linking moieties in marked in a bold line. An exemplary compound in this category is Compound 46 (see, the Examples section that follows).

Rigidification Scheme IX

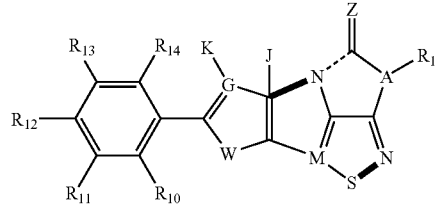

As shown in Rigidification Scheme IX, in core structure I, the free rotation of the bond connecting M to the rhodanine ring, which may enable a conformational change between an E-configuration and a Z-configuration of the rhodanine-like residue, as well as the free rotation of the bond connecting the first aryl or heteroaryl residue and the rhodanine-like residue, which may enable a 180 degrees rotation, as delineated hereinabove, have both been eliminated by the rigidification, resulting in zero free-to-rotate bonds in the core structure.

In still another embodiment, the rigidified compound may have one of the linking moieties connecting the radicals which stem from B and Y and another linking moiety connecting the radicals which stem from W and X. In one particular, non-limiting, example B is hydroxy, thiohydroxy or amine; Y is NRd; W is NRd; and X is NRb, and the rigidification results in a —O—N—, —S—N— or a —N—N— bond linking radicals of B and Y, and a —N—N— bond linking radicals of X and E, as depicted in Rigidification Scheme X below wherein the linking moieties in marked in a bold line.

Rigidification Scheme X

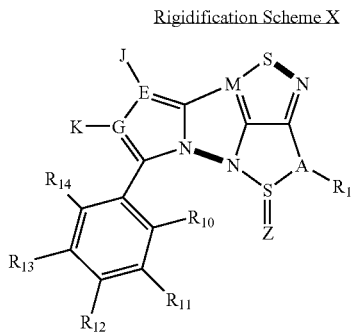

As shown in Rigidification Scheme X, in core structure I, the free rotation of the bond connecting M to the rhodanine ring, which may enable a conformational change between an E-configuration and a Z-configuration of the rhodanine-like residue, as well as the free rotation of the bond connecting the first aryl or heteroaryl residue and the rhodanine-like residue, which may enable a 180 degrees rotation, as delineated hereinabove, have both been eliminated by the rigidification, resulting in zero free-to-rotate bonds in the core structure.

In still another embodiment, the rigidified compound may have one of the linking moieties connecting the radicals which stem from E and Y. In one particular, non-limiting, example E is CRs and Y is NRd, and the rigidification results in a —C—N— bond linking radicals of E and Y, as depicted in Rigidification Scheme XI below wherein the linking moieties in marked in a bold line. An exemplary compound in this category is Compound 47 (see, the Examples section that follows).

Rigidification Scheme XI

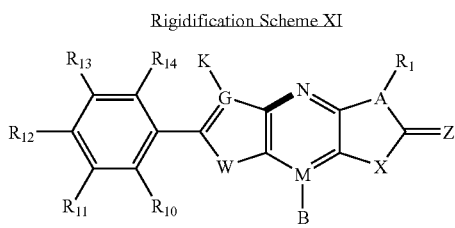

As shown in Rigidification Scheme XI, in core structure I, the free rotation of the bond connecting M to the rhodanine ring, which may enable a conformational change between an E-configuration and a Z-configuration of the rhodanine-like residue, as well as the free rotation of the bond connecting the first aryl or heteroaryl residue and the rhodanine-like residue, which may enable a 180 degrees rotation, as delineated hereinabove, have both been eliminated by the rigidification, resulting in zero free-to-rotate bonds in the core structure.

Following are non-limiting exemplary rigidified compounds having core structure II.

In one embodiment, the rigidified compound may have one of the linking moieties connecting the radicals which stem from $R_{14}$ and K and another linking moiety connecting the radicals which stem from W and $R_{10}$. In one particular, non-limiting, example $R_{14}$ is alkoxy or hydroxy, K is CRiRjRk, W is NRd and $R_{10}$ is alkoxy or hydroxy, and the rigidification results in a —O—N— bond linking radicals of $R_{10}$ and K, and a —O—C— bond linking radicals of W and $R_{14}$, as depicted in Rigidification Scheme XII below wherein the linking moieties in marked in a bold Rigidification Scheme XII

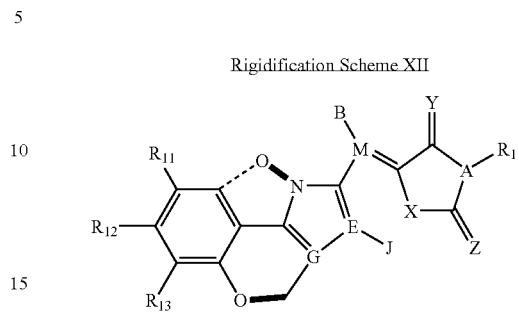

As shown in Rigidification Scheme XII, in core structure II, the free rotation of the bond connecting the first and the second aryl or heteroaryl residue has been completely eliminated by the rigidification. The free rotation of the first aryl or heteroaryl residue constitutes a single free-to-rotate bond in the core structure.

In another embodiment, the rigidified compound may have one of the linking moieties connecting the radicals which stem from $R_{14}$ and W, another linking moiety connecting the radicals which stem from K and $R_{10}$, and another linking moiety connecting the radicals which stem from J and B. In one particular, non-limiting, example $R_{14}$ is alkyl, $R_{10}$ is alkoxy or hydroxy; W is NRd; and J and K are each CNRiRjRk, and the rigidification results in a —O—C— bond linking radicals of $R_{10}$ and K, a —C—N— bond linking radicals of W and $R_{14}$, and a —C—S— bond linking radicals of J and B, as depicted in Rigidification Scheme XIII below wherein the linking moieties in marked in a bold line.

Rigidification Scheme XII

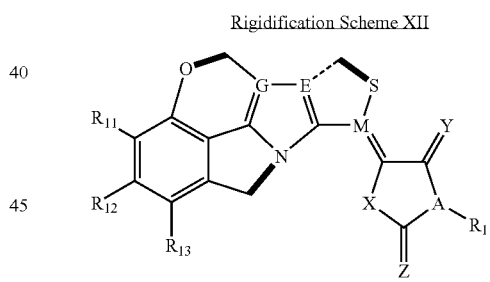

As mentioned above, while reducing the present invention to practice, the present inventors have designed and successfully prepared various rigidified compounds, as demonstrated and exemplified in the Examples section that follows, some of which are set forth and presented in Table 2 hereinbelow.

It will be appreciated by one of skills in the art that the feasibility of each of the substituents (R, R', R", Ra, Rb, Rc, . . . etc., and $R_1$, $R_2$, . . . etc.) in each of the formulae described herein to be located at the indicated positions depends on the valency and chemical compatibility of the substituent, the substituted position and other substituents. Hence, the present invention is aimed at encompassing all the feasible substituents for any position.

It will be appreciated by one of skills in the alt that the feasibility of each of the radicals of A, B, E, G, J, K, X, Y, W, and/or $R_{10}$-$R_{14}$ in each of the formulae described herein to be located at the indicated positions depends on the valency and chemical compatibility of the radical or the atom or chemical group from which the radical stems. Hence, the present invention is aimed at encompassing all the feasible radicals.

As discussed hereinabove, the rigidified compounds presented herein are designed according to the drug development concepts which are taught in U.S. patent application Ser. No. 10/916,598.

As taught in U.S. patent application Ser. No. 10/916,598, rhodanine-based compounds were found as efficient pro-heparanase binding agents, which are capable of interfering with heparanase activation and thus can be used to modulate and preferably inhibit heparanase activity. Some of these rhodanine-based compounds were further found as efficient modulators of heparin-binding proteins and thus can be used to modulate and preferably inhibit heparin-binding proteins. It was further found that the rhodanine-based compounds taught in U.S. patent application Ser. No. 10/916,598, exhibit their biological activity in the presence and absence of light and hence act via a non light-dependent pathway (unpublished results).

As shown herein, in the Examples section that follows, the rigidified compounds presented herein were found highly efficient pro-heparanase binding agents, and were further found as capable of inhibiting heparin binding proteins. As further shown herein, the rigidified compounds were found to exert various biological activities also in the absence of light, demonstrating a non light-dependent pathway of their activity.

Exemplary heparin binding proteins which inhibition thereof is particularly beneficial are the growth factors β-FGF and VEGF.

Heparan sulfates of the extracellular matrix (ECM) sequester pro-angiogenic growth factors (GFs), such as basic fibroblast growth factor (β-FGF) and vascular endothelial growth factor (VEGF), two heparin-binding growth factors. Heparanase, which is overexpressed in many cancers, promotes angiogenesis by facilitating GF release from the ECM. The rigidified compounds presented herein are capable of inhibiting heparanase activity, and interferes with GF binding to heparan sulfates and heparin.

The rigidified compounds presented herein thus act to inhibit heparanase activation and as such may be used to inhibit any activity of heparanase which requires a preceding step of pro-heparanase activation. The rigidified compounds further act an inhibitors of heparin binding proteins such as the growth factors described hereinabove.

As used herein the phrase "heparanase activation" refers to the process of converting inactive pro-heparanase (H60) to heparanase (H53).

Hence, the rigidified compounds presented herein, by being capable of modulating, and preferably inhibiting, heparanase activity, can be used to treat medical conditions which are associated with regulating, modulating and/or inhibiting heparanase activity, and in the treatment of various ailments and disorders associated with heparanase.

As used herein the phrase "heparanase activity" refers to any known heparanase activity (e.g., heparin or heparan sulfate cleavage activity) or the effect of heparanase on biological processes such as cell migration, extravasation, angiogenesis, wound healing, and smooth muscle cell proliferation as described in details in the art.

The rigidified compounds presented herein, by being capable of inhibiting heparin binding protein, can be further used in the treatment of heparin binding protein-associated diseases or disorders.

Hence, according to another aspect of the present invention there is provided a method of regulating a biological process depending at least in part on heparanase activity, the method comprising inhibiting heparanase activity by any of the rigidified compounds presented herein.

Such biological processes include, for example, cell migration, cell invasion, cell implantation, cell transplantation, cell extravasation, bone formation, cell adhesion, embryo implantation, neurodegenerative disorders, autoimmune diseases, atherosclerosis, viral infections, restenosis, skeletal muscle calcium kinetics, diabetic nephropathy, epidermal differentiation and desquamation, HS-involved metabolic disorders, prion diseases, hair growth, angiogenesis, neovascularization, cancer development, metastases formation, wound healing, inflammation and immune recognition.

According to another aspect of the present invention, there is provided a method of treating a heparanase associated disease or disorder in a subject. The method, according to this aspect of the present invention, is effected by administering to the subject in need thereof a therapeutically effective amount of any of the rigidified compounds presented herein.

According to still another aspect of the present invention, there is provided a method of inhibiting heparanase activation. The method, according to this aspect of the present invention, is effected by contacting an inactive heparanase with any of the rigidified compounds presented herein.

According to still another aspect of the present invention there is provided a method for inhibiting heparin binding protein. The method, according to this aspect of the present invention, is effected by contacting the heparin binding protein with any of the rigidified compounds presented herein.

According to still another aspect of the present invention there is provided a method of treating a heparin binding protein-associated disease or disorder in a subject. The method, according to this aspect of the present invention is effected by administering to the subject a therapeutically effective amount of any of the rigidified compounds described herein.

The various features of each of the methods described herein are taught in U.S. patent application Ser. No. 10/916,598.

While the rigidified compounds presented herein serve as improved agents for interfering with heparanase activity and with heparin binding proteins, these rigidified compounds can further serve as improved agents for treating medical conditions in which compounds having a rhodanine skeleton are known as therapeutically active agents.

As mentioned hereinabove, therapeutically active compounds that have a rhodanine skeleton include, for example, β-lactamase inhibitors (Grant E B, Bioorg. Med. Chem. Lett., 10, 2179, 2000), hepatitis C virus protease inhibitors (Sing W T, Bioorg. Med. Chem. Lett., 11, 91, 2001), aldose reductase inhibitors (Ohishi Y, Chem. Pharm. Bull., 38, 1911, 1990), antifungal agents (Orchard M G, WO 02/022612), sialyl Lewis X synthesis inhibitors (Kobayashi K, JP 11302280), VEGF antagonists (WO 98/53790), phospholipase D (U.S. Ser. No. 04/000,2526) and PIN-1 inhibitors (WO 04/028535).

Thus, according to a further aspect of the present invention there is provided a method of treating a medical condition at least partially treatable by a rhodanine and/or a rhodanine analog, which is effected by administering to a subject in need thereof a therapeutically effective amount of any of the rigidified compounds presented herein.

As used herein, the phrase "medical condition at least partially treatable by a rhodanine and/or a rhodanine analog" describes medical conditions in which regulating, modulating and/or inhibiting at least a part of the biological processes that are associated therewith can be effected by a compound that comprises one or more rhodanine or rhodanine analog skeleton(s). Such medical conditions can therefore be associated with biological processes that involve, for example, aldose reductase, β-lactamase, a fungal infection, a sialyl Lewis X synthesis, VEGF, phospholipase D and PIN-1.

Such medical conditions include, for example, Alzheimer's disease, schizophrenia, atherosclerosis, an autoimmune disease or disorder, a bacterial infection, a blood coagulation disease or disorder, a bone disease or disorder, cancer, a cardiovascular disease or disorder, a CNS disease or disorder, diabetes, a fungal infection, a gastro-intestinal disease or disorder, hair loss, hypercholesterolemia, inflammation, pain and a viral infection. Preferably, the bacterial infection is selected from the group consisting of an anthrax infection, a cholera infection and a tuberculosis infection. Preferably, the viral infection is selected from the group consisting of a hepatitis C infection, a herpes infection, a HIV infection and a smallpox infection.

In each of the methods and uses described herein, the rigidified compounds described herein can be utilized either alone or in combination with an additional therapeutically active agent. The additional therapeutically active agent can be selected according to the treated condition or the biological process that is affected.

In each of the various aspects of the present invention, the rigidified compounds presented herein can be utilized either per se, or as a part of a pharmaceutical composition where they are mixed with a pharmaceutically acceptable carrier. Thus, according to an additional aspect of the present invention there is provided a pharmaceutical composition which comprises, as an active ingredient, a rigidified compound as described herein, and a pharmaceutically acceptable carrier.

Additionally, the rigidified compounds presented herein can be used for the preparation of a medicament, wherein the medicament is preferably for regulating, modulating and/or inhibiting a biological process depending at least in part on heparanase activity. Preferably the medicament is for treating a heparanase associated disease or disorder in a subject in need thereof and/or for treating a heparin binding protein associated disease or disorder.

Further preferably, the rigidified compounds presented herein can be used for the preparation of a medicament for treating a medical condition which is at least partially treatable by a rhodanine and/or a rhodanine analog.

As used herein a "pharmaceutical composition" refers to a preparation of one or more of the rigidified compounds described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the rigidified compounds into preparations which, can be used pharmaceutically. Proper formulation is dependent upon the route of administration chosen.

For injection, the rigidified compounds of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the rigidified compounds of the invention can be formulated readily by combining the rigidified compounds with pharmaceutically acceptable carriers well known in the art. Such carriers enable the rigidified compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active rigidified compounds doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the rigidified compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the rigidified compounds for use according to the present invention are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the rigidified compounds and a suitable powder base such as, but not limited to, lactose or starch.

The rigidified compounds described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the rigidified compounds preparation in water-soluble form. Additionally, suspensions of the rigidified compounds may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the rigidified compounds to allow for the preparation of highly concentrated solutions.

Alternatively, the rigidified compounds may be in powder form for constitution with a suitable vehicle, e.g., sterile, pyrogen-free water, before use.

The rigidified compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of rigidified compounds effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any rigidified compounds used in the methods of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test rigidified compounds, which achieves a half-maximal reduction of the mean arterial blood pressure). Such information can be used to more accurately determine useful doses in humans.

Toxicity and therapeutic efficacy of the rigidified compounds described herein can be determined by standard pharmaceutical procedures in experimental animals, e.g., by determining the $EC_{50}$, the $IC_{50}$ and the $LD_{50}$ (lethal dose causing death in 50% of the tested animals) for a subject rigidified compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve 50-90% vasorelaxation of contracted arteries. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a rigidified compounds of the invention formulated in a compatible pharmaceutical carrier may also be prepared, placed in an appropriate container, and labeled for treatment of an indicated condition or diagnosis, as is detailed hereinabove.

Thus, according to an embodiment of the present invention, depending on the selected components of the rigidified compounds, the pharmaceutical compositions of the present invention are packaged in a packaging material and identified in print, in or on the packaging material, for use in the treatment of any of the medical conditions described herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

As discussed hereinabove, U.S. patent application Ser. No. 10/916,598 teaches a family of rhodanine or rhodanine analogs derivatives which were found highly active in inhibiting heparanase activity. These compounds are collectively represented by the following general formula:

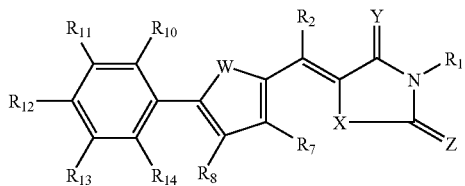

wherein X, Y, Z, W and $R_1$, $R_2$, $R_7$, $R_8$ and $R_{10}$-$R_{14}$ are as defined hereinabove.

This family of compounds served as a preliminary model (basic structure) for the design and practice of the novel, rigidified compounds taught herein.

Thus, several synthetic routes have been designed in order to provide representative subfamilies of rigidified compounds which maintain the structural features of the above presented structure, as follows:

The first subfamily of rigidified rhodanine analogs, represented by Models Ia, Ib and Ic below, is of compounds having the basic structure presented above, rigidified by connecting a first aryl or heteroaryl residue (e.g., a furan-like ring) and the rhodanine-like ring as follows (rigidification marked in bold):

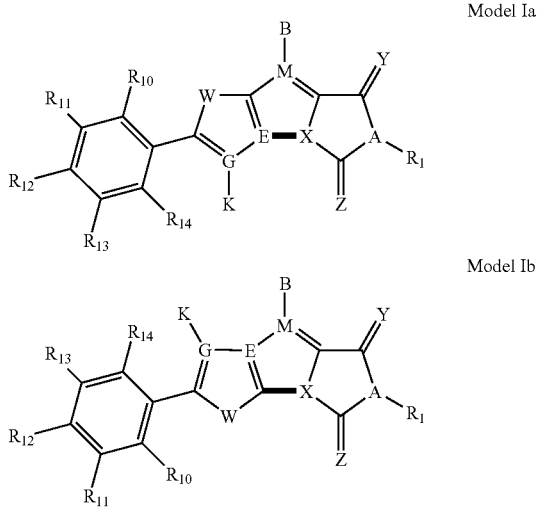

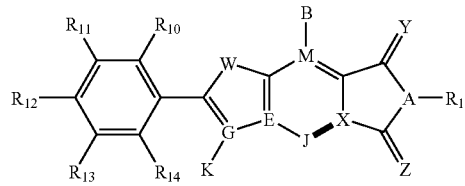

The second family of rigidified rhodanine analogs, represented by Model II below, is of compounds having the basic structure presented above, rigidified by connecting the B substituent of the general formula above and one of the oxo/thioxo (or selenium) groups of the rhodanine-like ring (rigidification marked in bold):

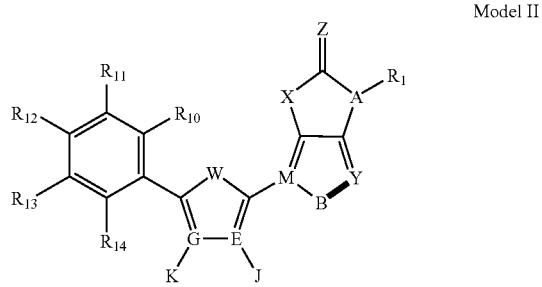

The third family of rigidified rhodanine analogs, represented by Model III below, is of compounds having the basic structure presented above, rigidified by connecting both the first aryl or heteroaryl residue (e.g., a furan-like ring) and the rhodanine-like ring (as in Model I) and the B substituent of the general formula above and one of the oxo/thioxo (or selenium) groups of the rhodanine-like ring (as in Model II) (rigidification marked in bold):

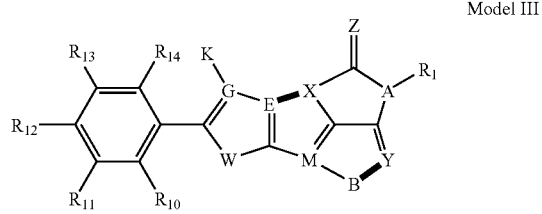

The fourth family of rigidified rhodanine analogs, represented by Models IVa and IVb below, is of compounds having the basic structure presented above, rigidified by connecting both the first aryl or heteroaryl residue (e.g., a furan-like ring) and one of the oxo/thioxo (or selenium) groups of the rhodanine-like ring (rigidification marked in bold):

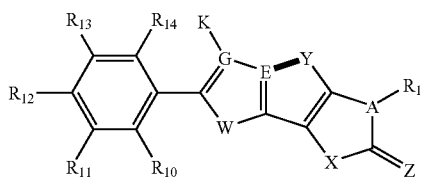

Model IVa

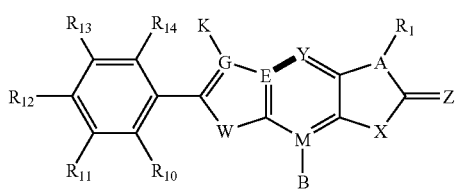

Model IVb

Chemical Synthesis

The following describes various synthetic routes for the preparation of exemplary compounds of the various subfamilies categorized as Models Ia, Ib, Ic, II, III, IVa and IVb above, as well as of analogs thereof.

Materials and Instrumental Data

Reagents, starting materials and solvents were purchased from Aldrich, Sigma, Merck and JT Baker.

NMR was performed on a Brucker AM-300 spectrometer using $SiMe_4$ as an internal standard.

HPLC was performed on a Waters 2695 Alliance purification system equipped with a Waters 996 PDA unit.

MS was performed on a Finnigan 4021 quadrapole gas chromatograph and mass spectrometer.

Preparation of Compounds of Model Ia

Preparation of 4-(6-Oxo-2-substituted-4-thioxo-6H-1-oxa-3b,5-diaza-cyclopenta[a]pentalen-5-yl)-butyric acid—General Procedure I Various derivatives of 4-(6-Oxo-2-substituted-4-oxo/thioxo-6H-1-oxa-3b,5-diaza-cyclopenta[a]pentalen-5-yl)-butyric acid, each having a different substituent at the position numbered "2" (see, e.g., Scheme 1 below), such as a substituted or unsubstituted alkyl or aryl group, having a general structure as depicted below, are prepared as follows:

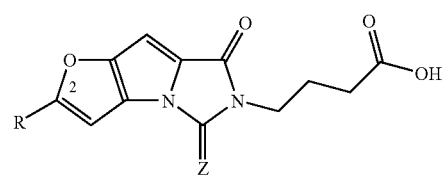

Z = e.g., O or S; R = e.g., alkyl or aryl

Preparation of a 4-(6-Oxo-2-substituted-oxo/thioxo-6H-1-oxa-3b,5-diaza-cyclopenta[a]pentalen-5-yl)-butyric acid ethyl ester Scheme 1

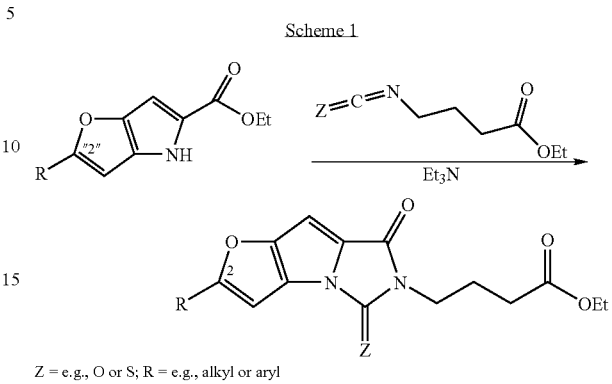

Z = e.g., O or S; R = e.g., alkyl or aryl

As depicted in Scheme 1, a "2"-substituted-4H-furo[3,2-b]pyrrole-5-carboxylic acid ethyl ester (0.1 mmol), prepared according to the procedures described hereinbelow in general procedures II and III, using an appropriate starting material (in which R is alkyl, aryl or the like), is placed in a heavy-walled glass tube with a threaded Teflon plug, and ethyl 4-isothiocyanatobutyrate or ethyl 4-isocyanatobutyrate (1.03 mmol, 10 molequivalents) and triethylamine (TEA, 2 mmol, 20 molequivalents) are added thereto. The glass tube is sealed and the mixture is heated with stirring at 130° C. overnight. Additional isothiocyanate or isocyanate (1.03 mmol, 10 molequivalents) is then added and heating is continued at 130° C. for additional 6 hours. The resulting mixture is dissolved in chloroform and a purified product is isolated by column chromatography on silica (G60 mesh 70-230), using a hexane:ethyl acetate mixture as eluent.

Hydrolysis of a 4-(6-Oxo-2-substituted-4-oxo/thioxo-6H-1-oxa-3b,5-diaza-cyclopenta[a]pentalen-5-yl)-butyric acid Scheme 2

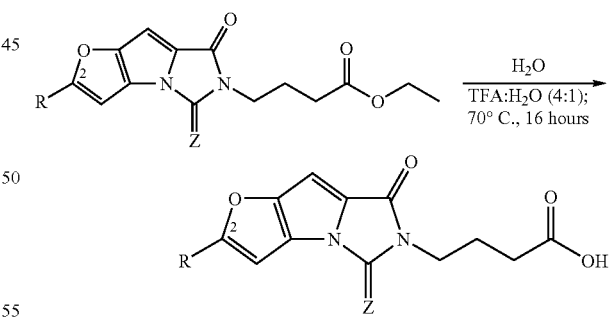

Z = e.g., O or S; R = e.g., alkyl or aryl

As depicted in Scheme 2, a {4-[2-substituted-6-oxo-4-oxo/thioxo-6H-1-oxa-3b,5-diaza-cyclopenta[a]pentalen-5-yl]-butyric acid ethyl ester (0.023 mmol) is dissolved in TFA (2 ml), water (0.5 ml) is added and the mixture is heated at 70° C. overnight. Additional water is then added and the mixture is evaporated under reduced pressure until all TFA is removed. The remaining water is removed by azeotropic distillation with ethanol under reduced pressure to afford the pure free acid.

Preparation of a 4-(6-Oxo-2-substituted-4-oxo/thioxo-6H-1-oxa-3b,5-diaza-cyclopenta[a]pentalen-5-yl)-butyric acid amide

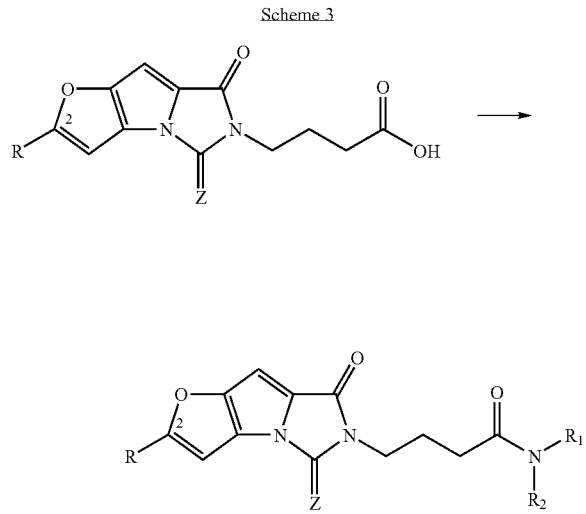

Z = e.g., S or O;
R = e.g., alkyl or aryl;
R$_1$, R$_2$ = e.g., alkyl or aryl

As depicted in Scheme 3, a 4-(6-Oxo-2-substituted-4-oso/thioxo-6H-1-oxa-3b, 5-diaza-cyclopenta[a]pentalen-5-yl)-butyric acid amide is prepared by dissolving the corresponding acid in methylene chloride and reacting the same with oxalyl chloride followed by a reaction with the appropriate amine in acetonitrile in the presence of a base.

Preparation of Derivatives of 4-(6-oxo-4-oxo/thioxo-6H-1-oxa-3b,5-diaza-cyclopenta[a]pentalen-5-yl)-butyric acid/esters Substituted at Position 2—General Procedure II Various derivatives of 4-(6-oxo-4-oxo/thioxo-6H-1-oxa-3b,5-diaza-cyclopenta[a]pentalen-5-yl)-butyric acid substituted at position 2 by an alkoxy or aryloxy, also termed herein 4-(2-oxysubstituted-6-oxo-4-oxo/thioxo-6H-1-oxa-3b,5-diaza-cyclopenta[a]pentalen-5-yl)-butyric acid and derivatives thereof, having a general structure as depicted below, are prepared as follows:

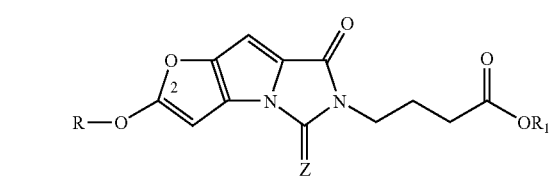

Z = S or O; R = e.g., alkyl or aryl; R$_1$ = e.g., hydrogen, amine or alkyl

Preparation of a Substituted 3-azido-2-(furan-2-yl)-acrylic acid ester

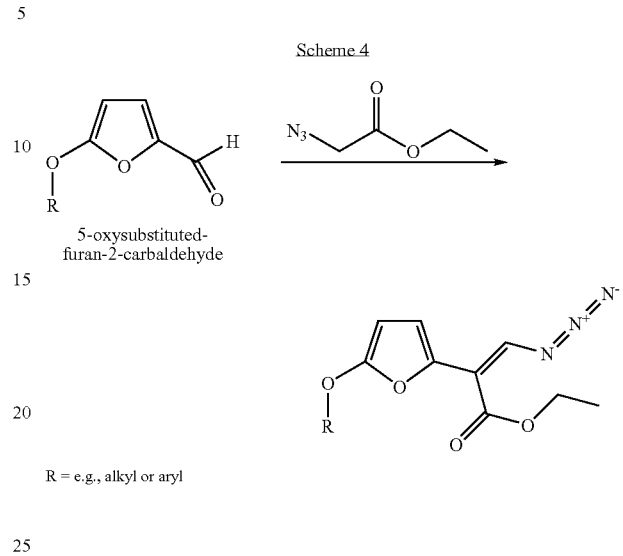

R = e.g., alkyl or aryl

As depicted in Scheme 4, a 5-oxysubstituted-furan-2-carbaldehyde (0.25 mmol) is suspended in dimethoxyethane (DME; 6 ml) and the mixture is heated to 75° C. to obtain a homogenous solution (dissolution of the 5-oxysubstituted-furan-2-carbaldehyde). To the resulting solution, ethyl azidoacetate (2.2 mmol, 8.6 mol molequivalents) is added, followed by addition of 1,8-diazabicyclo[5.4.0]undec-7-ene (DBU, 0.53 mmol, 2.1 mol molequivalents), and the mixture is stirred at 75° C. for half an hour. The progress of the reaction is monitored by TLC (performed on silica plates, using a hexane:ethyl acetate mixture as eluent). The reaction mixture is allowed to cool to room temperature and 2 volumes of chloroform are then added. The chloroform solution is washed twice with 0.1 M HCl and then water and is thereafter dried over Na$_2$SO$_4$, filtered and evaporated under reduced pressure to give the crude product as red oil. The product is purified by column chromatography on silica (G60, mesh 70-230), using a mixture of hexane:dichloromethane as eluent.

Preparation of a 2-oxysubstituted-5,6-dihydro-4H-furo[3,2-b]pyrrole-5-carboxylic acid ethyl ester

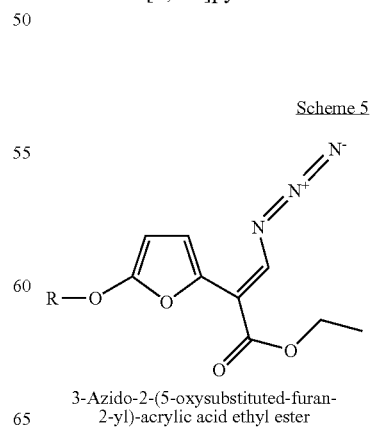

3-Azido-2-(5-oxysubstituted-furan-2-yl)-acrylic acid ethyl ester

-continued

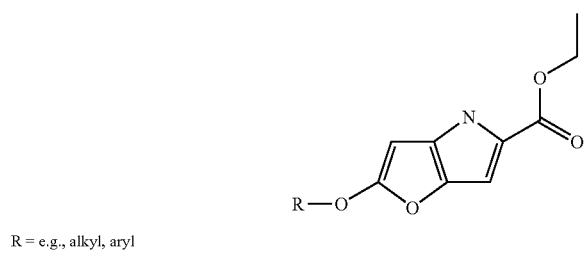

R = e.g., alkyl, aryl

As depicted in Scheme 5, to the isolated 3-azido-2-(5-oxysubstituted-furan-2-yl)-acrylic acid ethyl ester, obtained as described hereinabove, p-xylene (5 ml) is added and the mixture is heated to 145° C. The progress of the reaction is monitored by TLC (performed on silica plates, using hexane:ethyl acetate as eluent). Once the reaction is completed (after about 1 hour), the solvent is evaporated to afford the bicyclic product 2-alkoxy/aryloxy-4H-furo[3,2-b]pyrrole-5-carboxylic acid ethyl ester.

Preparation of a 4-(2-oxysubstituted-6-oxo-4-oxo/thioxo-6H-1-oxa-3b,5-diaza-cyclopenta[a]pentalen-5-yl)-butyric acid ethyl ester Scheme 6

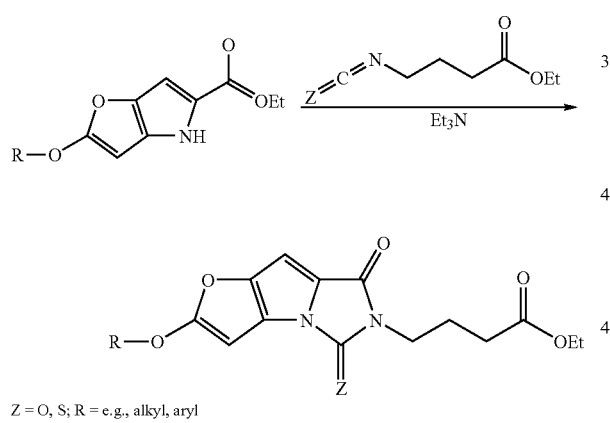

Z = O, S; R = e.g., alkyl, aryl

As depicted in Scheme 6, the bicyclic 2-alkoxy/aryloxy-4H-furo[3,2-b]pyrrole-5-carboxylic acid ethyl ester derivative (0.1 mmol) is placed in a heavy-walled glass tube with a threaded Teflon plug, and ethyl 4-isothiocyanatobutyrate or ethyl 4-isocyanatobutyrate (1.03 mmol, 10 molequivalents) and triethylamine (TEA; 2 mmol, 20 molequivalents) are added thereto. The glass tube is sealed and the mixture is heated with stirring at 130° C. overnight. Additional isothiocyanate/isocyanate (1.03 mmol, 10 molequivalents) is then added and heating is continued at 130° C. for additional 6 hours. The resulting reaction mixture is dissolved in chloroform and a purified product is isolated by column chromatography on silica (G60 mesh 70-230), using hexane:ethyl acetate mixture as eluent.

Hydrolysis of a 4-(2-oxysubstituted-6-oxo-4-oxo/thioxo-6H-1-oxa-3b,5-diaza-cyclopenta[a]pentalen-5-yl)-butyric acid ethyl ester to Obtain an Acid Scheme 7

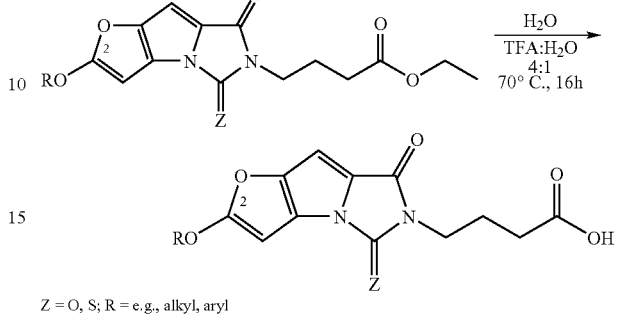

Z = O, S; R = e.g., alkyl, aryl

As depicted in Scheme 7, the 4-(2-oxysubstituted-6-oxo-4-oxo/thioxo-6H-1-oxa-3b,5-diaza-cyclopenta[a]pentalen-5-yl)-butyric acid ethyl ester obtained as described above (0.023 mmol) is dissolved in TFA (2 ml), water (0.5 ml) is added and the mixture is heated at 70° C. overnight. Additional water is then added and the mixture is evaporated under reduced pressure until all the TFA is removed. The remaining water is removed by azeotropic distillation with ethanol under reduced pressure to afford the pure free acid.

Preparation of a 4-(2-oxysubstituted-6-oxo-4-oxo/thioxo-6H-1-oxa-3b,5-diaza-cyclopenta[a]pentalen-5-yl)-N,N-disubstituted-butyramide Scheme 8

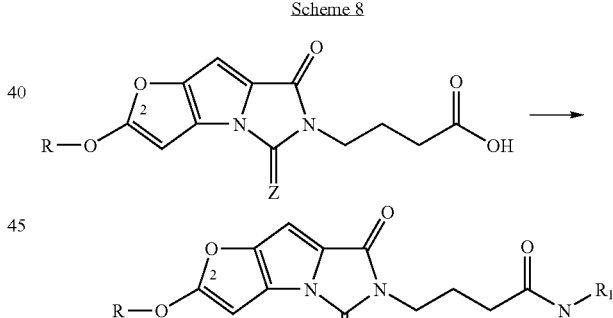

Z = e.g., S or O;
R = e.g., alkyl or aryl;
$R_1$, $R_2$ = e.g., alkyl or aryl

As depicted in Scheme 8, a 4-(2-oxysubstituted-6-oxo-4-oxo/thioxo-6H-1-oxa-3b,5-diaza-cyclopenta[a]pentalen-5-yl)-N,N-disubstituted-butyramide is prepared by dissolving the corresponding acid in methylene chloride and reacting the same with oxalyl chloride followed by a reaction with the appropriate amine in acetonitrile in the presence of a base.

Preparation of 4-(-6-oxo-4-oxo/thioxo-6H-1-oxa-3b,5-diaza-cyclopenta[a]pentalen-5-yl)-butyric acid esters having a Fused Substituted Benzene Ring at Positions 2 and 3—General Procedure III Various derivatives of 4-(-6-oxo-4-oxo/thioxo-6H-1-oxa-3b,5-diaza-cyclopenta[a]pentalen-5-yl)-butyric acid esters having a fused substituted benzene ring at positions 2 and 3, having the general structure depicted below, are prepared as follows:

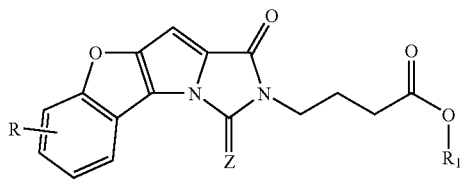

Z = e.g., S or O;
R = e.g., hydrogen, halide, nitro, alkyl, haloalkyl or aryl
R₁ = e.g., alkyl or aryl Preparation of a
3-azido-2-substituted-benzofuran-2-yl-acrylic acid
ethyl ester

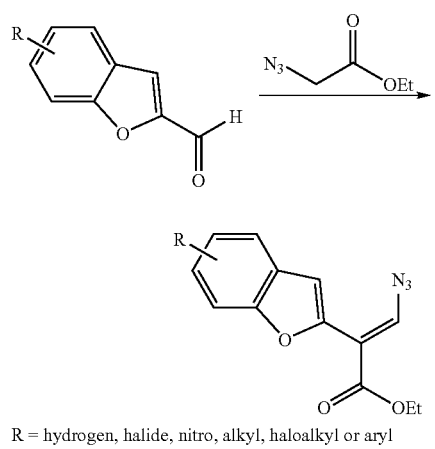

R = hydrogen, halide, nitro, alkyl, haloalkyl or aryl

As depicted in Scheme 9, a substituted benzofuran-2-carbaldehyde (0.25 mmol) is suspended in dimethoxyethane (DME; 6 ml) and the mixture is heated to 75° C. to obtain a homogenous solution (dissolution of the benzofuran-2-carbaldehyde). To the resulting solution, ethyl azidoacetate (2.2 mmol, 8.6 molequivalents) is added, followed by addition of 1,8-diazabicyclo[5.4.0]undec-7-ene (DBU, 0.53 mmol, 2.1 molequivalents) and the mixture is stirred at 75° C. for half an hour. The progress of the reaction is monitored by TLC (performed on silica plates, using a hexane:ethyl acetate mixture as eluent). The reaction mixture is allowed to cool to room temperature and 2 volumes of chloroform are then added. The chloroform solution is washed twice with 0.1 M HCl and water, and is thereafter dried over Na₂SO₄, filtered and evaporated wider reduced pressure to give the crude product. The product is purified by column chromatography on silica (G60, mesh 70-230), using a mixture of hexane:dichloromethane as eluent.

Preparation of a
3H-8-oxa-3-aza-cyclopenta[a]indene-2-carboxylic
acid ethyl ester

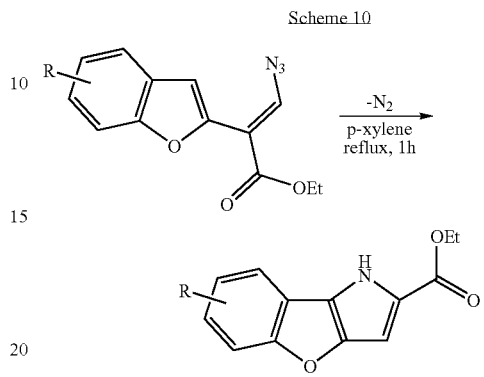

R = hydrogen, halide, nitro, alkyl, haloalkyl or aryl

As depicted in Scheme 10, the isolated 3-azido-2-substituted-benzofuran-2-yl-acrylic acid ethyl ester, prepared as described above, is immediately heated in p-xylene (5 ml) at 145° C., while monitoring by TLC (performed on silica plates, using a hexane:ethyl acetate mixture as eluent). Once the reaction is completed, the solvent is evaporated to afford the tricyclic product.

Preparation of a 4-(2,3-fused substituted benzene-6-oxo-4-oxo/thioxo-6H-1-oxa-3b,5-diaza-cyclopenta[a]pentalen-5-yl)-butyric acid ester

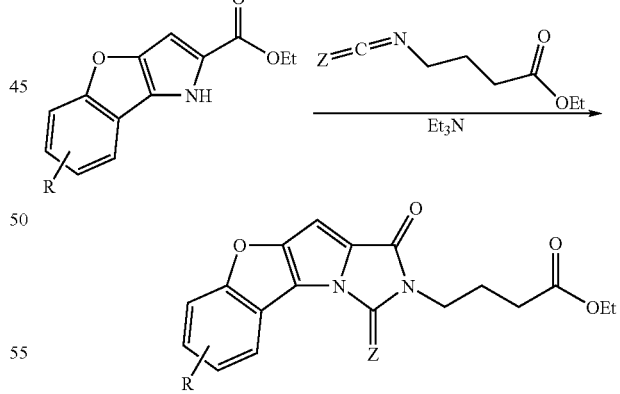

Z = e.g., O or S;
R = e.g., hydrogen, halide, nitro, alkyl, haloalkyl or aryl

As depicted in Scheme 11, the tricyclic benzofuran ester (0.1 mmol) is placed in a heavy-walled glass tube with a threaded Teflon plug, and ethyl 4-isothiocyanatobutyrate or ethyl 4-isocyanatobutyrate (1.03 mmol, 10 molequivalents) and triethylamine (TEA; 2 mmol, 20 molequivalents) are added thereto. The glass tube is well sealed and the mixture is heated with stirring at 130° C. overnight. Additional isothiocyanate/isocyanate (1.03 mmol, 10 molequivalents) is added and the heating at 130° C. is continued for additional 6 hours. The resulting mixture is dissolved in chloroform and a purified product is isolated by column chromatography on silica (G60 mesh 70-230).

Hydrolysis of a 4-(2,3-fused substituted benzene-6-oxo-4-oxo/thioxo-6H-1-oxa-3b,5-diaza-cyclopenta[a]pentalen-5-yl)-butyric acid ester to Obtain an Acid Scheme 12

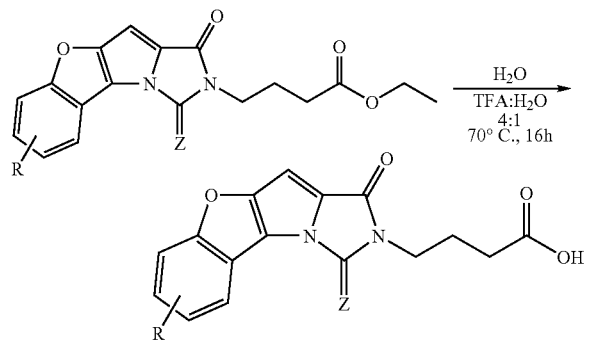

Z = e.g., O or S;
R = e.g., hydrogen, halide, nitro, alkyl, haloalkyl or aryl

As depicted in Scheme 12, the 4-(2,3-fused substituted benzene-6-oxo-4-oxo/thioxo-6H-1-oxa-3b,5-diaza-cyclopenta[a]pentalen-5-yl)-butyric acid ester (0.023 mmol) is dissolved in TFA (2 ml), water (0.5 ml) is added and the mixture is heated at 70° C. overnight. Additional water is then added and the mixture is evaporated under reduced pressure until all TFA is removed. The remaining water is removed by azeotropic distillation with ethanol under reduced pressure to afford the pure free acid.

The corresponding amide is prepared from the acid, according to the procedure described hereinabove.

Preparation of Compounds of Model Ib

Preparation of 4-[1,3-dioxo-5-(substituted-phenyl)-1H-4-oxa-2,3a-diaza-cyclopenta[a]pentalen-2-yl]-butyric acid and/or 4-[1-oxo-3-thioxo-5-(substituted-phenyl)-1H-4-oxa-2,3a-diaza-cyclopenta[a]pentalen-2-yl]-butyric acid derivatives—General Procedure IV Various derivatives of 4-[1,3-dioxo-5-(substituted-phenyl)-1H-4-oxa-2,3a-diaza-cyclopenta[a]pentalen-2-yl]-butyric acid and/or 4-[1-oxo-3-thioxo-5-(substituted-phenyl)-1H-4-oxa-2,3a-diaza-cyclopenta[a]pentalen-2-yl]-butyric acid, having a general structure as depicted below, are prepared as follows:

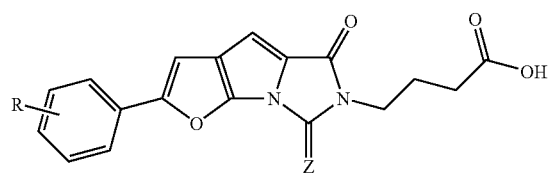

Z = e.g., S (for 4-[1-oxo-3-thioxo-5-(substituted-phenyl)-1H-4-oxa-2,3a-diaza-cyclopenta[a]pentalen-2-yl]-butyric acid) or O (4-[1,3-dioxo-5-(substituted-phenyl)-1H-4-oxa-2,3a-diaza-cyclopenta[a]pentalen-2-yl]-butyric acid);
R = e.g., hydrogen, halide, nitro, alkyl, haloalkyl or aryl Preparation of 2-(furan-3-yl)-1,3-dioxolane Scheme 13

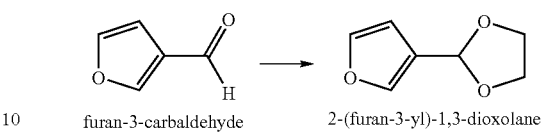

furan-3-carbaldehyde        2-(furan-3-yl)-1,3-dioxolane

As depicted in Scheme 13 above, a mixture of furan-3-carbaldehyde (1.20 mol), ethylene glycol (1.32 mol), p-toluenesulfonic acid (4.6 grams, 0.024 mol) and benzene (100 ml) is heated to reflux for 19 hours in a 500 ml round-bottomed flask fitted with a Dean-Stark trap, while water are removed from the mixture by azeotropic distillation. Once water ceases to condense, the reaction mixture is washed with saturated sodium bicarbonate (NaHCO₃, 200 ml). The combined organic phase is washed with water (100 ml) and saturated sodium chloride (NaCl, 100 ml), dried over MgSO₄, and then concentrated a rotary evaporator. The residual paste is purified by distillation at 80° C. and 10 Torr (1333 pascals).

Preparation of 5-Aryl-2-furan-3-yl[1,3]dioxalane

Scheme 14

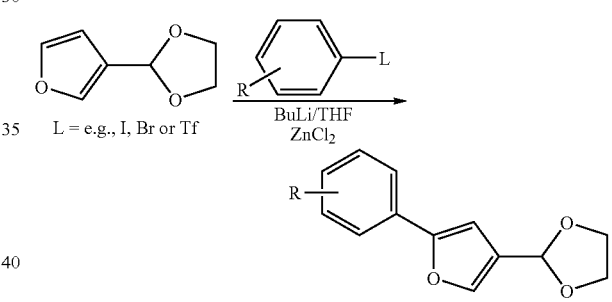

L = e.g., I, Br or Tf

As depicted in Scheme 14 above, a solution of butyl lithium in hexane (1.6 M, 10 ml) is added to a solution of 2-(furan-3-yl)-1,3-dioxolane in dry THF (10 mmol, 30 ml) placed in a cold bath set at −20° C. and under anhydrous atmosphere. The reaction mixture is stirred for 2 hours, anhydrous zinc chloride (ZnCl₂, 20 mmol) is added thereafter and the resulting mixture is stirred at 25° C. for 2 additional hours. Aryl iodide, triflate or bromide (8.95 grams, 10 mmol), lithium chloride (LiCl, 20 mmol) and tetrakis(triphenylphosphine) palladium (Pd(PPh₃)₄, 0.3 mmol) are thereafter added and the mixture is heated at reflux for 18 hours. The solution is then cooled, an aqueous solution of EDTA (40 mmol, 100 ml) is added and the pH is adjusted to about 8 with saturated aqueous sodium bicarbonate (NaHCO₃). The solution is stirred for 15 minutes and then poured into a separatory funnel and extracted with methylene chloride (3×200 ml). The combined organic fractions are dried over anhydrous Na₂SO₄, filtered and concentrated using a rotary evaporator. The crude product is purified by column chromatography.

As depicted in Scheme 15 below, a solution of the protected substituted aldehyde (2-(furan-3-yl)-1,3-dioxolane) and pyrydinium tosylate (PPTS) in acetone/water is refluxed, while monitoring the reaction progress by TLC. Once the reaction is completed (all starting material are consumed), the solution is cooled and extracted with methylene chloride. The organic phase is dried over anhydrous sodium sulphate, filtered, and evaporated on a rotary evaporator. The crude product is then purified by column chromatography.

Scheme 15

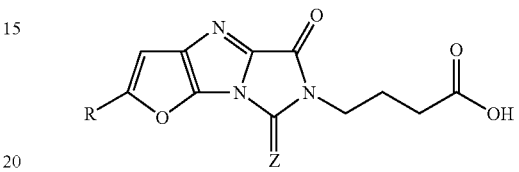

The resulting aldehyde is then reacted with ethyl azidoacetate and ethyl 4-isocyanat butyrate or ethyl 4-isothiocyanatobutyrate, according to the procedures described hereinabove and as is summarized in Scheme 16 below, to give the final product.

Preparation of 4-[2-(substituted-aryl)-5-oxo-7-thioxo-5H-furo[3,2-d]imidazo[1,5-a]imidazol-6-yl]-butyric acid derivatives and 4-[2-(substituted-aryl)-5,7-dioxo-5H-furo[3,2-d]imidazo[1,5-a]imidazol-6-yl]-butyric acid—General Procedure V Various derivatives of 4-[2-(substituted-aryl)-5-oxo-7-thioxo-5H-furo[3,2-d]imidazo[1,5-a]imidazol-6-yl]-butyric acid and 4-[2-(substituted-aryl)-5,7-dioxo-5H-furo[3,2-d] imidazo[1,5-a]imidazol-6-yl]-butyric acid, having a general structure as depicted below, are prepared as follows:

Z - e.g., S, O
R = e.g., substituted aryl

As depicted in Scheme 17 below, equimolar quantities of an aryl-substituted amino-furan and 98% formic acid are mixed and heated at 100° C. for 3 hours. Excess acid is Scheme 16

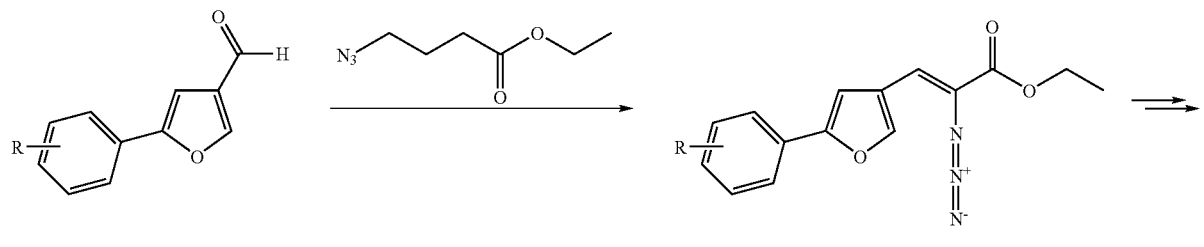

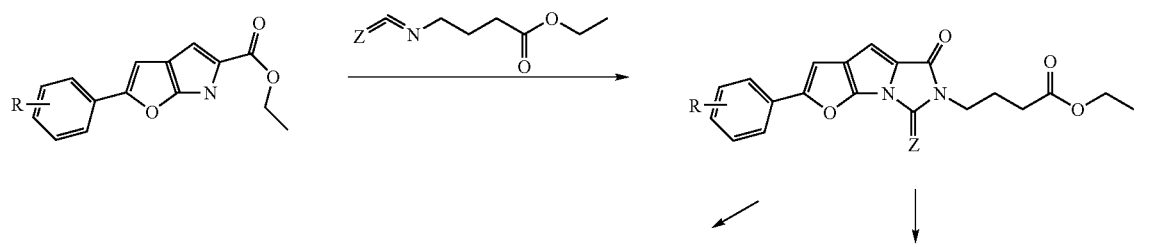

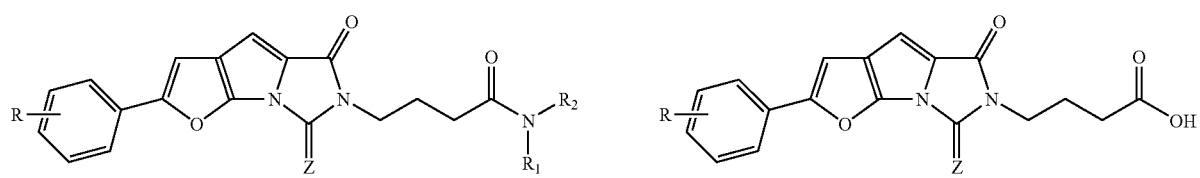

removed by evaporation under reduced pressure and the resulting crude aryl-substituted amido-furan is purified by column chromatography.

Scheme 17

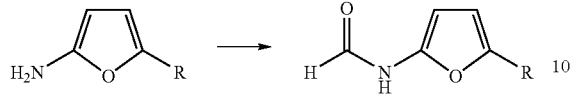

As depicted in Scheme 18 below, the aryl-substituted amido-furan (1 mmol), methylene chloride (5 ml) and sodium azide (1 mmol) are mixed and cooled to 0° C. Trifluoroacetic anhydride (1 mmol) is added and the stirred reaction mixture is allowed to warm up to room temperature and is stirred for additional 24 hours. Saturated sodium bicarbonate (5 ml) is then added followed by the addition of 5 ml of methylene chloride. The aqueous phase is extracted with 3×20 ml of methylene chloride. The combined organic phase is dried over sodium sulfate, filtered and evaporated under reduced pressure. The crude product is then purified by column chromatography.

Scheme 18

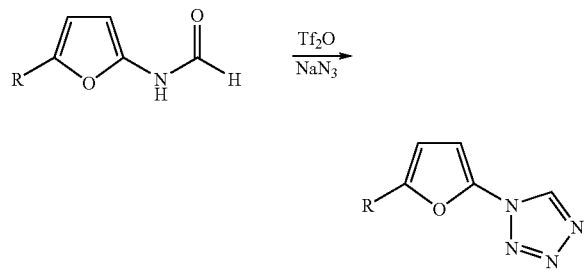

As depicted in Scheme 19 below, the resulting 1-(5-substituted aryl-furan-2-yl)-1H-tetrazole is dissolved in toluene and irradiated until no starting tetrazole is detected by TLC. The solvent in thereafter evaporated under reduced pressure to afford the 5-substituted-aryl-1H-furo[2,3-d]imidazole.

Scheme 19

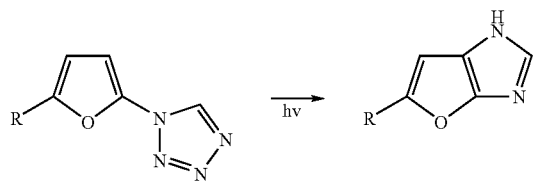

As depicted in Scheme 20 below, triethylamine (1.2 mmol) and trityl chloride (1.2 mmol) are added to a solution of the 5-substituted-aryl-1H-furo[2,3-d]imidazole (1 mmol) in methylene chloride, while monitoring the reaction process by TLC. Once the imidazole is completely consumed, the solvent is evaporated under reduced pressure and the desired protected 5-substituted-aryl-3-trityl-1H-furo[2,3-d]imidazole is purified by column chromatography.

Scheme 20

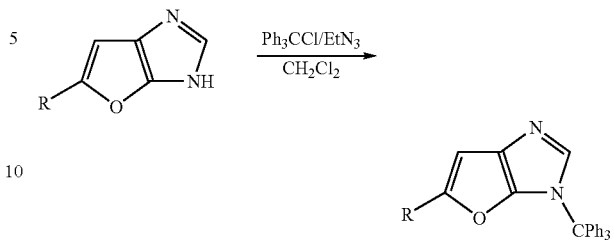

As depicted in Scheme 21 below, a solution of butyl lithium in hexane (1.6 M, 1.2 mmol) is added to a solution of the 5-substituted aryl-3-trityl-1H-furo[2,3-d]imidazole in dry THF (1 mmol, 5 ml) placed in an acetone-dry ice bath (−78° C.) and under anhydrous atmosphere. The reaction mixture is stirred for an hour and the resulting reaction mixture is poured to a slurry of dry ice in dry ether. After stirring the cold reaction mixture for an hour, the mixture is allowed to warm up to room temperature, water (50 ml) is thereafter added and the mixture extracted with chloroform. The organic phase is dried over sodium sulfate, filtered and evaporated under reduced pressure. The desired 5-substituted aryl-3-trityl-3H-furo[2,3-d]imidazole-2-carboxylic acid is then purified by column chromatography.

Scheme 21

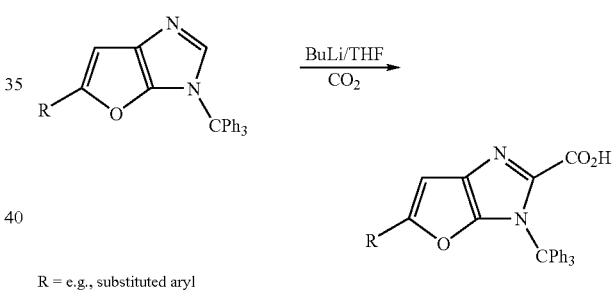

R = e.g., substituted aryl

As depicted in Scheme 22 below, the protected 5-substituted aryl-3-trityl-3H-furo[2,3-d]imidazole-2-carboxylic acid (10 mmol) is dissolved in a mixture of TFA (0.2%), water (1%) and methylene chloride (5 ml), while monitoring the reaction progress by TLC. Once the N-trityl protected starting material is no longer detected the solvent of the reaction mixture is evaporated to dryness under reduced pressure and the crude product is purified by column chromatography on a silica column.

The obtained deprotected 5-substituted-aryl-1H-furo[2,3-d]imidazole-2-carboxylic acid is dissolved in a solution of dry ethanol (5 ml) and sulfuric acid (0.2 ml) and the mixture is stirred while monitoring the reaction progress by TLC. Once the free acid is no longer detected sodium bicarbonate (0.5 gram) is added and the mixture is stirred for 15 minutes. The ethanol is thereafter evaporated under reduced pressure and the residue is dissolved in methylene chloride (20 ml) and washed with water. The combined organic phase is dried over sodium sulfate, filtered and evaporated under reduced pressure. The resulting 5-substituted aryl-1H-furo[2,3-d]imidazole-2-carboxylic acid ethyl ester is used without further purification.

Scheme 22

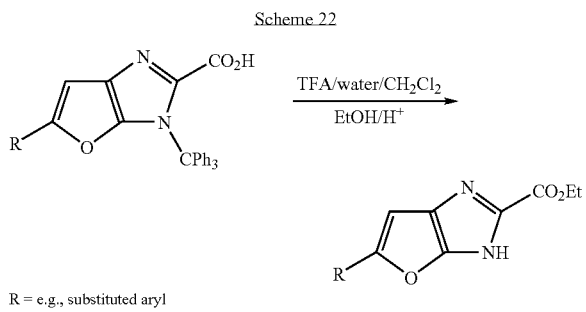

R = e.g., substituted aryl

The resulting 5-substituted aryl-1H-furo[2,3-d]imidazole-2-carboxylic acid ethyl ester is then reacted with ethyl 4-isocyanat butyrate or ethyl 4-isothiocyanatobutyrate, according to the procedures described hereinabove and as is summarized in Scheme 23 below, to give the final product.

and the mixture was extracted with dichloromethane. The aqueous phase was washed with dichloromethane and the combined organic phase was washed with water, dried over sodium sulfate and evaporated to give 865 mg (76% yield) of ethyl azidoacetate as colorless oil having purity higher than 98% (as determined by NMR).

Dimethoxyethane (DME, 6 ml) was added to 5-(4-nitro-phenyl)-furfural (54 mg, 0.25 nmol, 1 molequivalent) and the mixture was heated to 75° C. for 10 minutes to obtain a homogenous solution. Ethyl azidoacetate (278 mg, 2.2 mmol, 8.6 molequivalents, prepared as described above) and 1,8-diazabicyclo[5.4.0]undec-7-ene (DBU; 81 mg, 0.53 mmol, 2.1 molequivalents) were added to the hot solution and the resulting mixture was stirred at 75° C. for half an hour, while monitoring the reaction by TLC. Once furfural was no longer detected, the reaction mixture was allowed to cool and was extracted with chloroform and was thereafter washed with 0.1 M HCl (twice), and water, dried over $Na_2SO_4$ and evaporated under reduced pressure to give the crude product as red oil.

Scheme 23

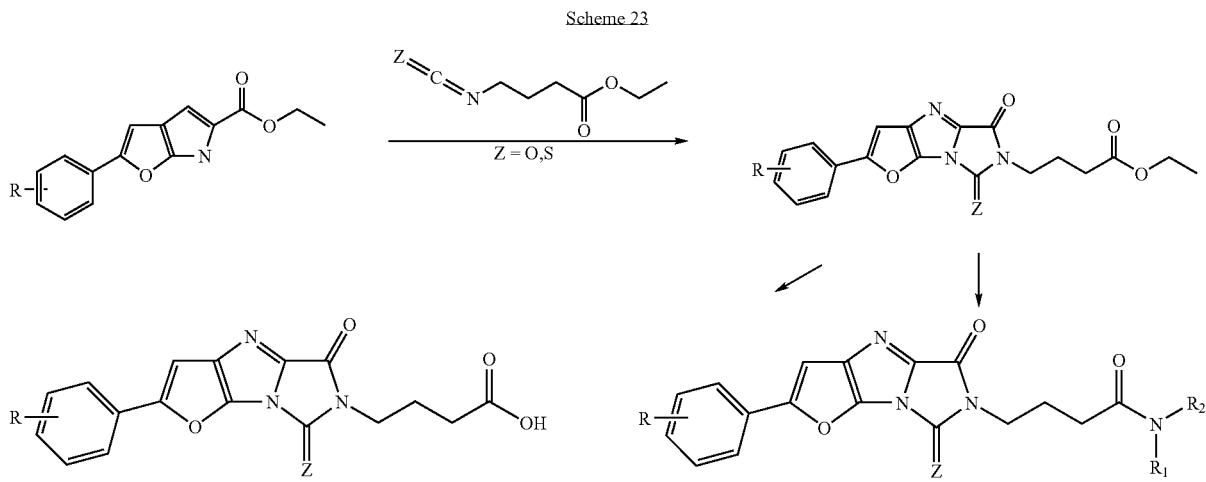

The following describes the preparation of exemplary compounds of the Model Ia subfamily.

Preparation of ethyl 4-[2-(4-nitro-phenyl)-6-oxo-4-thioxo-6H-1-oxa-3b,5-diaza-cyclopenta[a]pentalen-5-yl]-butyric acid ethyl ester (Compound 1)

Compound 1

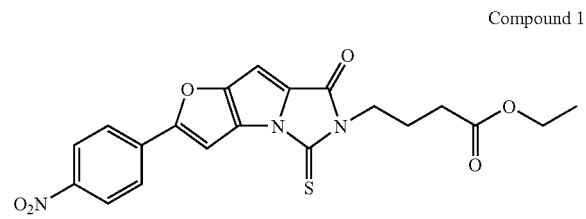

Preparation of ethyl azidoacetate: A mixture of 6:4 acetone:water (20 ml) to was added to sodium azide (1.30 grams, 20 mmol, 2 molequivalents) followed by addition of ethyl bromoacetate (1.67 grams, 10 mmol, 1 molequivalent). The resulting mixture was refluxed overnight at 65° C. The acetone was thereafter evaporated under reduced pressure Chromatographic purification on silica column was carried out using a 6:4 hexane:dichloromethane mixture as eluent to afford 22 mg (27% yield) of 2-azido-3-[5-(4-nitro-phenyl)-furan-2-yl]-acrylic acid ethyl ester as a red solid.

The resulting isolated red solid, 2-azido-3-[5-(4-nitro-phenyl)-furan-2-yl]-acrylic acid ethyl ester (22 mg, 0.067 mmol), was heated in p-xylene (5 ml) at 145° C. for one hour, while monitoring the reaction by TLC. Once a complete consumption of the starting material, along with the appearance of a more polar species, was detected (visible and long wave light), the solvent was evaporated to afford 15 mg (78% yield) of 2-(4-nitro-phenyl)-4H-furo[3,2-b]pyrrole-5-carboxylic acid ethyl ester as a red solid.

The bicyclic compound 2-(4-nitro-phenyl)-4H-furo[3,2-b] pyrrole-5-carboxylic acid ethyl ester (30 mg, 0.1 mmol, 1 molequivalent) was placed in a heavy-walled glass tube with a threaded Teflon plug, and ethyl 4-isothiocyanatobutyrate (178 mg, 1.03 mmol, 10 molequivalents) and triethylamine (TEA; 202 mg, 2 mmol, 20 molequivalents) were added thereto. The glass tube was sealed and the mixture was heated while stirring at 130° C. overnight (18 hours). Additional isothiocyanate (10 molequivalents) was then added and heating was continued at 130° C. for additional 6 hours. The resulting reaction mixture was dissolved in chloroform and the purified product was isolated by column chromatography on silica, using a 9:1 hexane:ethyl acetate mixture as eluent, yielding 21.5 mg (80% purity, 40% yield) of Compound 1 as an orange solid.

$^1$H NMR (CDCl$_3$): δ=8.31 (d, 2H), 7.91 (d, 2H), 7.32 (s, 1H), 6.79 (s, 1H), 4.14 (q, 2H), 3.97 (t, 2H), 2.42 (t, 2H), 2.09 (pent, 2H), 1.26 (t, 3H);

MS (ES$^+$): m/z (%)=450 (MNa$^+$, 100), 428 (MH$^+$, 17), 382 (22).

Preparation of 4-[2-(4-nitro-phenyl)-6-oxo-4-thioxo-6H-1-oxa-3b,5-diaza-cyclopenta[a]pentalen-5-yl]-butyric acid (Compound 2)

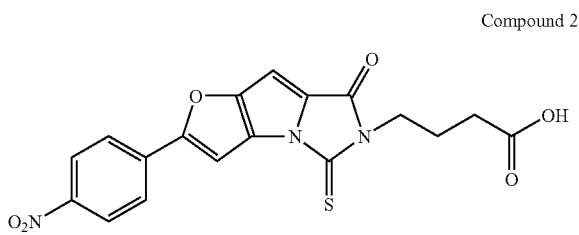

Compound 2

Compound 1 (10 mg, 0.023 mmol) was dissolved in trifluoroacetic acid (TFA, 2 ml), to give a clear red solution. Water (0.5 ml) was added and the mixture was heated at 70° C. overnight. Additional water (2 ml) was then added and the solvents of the reaction mixture were evaporated to give Compound 2 as a yellow-brown solid (8.5 mg, 88% yield).

$^1$H NMR (DMSO d$_6$): δ=8.31 (d, 2H), 8.18 (d, 2H), 7.96 (s, 1H), 7.35 (s, 1H), 3.84 (t, 2H), 2.33 (t, 2H), 1.90 (pent, 2H);

MS (ES$^+$): m/z (%)=422 (MNa$^+$, 31), 400 (MH$^+$, 6), 382 (24), 214 (84), 158 (100).

Preparation of N-methoxy-N-methyl-4-[2-(4-nitro-phenyl)-6-oxo-4-thioxo-6H-1-oxa-3b,5-diaza-cyclopenta[a]pentalen-5-yl]-butyramide (Compound 3)

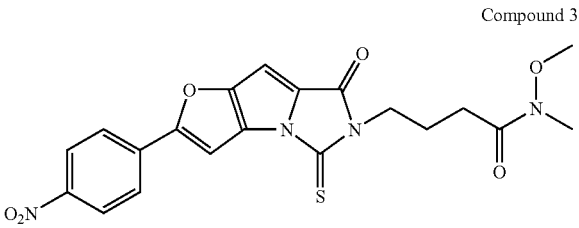

Compound 3

Compound 2 (10 mg, 0.025 mmol) was dissolved in TFA (3 ml), followed by addition of N,O-dimethylhydroxylamine-HCl (5 mg, 0.05 mmol, 2 molequivalent), pyridine (26 mg, 0.32 mmol, 13.2 molequivalent), 4-dimethylamino-pyridine (DMAP; 1 mg, 0.008 mmol, 0.3 molequivalent) and N-(3-Dimethylaminopropyl)-N'-ethylcarbodiimide hydrochloride (EDC-HCl; 10 mg, 0.05 mmol, 2 molequivalent).

The mixture was stirred at 25° C. for 20 hours, while monitoring the reaction by TLC using a 2:8 hexane:ethyl acetate mixture as eluent. The mixture was thereafter extracted with ethyl acetate and 1 M HCl. The aqueous layer was washed with ethyl acetate and the combined organic layers were washed with water and NaHCO$_3$, dried over Na$_2$SO$_4$ and the solvent was evaporated under reduced pressure to give red oil.

Purification of the product by HPLC was carried out using an acetonitrile:water gradient as eluent, to give purified Compound 3 as a yellow solid (5 mg, 45% yield).

$^1$H NMR (CDCl$_3$): δ=8.34 (d, 2H), 7.94 (d, 2H), 7.36 (s, 1H), 6.82 (d, 1H), 4.02 (t, 2H), 3.72 (s, 3H), 3.22 (s, 3H), 2.59 (t, 2H), 2.14 (pent, 2H);

MS (ES$^+$): m/z (%)=465 (MNa$^+$, 100), 443 (MH$^+$, 6), 382 (17), 323 (90), 236 (100).

Preparation of ethyl 4-[2-(4-chloro-phenyl)-6-oxo-4-thioxo-6H-1-oxa-3b,5-diaza-cyclopenta[a]pentalen-5-yl]-butyric acid ethyl ester (Compound 4)

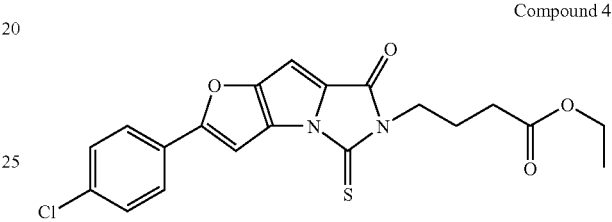

Compound 4

Ethyl azidoacetate was prepared as described hereinabove (see, preparation of Compound 1).

5-(4-chlorophenyl)-furfural (104 mg, 0.5 nmol, 1 molequivalent) was dissolved in ethanol and the mixture was heated at 80° C. so as to obtain a clear solution. Ethyl azidoacetate (552 mg, 4.3 mmol, 8.6 molequivalents) and DBU (162 mg, 1.03 mmol, 2.1 molequivalents) were then added, and the resulting reaction mixture slowly turned red. The reaction mixture was allowed to reflux at 80° C. for half an hour, while monitoring the reaction progress by TLC (silica plates, using 6:4 hexane:ethyl acetate as eluent). Once the starting furfural was no longer detected, ethyl acetate was added and the resulting mixture was washed with 0.1 M HCl. The aqueous phase was washed with ethyl acetate and the combined organic phase was washed with water, dried over Na$_2$SO$_4$ and the solvents were evaporated to afford red oil.

Chromatographic purification on silica column was carried out using a 9:1 hexane:dichloromethane mixture as eluent, to afford 42 mg (26% yield) of 2-azido-3-[5-(4-chloro-phenyl)-furan-2-yl]-acrylic acid ethyl ester as a bright yellow solid.

The obtained 2-Azido-3-[5-(4-chloro-phenyl)-furan-2-yl]-acrylic acid ethyl ester (21 mg, 0.066 mmol) was dissolved in p-xylene and the mixture was heated to 140° C. for half an hour. The solvent was thereafter evaporated to give 15 mg (78% yield) of 2-(4-chloro-phenyl)-4H-furo[3,2-b]pyrrole-5-carboxylic acid ethyl ester as a red solid.

The bicyclic compound 2-azido-3-[5-(4-chloro-phenyl)-furan-2-yl]-acrylic acid ethyl ester (48 mg, 0.16 mmol, 1 molequivalent) was placed in a heavy-walled glass tube with a threaded Teflon plug, and ethyl 4-isothiocyanatobutyrate (178 mg, 1.03 mmol, 6.4 molequivalents) and triethylamine (TEA; 202 mg, 2 mmol, 12.5 molequivalents) were added thereto. The glass tube was sealed and the reaction mixture was heated while stirring at 130° C. for 6 hours. Additional isothiocyanate (6.4 molequivalents) was then added and the heating was continued at 130° C. for additional 18 hours. The resulting mixture was dissolved in chloroform and the purified product was isolated by column chromatography on silica, using a 9:1 hexane:ethyl acetate mixture as eluent, to afford Compound 4 as a red solid (38 mg, 57% yield).

$^1$H NMR (CDCl$_3$): δ=7.73 (d, 2H), 7.45 (d, 2H), 7.15 (s, 1H), 6.79 (s, 1H), 4.17 (q, 2H), 3.99 (t, 2H), 2.45 (t, 2H), 2.12 (pent, 2H), 1.30 (t, 3H);

MS (ES$^+$): m/z (%)=439 and 441 (MNa$^+$, 100), 417 and 419 (MH$^+$, 22), 371 and 373 (23).

Preparation of 4-[2-(4-chloro-phenyl)-6-oxo-4-thioxo-6H-1-oxa-3b,5-diaza-cyclopenta[a]pentalen-5-yl]-butyric acid (Compound 5)

Compound 5

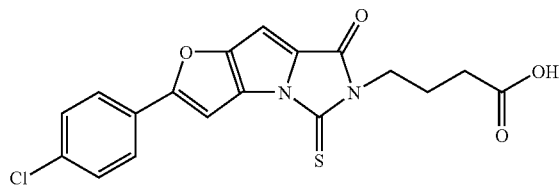

Compound 4 (17.5 mg, 0.042 mmol) was dissolved in TFA (2 ml), to give a clear red solution. Water (0.5 ml) was added and the mixture was heated at 70° C. overnight. Additional water (2 ml) was added and the solvents of the reaction mixture reaction mixture were evaporated under reduced pressure to afford Compound 5 as a yellow-brown solid (15 mg, 90% yield).

$^1$H NMR: δ=7.95 (d, 2H), 7.70 (s, 1H), 7.56 (d, 2H), 7.31 (s, 1H), 3.48 (t, 2H), 2.33 (t, 2H), 1.75 (pent, 2H);

MS (ES$^+$): m/z (%)=427 and 429 (MK$^+$, 15), 411 and 413 (MNa$^+$, 76), 389 and 491 (MH$^+$, 13), 371 and 373 (24), 229 (100).

Preparation of 4-[2-(4-chloro-phenyl)-6-oxo-4-thioxo-6H-1-oxa-3b,5-diaza-cyclopenta[a]pentalen-5-yl]-N,N-diethyl-butyramide (Compound 6)

Compound 6

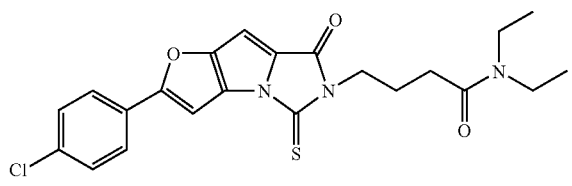

Compound 5 (50 mg, 0.128 mmol) was dissolved in dry THF (4 ml), followed by addition of N-(3-dimethylamino-propyl)-N'-ethylcarbodiimide hydrochloride (EDC-HCl; 123 mg, 0.64 mmol, 5 molequivalent), pyridine (106 mg, 1.35 mmol, 10 equivalents), diethylamine-HCl (42 mg, 0.38 mmol, 3 molequivalent) and 4-dimethylamino-pyridine (DMAP; 3.2 mg, 0.026 mmol, 0.2 molequivalent). Dry dichloromethane (2 ml) was thereafter added so as to obtain a clear solution.

The mixture was stirred at 25° C. for 20 hours, while monitoring the reaction by TLC using a 2:8 hexane:ethyl acetate mixture as eluent. The mixture was thereafter extracted with chloroform and 1 M HCl. The aqueous layer was washed with chloroform and the combined organic layers were washed with water and NaHCO$_3$, dried over Na$_2$SO$_4$ and the solvent was evaporated under reduced pressure to give a red residue.

Purification of the crude product by HPLC was carried out using an acetonitrile:water gradient as eluent, to give purified Compound 6 as a yellow solid (35 mg, 62% yield).

$^1$H NMR (CDCl$_3$): δ=7.73 (d, 2H), 7.45 (d, 2H), 7.15 (s, 1H), 6.77 (d, 1H), 4.02 (t, 2H), 3.37 (brq, 4H), 2.48 (t, 2H), 2.13 (pent, 2H), 1.18 (brt, 6H);

MS (ES$^+$): m/z (%)=466, 468 (MNa$^+$, 76), 444, 446 (MH$^+$, 12), 268, 270 (24), 236, 238 (100).

Preparation of 3,3-dimethyl-4-[2-(4-nitro-phenyl)-6-oxo-4-thioxo-6H-1-oxa-3b,5-diaza-cyclopenta[a]pentalen-5-yl]-butyric acid ethyl ester (Compound 7)

Compound 7

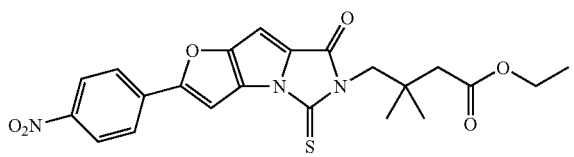

Ethyl 3,3-dimethylacrylate (40 grams, 310 mmol) was dissolved in acetonitrile (350 ml), and nitromethane (84.5 ml, 1600 mmol, 5 molequivalents) and 1,8-diazabicyclo[5.4.0]undec-7-ene (DBU, 69.4 ml, 470 mmol, 1.5 molequivalents) were added thereto. The mixture was heated at 60° C. for 3 days, and the solvent was evaporated thereafter under reduced pressure. Ethyl acetate and 1M HCl were added to the resulting residue, and the organic phase was separated. The acidic aqueous layer was washed twice with ethyl acetate, the combined organic phase was dried over Na$_2$SO$_4$, and the solvent was evaporated under reduced pressure. The product, 3,3-dimethyl-4-nitro-butyric acid ethyl ester, was distilled under reduced pressure (0.4 mmHg) at 62° C. and, and collected (43.67 grams, 77% yield) as colorless oil.

3,3-Dimethyl-4-nitro-butyric acid ethyl ester (22.65 grams, 119.8 mmol) was dissolved in methanol (120 ml) followed by addition of 10% palladium (250 mg) on activated charcoal. The reaction mixture was placed in a hydrogenation apparatus (Parr Instrument Company), the chamber was evacuated and filled with hydrogen (4.4 atmospheres) five times over a time period of 16 hours while the reaction mixture was stirred at 110° C. The reaction mixture was thereafter filtrated, washed and the solvent was evaporated to give 4,4-dimethyl-2-pyrrolidinone (13.14 grams, 97% yield) as oil.

4,4-Dimethyl-2-pyrrolidinone (2.52 grams, 22.3 mmol) was added to a mixture of concentrated HCl (50 ml) and water (50 ml) and the resulting mixture refluxed at 120° C. for 20 hours. After cooling to room temperature the mixture was washed twice with dichloromethane. The aqueous layer was evaporated to give 4-amino-3,3-dimethyl-butyric acid hydrochloride (3.425 grams, 92% yield) as a white solid.

Acetyl chloride (31 ml) was added dropwise over a time period of 5 minutes to ethanol (180 ml) while stirring and cooling in ice water bath. After additional 5 minutes, the obtained solution was added to a solution of 4-amino-3,3-dimethyl-butyric acid hydrochloride (30.07 grams, 180 mmol) in ethanol (20 ml). The mixture was refluxed at 85° C. for 16 hours, and the solvent was removed under reduced pressure to give to 4-amino-3,3-dimethyl-butyric acid ethyl ester hydrochloride (33.11 grams, 94% yield) as oil.

4-amino-3,3-dimethyl-butyric acid ethyl ester hydrochloride (21.45 grams, 109.6 mmol, 1 molequivalent) was dissolved in water (150 ml), chloroform (120 ml) was added thereto, and the mixture was vigorously stirred. Thiophosgene (8.1 ml, 105.6 mmol, 0.95 molequivalents) dissolved in chloroform (10 ml) was added thereafter. The pH of the mixture was adjusted to 7.1-7.4 with NaHCO$_3$ and remained stable in this range. The organic phase was extracted and the aqueous layer was washed three times with chloroform. The combined organic layers were dried over Na$_2$SO$_4$, and the solvent was removed under reduces pressure. The product, 4-isothiocyanato-3,3-dimethyl-butyric acid ethyl ester, was distilled under reduced pressure (0.6 mmHg) at 72° C. and, and collected (13.4 grams, 61% yield) as oil.

2-(4-nitro-phenyl)-4H-furo[3,2-b]pyrrole-5-carboxylic acid ethyl ester (212 mg, 0.71 mmol, 1 molequivalent), prepared as described hereinabove (see, preparation of Compound 1), was placed in a round bottom flask and 4-isothiocyanato-3,3-dimethyl-butyric acid ethyl ester (1.4 grams, 7.1 mmol, 10 molequivalents) was added thereto, followed by addition of grinded anhydrous potassium carbonate (K$_2$CO$_3$; 147 mg, 1.1 mmol, 1.5 molequivalents). The mixture was heated while stirring at 140° C. for 16 hours. The reaction mixture was thereafter dissolved in chloroform and 5% citric acid solution, the organic phase was extracted, and the aqueous layer was washed with chloroform several times. The combined organic layers were dried over Na$_2$SO$_4$, the solvent was removed under reduced pressure, and the crude product was triturated in ethanol to give Compound 7 (322 mg, 40% yield) as an orange solid.

$^1$H NMR (CDCl$_3$): δ=8.336 (d, 2H), 7.903 (d, 2H), 7.326 (s, 1H), 6.791 (s, 1H), 4.163 (q, 2H), 3.949 (s, 2H), 2.391 (s, 2H), 1.278 (t, 3H), 1.156 (s, 6H);

MS (ES$^+$): m/z (%)=478 [M+Na]$^+$, 456 [MH$^+$].

Preparation of 3,3-Dimethyl-4-[2-(4-nitro-phenyl)-6-oxo-4-thioxo-6H-1-oxa-3b,5-diaza-cyclopenta[a]pentalen-5-yl]-butyric acid (Compound 8)

Compound 8

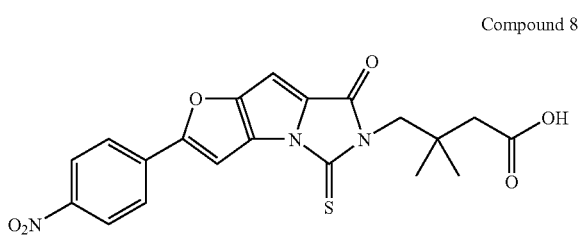

Compound 7 (300 mg, 0.66 mmol) was dissolved in trifluoroacetic acid (TFA, 9 ml). Water (3 ml) was added and the resulting mixture was heated at 90° C. for 16 hours. The reaction mixture was then filtered, washed with ethanol and the solvents were evaporated under reduced pressure to give Compound 8 (234 mg, 83% yield) as an orange solid.

$^1$H NMR (CDCl$_3$): δ=8.343 (d, 2H), 8.067 (d, 2H), 7.640 (s, 1H), 7.002 (s, 1H), 3.958 (s, 2H), 2.348 (s, 2H), 1.145 (s, 6H);

MS (ES$^+$): m/z (%)=466 [M+K]$^+$, 450 [M+Na]$^+$, 428 [MH$^+$].

Preparation of N-hydroxy-3,3-dimethyl-4-[2-(4-nitro-phenyl)-6-oxo-4-thioxo-6H-1-oxa-3b,5-diaza-cyclopenta[a]pentalen-5-yl]-butyramide (Compound 9)

Compound 9

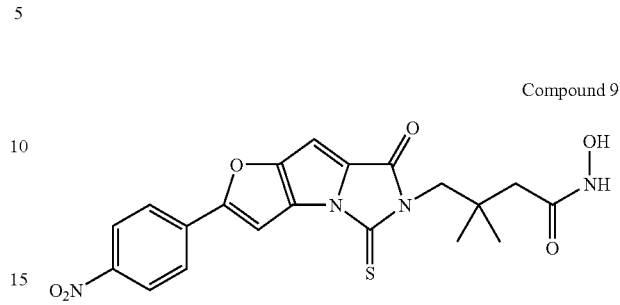

Di-t-butyl dicarbonate, (BOC$_2$O; 205 mg, 0.94 mmol, 2 molequivalents) was dissolved in dry THF (5 ml) and 3-hydroxy-dihydrobenzotriazinone (HODhbt; 91 mg, 0.6 mmol, 1.2 molequivalents) was added thereto, followed by addition of a yellow solution of Et$_3$N (0.07 ml, 0.47 mmol, 1 molequivalent), and 4-dimethylaminopyridine (DMAP; 6 mg, 0.05 mmol, 0.1 molequivalent). After 1 hour of stirring at 25° C. the yellow color disappeared and DMAP (23 mg, 0.19 mmol, 0.4 molequivalent) was added followed by addition of Compound 8 (193 mg, 0.45 mmol). The mixture was stirred at 25° C. for 16 hours while monitoring the reaction by TLC using a 1:1 hexane:ethyl acetate mixture as eluent. The reaction was ceased once a less polar spot, attributed to the active ester intermediate, was observed.

A solution of hydroxylamine hydrochloride (63 mg, 0.9 mmol, 2 molequivalents) and Et$_3$N (0.13 ml, 0.9 mmol, 2 molequivalents) was suspended in 2 ml of acetonitrile. The resulting solution was added to chloroform (5 ml) and the obtained solution was added to the reaction mixture having the active ester intermediate, while monitoring the reaction by TLC. Once a complete consumption of the active ester intermediate was observed (after an additional hour), the product was precipitated, filtered by suction and washed with methanol. Compound 9 (79 mg, 40% yield) was collected as an orange solid.

$^1$H NMR (DMSO): δ=10.38 (br-s, 1H), 8.775 (br-s, 1H), 8.297 (d, 2H), 8.185 (d, 2H), 7.947 (s, 1H), 7.354 (s, 1H), 3.808 (s, 2H), 2.024 (s, 2H), 1.029 (s, 6H).

Preparation of 4-[2-(4-Chloro-phenyl)-6-oxo-4-thioxo-6H-1-oxa-3b,5-diaza-cyclopenta[a]pentalen-5-yl]-3,3-dimethyl-butyric acid ethyl ester (Compound 10)

Compound 10

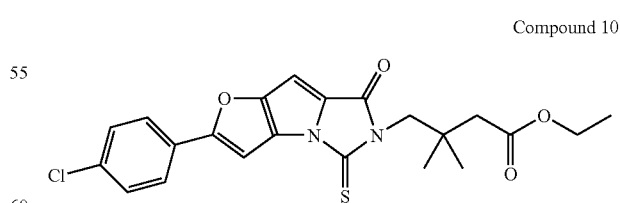

2-(4-chloro-phenyl)-4H-furo[3,2-b]pyrrole-5-carboxylic acid ethyl ester (1.5 grams, 5.1 mmol), prepared as described hereinabove (see, preparation of Compound 4), was placed in a round bottom flask, and 4-isothiocyanato-3,3-dimethyl-butyric acid ethyl ester (6.2 grams, 31 mmol, 6 molequivalents), prepared as described hereinabove (see, preparation of Compound 7), was added thereto, followed by addition of grinded anhydrous potassium carbonate (1.06 grams, 7.7 mmol, 1.5 molequivalents).

The mixture was heated while stirring at 120° C. for 6 hours. The reaction mixture was thereafter dissolved in chloroform, followed by addition of 5% citric acid solution. The resulting mixture was shaken in a separatory funnel, and the organic layer was separated. The aqueous layer was washed with chloroform several times, the combined organic layer was dried ($Na_2SO_4$) and the solvents were removed by evaporation under reduced pressure. The residue was triturated in ethanol and filtrated to give Compound 10 (1.16 grams, 51% yield) as an orange-red solid.

$^1$H NMR ($CDCl_3$): δ=7.73 (d, 2H), 7.46 (d, 2H), 7.15 (s, 1H), 6.79 (s, 1H), 4.18 (q, 2H), 3.97 (s, 2H), 2.43 (s, 2H), 1.31 (t, 3H), 1.19 (s, 6H);

MS ($ES^+$): m/z (%)=467, 469 ($MNa^+$, 75), 445, 447 ($MH^+$, 95), 339, 401 ($MH^+$-EtOH, 100).

Preparation of 4-[2-(4-chloro-phenyl)-6-oxo-4-thioxo-6H-1-oxa-3b,5-diaza-cyclopenta[a]pentalen-5-yl]-3,3-dimethyl-butyric acid (Compound 11)

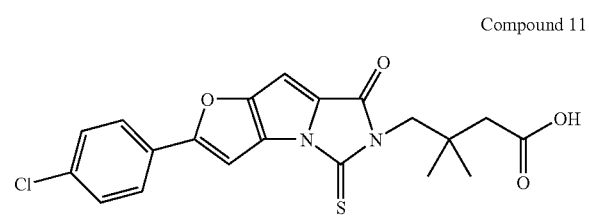

Compound 11

Compound 10 (1.21 grams, 2.3 mmol) was dissolved in TFA (33 ml), water (11 ml) was added thereto, and the resulting mixture was heated at 90° C. for 16 hours. The product was filtered and washed with ethanol to give Compound 11 (800 mg, 83% yield) as an orange solid.

$^1$H NMR ($CDCl_3$): δ=7.844 (d, 2H), 7.503 (d, 2H), 7.381 (s, 1H), 6.975 (s, 1H), 3.967 (s, 2H), 2.396 (s, 2H), 1.169 (s, 6H);

MS ($ES^+$): m/z (%)=415 and 417 [M-H]$^-$, 355 and 357.

Preparation of 4-[2-(4-Chloro-phenyl)-6-oxo-4-thioxo-6H-1-oxa-3b,5-diaza-cyclopenta[a]pentalen-5-yl]-3,3-dimethyl-butyric acid 4-oxo-4H-benzo[d][1,2,3]triazin-3-yl ester (Compound 12)

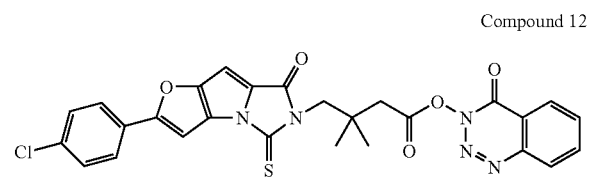

Compound 12

Compound 11 (105 mg, 0.25 mmol) was dissolved in dry THF (5 ml) and 3-hydroxy-dihydrobenzotriazinone (HODhbt; 49 mg, 0.3 mmol, 1.2 molequivalents) was added thereto, followed by addition of $Et_3N$ (51 mg, 0.5 mmol, 2 molequivalents) and 4-dimethylaminopyridine (DMAP; 15 mg, 0.125 mmol, 0.5 molequivalents). The reaction mixture was stirred at 25° C. for 16 hours while being monitored by TLC using a 6:4 hexane:EtOAc mixture as an eluent, until the appearance of a less polar spot, attributed to the active ester intermediate, was observed. Chloroform was thereafter added and the resulting mixture was washed with 1 M HCl, dried ($Na_2SO_4$) and the solvents were removed under reduced pressure to give a red solid. Chromatography was carried out using a 9:1 hexane:ethyl acetate mixture as eluent to give Compound 12 (38 mg, 20% yield) as a orange solid.

$^1$H NMR ($CDCl_3$): δ=8.38 (d, 1H), 8.23 (d, 1H), 8.01 (t, 1H), 7.84 (t, 1H), 7.70 (d, 2H), 7.42 (d, 2H), 7.13 (s, 1H), 6.79 (s, 1H), 4.00 (s, 2H), 2.87 (s, 2H), 1.34 (s, 6H);

MS ($ES^+$): m/z (%)=600 and 602 ($MK^+$, 10), 584 and 586 ($MNa^+$, 100), 562 and 564 ($MH^+$, 28).

Preparation of 4-[2-(4-Chloro-phenyl)-6-oxo-4-thioxo-6H-1-oxa-3b,5-diaza-cyclopenta[a]pentalen-5-yl]-N,N-diethyl-3,3-dimethyl-butyramide (Compound 13)

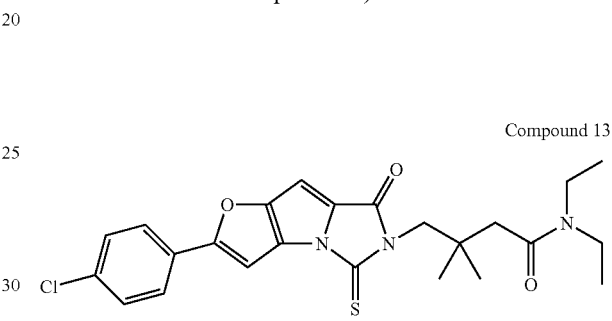

Compound 13

Di-t-butyl dicarbonate, ($BOC_2O$; 218 mg, 1 mmol, 2 molequivalents) was dissolved in dry THF (3 ml) and 3-hydroxy-dihydrobenzotriazinone (HODhbt; 98 mg, 0.6 mmol, 1.2 molequivalents) was added thereto, followed by addition of a yellow solution $Et_3N$ (51 mg, 0.5 mmol, 1 molequivalent) and 4-dimethylaminopyridine (DMAP; 6 mg, 0.05 mmol, 0.1 molequivalent). After 1 hour of stirring at 25° C. the yellow color disappeared and DMAP (25 mg, 0.2 mmol, 0.4 molequivalent) was added followed by addition of a solution of Compound 11 (210 mg, 0.5 mmol) dissolved in dry THF (5 ml) in one portion. The resulting mixture was stirred at 25° C. for 16 hours while being monitored by TLC using a 6:4 hexane:ethyl acetate mixture as eluent, until the appearance of a less polar spot of the active ester intermediate was observed. The solvent was evaporated under reduced pressure and the residue was dissolved in chloroform (10 ml). Diethylamine (72 mg, 1 mmol, 2 molequivalents) was then added and the active ester was consumed after additional 1 hour, as indicated by TLC. Chloroform was then added and the resulting mixture was washed twice with 5% $NaHCO_3$, and 1 M HCl, dried ($Na_2SO_4$) and the solvent was evaporated under reduced pressure to give a red solid (306 mg). Chromatography was carried out using a 8:2 hexane:ethyl acetate mixture as eluent, to give Compound 13 (167 mg, 71% yield) as a red solid.

$^1$H NMR ($CDCl_3$): δ=7.73 (d, 2H), 7.45 (d, 2H), 7.16 (s, 1H), 6.78 (s, 1H), 4.06 (s, 2H), 3.39 (brq, 4H), 2.45 (s, 2H), 1.22 (s, 6H), 1.17 (brs, 6H);

MS ($ES^+$): m/z (%)=494, 496 ($MNa^+$, 14), 472, 474 ($MH^+$, 24), 342 (100).

Preparation of 4-[2-(4-Chloro-phenyl)-6-oxo-4-thioxo-6H-1-oxa-3b,5-diaza-cyclopenta[a]pentalen-5-yl]-N-(2-dimethylamino-ethyl)-3,3-dimethyl-butyramide (Compound 14)

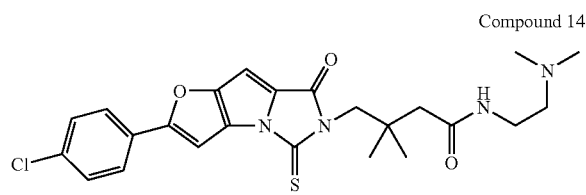

Compound 14

Compound 11 (30 mg, 0.073 mmol) was dissolved in dichloromethane (5 ml) and oxalyl chloride (20 um, 0.219 mmol) and a drop of pyridine was added thereto. The resulting mixture was stirred at room temperature for 1 hour until a complete conversion of the starting material was observed. The solvent was then evaporated under reduced pressure until dryness.

The resulting crude product was dissolved in dichloromethane (5 ml), and ethylene diamine (12 μl, 0.1095 mmol) and triethylamine (20 μl, 0.146 mmol) were added thereto. The mixture was stirred for an hour until complete conversion was observed, and the solvent was thereafter evaporated under reduced pressure. The crude product was purified by column chromatography on a packed silica column, using acetone as a eluent, to give Compound 14 (10 mg, 17% yield).

$^1$H NMR (CDCl$_3$): δ=7.75 (d, 2H), 7.44 (d, 2H), 7.11 (s, 1H), 6.74 (s, 1H), 4.05 (s, 2H), 3.73 (m, 2H), 3.29 (m, 2H); 2.94 (m, 6H); 2.40 (s, 2H), 1.19 (m, 6H);

MS (ES$^+$): m/z (%)=487 ([M+Na]$^+$, (100).

Preparation of 4-[2-(4-Chloro-phenyl)-6-oxo-4-thioxo-6H-1-oxa-3b,5-diaza-cyclopenta[a]pentalen-5-yl]-N-(3-dimethylamino-propyl)-3,3-dimethyl-butyramide (Compound 15)

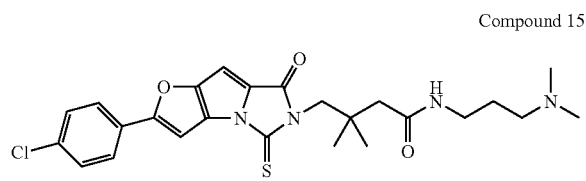

Compound 15

Compound 11 (105 mg, 0.25 mmol) was dissolved in dichloromethane (5 ml) and 3-hydroxy-dihydrobenzotriazinone (HODhbt, 49 mg, 0.3 mmol, 1.2 molequivalents) was added thereto, followed by addition of Et$_3$N (51 mg, 0.5 mmol, 2 molequivalents) and 4-dimethylaminopyridine (DMAP, 15 mg, 0.125 mmol, 0.5 molequivalents). The mixture was stirred at 25° C. for 16 hours while being monitored by TLC, using a 6:4 hexane:ethyl acetate mixture as eluent, until the appearance of a less polar spot of the active ester intermediate was observed. The solvent was then evaporated under reduced pressure and the residue was dissolved in chloroform (10 ml). N,N-dimethylaminopropylamine (DMAPA, 103 mg, 1 mmol, 2 molequivalents) was then added and the active ester was consumed after additional 1 hour, as indicated by TLC. Chloroform was thereafter added and the mixture was washed three times with 5% NaHCO$_3$, with 1 M HCl, dried (Na$_2$SO$_4$) and the solvent was evaporated under reduced pressure to give a red solid. Chromatography was carried out using a 88:10:2 EtOAc:MeOH:Et$_3$N mixture as eluent to give Compound 15 (101 mg, 69% yield) as a red solid.

$^1$H NMR (CDCl$_3$): δ=9.14 (br s, 1H), 7.73 (d, 2H), 7.45 (d, 2H), 7.15 (s, 1H), 6.80 (s, 1H), 4.09 (s, 2H), 3.86 (t, 2H), 3.12 (t, 2H), 2.83 (s, 6H), 2.67 (s, 2H), 2.26 (pt, 2H), 1.27 (s, 6H);

MS (ES$^+$): m/z (%)=572, 574 (100), 501, 503 (MH$^+$, 0.25).

Preparation of 2-(4-Chloro-phenyl)-5-[2,2-dimethyl-4-(4-methyl-piperazin-1-yl)-4-oxo-butyl]-4-thioxo-4,5-dihydro-1-oxa-3b,5-diaza-cyclopenta[a]pentalen-6-one (Compound 16)

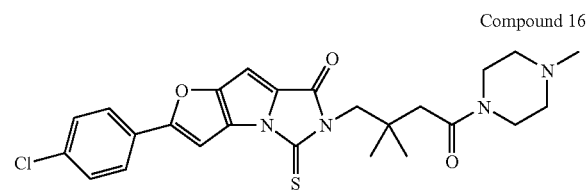

Compound 16

Compound 11 (50 mg, 0.1199 mmol) was reacted with oxalyl chloride (40 μl) as described hereinabove (see, preparation of Compound 14) so as to obtain the chloride of Compound 11.

N-Methyl piperazine (40 μl, 0.36 mmol) was dissolved in ether (1 ml), a HCl ether solution (2 ml, 2 M in ether) was added thereto and the mixture was stirred for 5 minutes until a white solid salt was formed. The solvent was then removed under reduced pressure and the solid salt was added to a solution of the chloride salt of Compound 11 in dichloromethane (5 ml). After completion of the reaction, water and dichloromethane were added and the pH was adjusted to 9 with sodium bicarbonate solution. The layers were separated and the aqueous layer was extracted three times with dichloromethane (15 ml). The combined organic layers were dried over Na$_2$SO$_4$, and the solvents were removed under reduced pressure to give a crude oil, which was purified by column chromatography on a packed silica column, using a 1:1 hexane:ethyl acetate mixture as a eluent, to give Compound 16 (15.4 mg) as a yellow solid.

$^1$H NMR (CDCl$_3$): δ=7.70 (d, 2H), 7.42 (d, 2H), 7.11 (s, 1H), 6.73 (s, 1H), 4.02 (s, 2H), 3.77 (bs, 4H), 2.86, (bs, 4H), 2.63 (s, 3H), 2.37 (s, 2H); 1.20 (s, 6H);

MS (ES$^+$): m/z (%)=499 ([MH]$^+$, (20%).

Preparation of 2-(4-Chloro-phenyl)-5-(2,2-dimethyl-4-morpholin-4-yl-4-oxo-butyl)-4-thioxo-4,5-dihydro-1-oxa-3b,5-diaza-cyclopenta[a]pentalen-6-one (Compound 17)

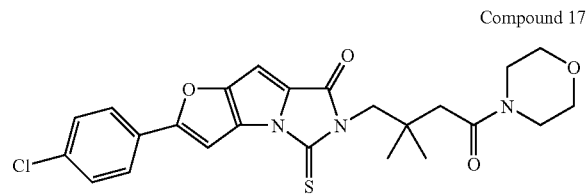

Compound 17

Di-t-butyl dicarbonate, (BOC$_2$O; 218 mg, 1 mmol, 2 molequivalents) was dissolved in dry THF (3 ml) and 3-hydroxy-dihydrobenzotriazinone (HODhbt; 98 mg, 0.6 mmol, 1.2 molequivalents) was added thereto, followed by addition of a yellow solution of Et$_3$N (51 mg, 0.5 mmol, 1 molequivalent) and 4-dimethylaminopyridine (DMAP; 6 mg, 0.05 mmol, 0.1 molequivalents). After 1 hour of stirring at 25° C. the yellow color disappeared and DMAP (25 mg, 0.2 mmol, 0.4 molequivalents) was added followed by addition of a solution of Compound 11 (210 mg, 0.5 mmol) dissolved in dry THF (5 ml). The mixture was stirred at 25° C. for 16 hours while monitoring the reaction progress by TLC using a 6:4 hexane:ethyl acetate mixture as eluent, until the appearance of a less polar spot of the active ester intermediate was observed. The solvent was then evaporated and the residue was dissolved in chloroform (5 ml).

Morpholine (87 mg, 1 mmol, 2 molequivalents) was added and the active ester was consumed after additional 1 hour, as indicated by TLC. Chloroform was thereafter added and the mixture was washed twice with 5% NaHCO$_3$, dried with Na$_2$SO$_4$ and the solvents were evaporated under reduced pressure to give a yellow solid. Crystallization was carried out using ethanol (50 ml) to give Compound 17 (232 mg, 94% yield) as a yellow solid.

$^1$H NMR (CDCl$_3$): δ=7.69 (d, 2H), 7.41 (d, 2H), 7.12 (s, 1H), 6.75 (s, 1H), 4.00 (s, 2H), 3.68 (br t, 4H), 3.64 (br t, 2H), 3.47 (br t, 2H), 2.39 (s, 2H), 1.20 (s, 6H), 1.17 (brs, 6H);

MS (ES$^+$): m/z (%)=508, 510 (MNa$^+$, 42), 486, 488 (MH$^+$, 72), 413 (100), 345 (100), 323 (61).

Preparation of {4-[2-(4-Chloro-phenyl)-6-oxo-4-thioxo-6H-1-oxa-3b,5-diaza-cyclopenta[a]pentalen-5-yl]-3,3-dimethyl-butyrylamino}-acetic acid (Compound 18)

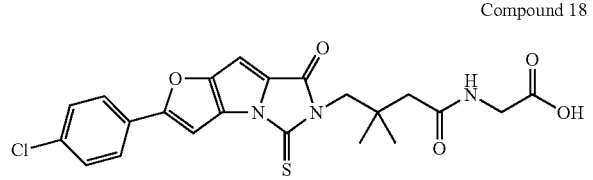

Compound 18

Di-t-butyl dicarbonate, (BOC$_2$O; 218 mg, 1 mmol, 2 molequivalents) was dissolved in dry THF (5 ml) and 3-hydroxy-dihydrobenzotriazinone (HODhbt; 98 mg, 0.6 mmol, 1.2 molequivalents) was added thereto, followed by addition of a yellow solution of Et$_3$N (51 mg, 0.5 mmol, 1 molequivalents) and 4-dimethylaminopyridine (DMAP; 6 mg, 0.05 mmol, 0.1 molequivalents). After 1 hour of stirring at 25° C. the yellow color disappeared and DMAP (25 mg, 0.2 mmol, 0.4 molequivalents) was added followed by addition of Compound 11 (210 mg, 0.5 mmol) as a solid. The mixture was stirred at 25° C. for 16 hours while monitoring the reaction progress by TLC using a 6:4 hexane:ethyl acetate mixture as eluent, until the appearance of a less polar spot of the active ester intermediate was observed.

Chloroform was thereafter added (5 ml), followed by addition of a solution of glycine hydrochloride (223 mg, 2 mmol, 4 molequivalents) and Et$_3$N suspension (404 mg, 4 mmol, 8 molequivalents) in acetonitrile (2 ml), and the reaction was stirred for additional 16 hours, as was indicated by TLC for the complete consumption of the active ester. Chloroform was then added and the mixture was washed twice with 1M HCl, dried over Na$_2$SO$_4$ and the solvents were evaporated under reduced pressure to give an orange solid. Purification was carried out by HPLC using a water:acetonitrile gradient as eluent, to give Compound 18 (202 mg, 85% yield) as a yellow solid.

$^1$H NMR (CDCl$_3$): δ=7.77 (d, 2H), 7.42 (d, 2H), 7.29 (s, 1H), 6.92 (s, 1H), 3.90 (s, 2H), 3.89 (s, 2H), 2.32 (s, 2H), 1.14 (s, 6H);

MS (ES$^+$): m/z (%)=538 and 540 (100), 496, 498 (MNa$^+$, 10), 474, 476 (MH$^+$, 58), 399 and 401 (MH$^+$-Gly-OH, 17).

Preparation of {4-[2-(4-Chloro-phenyl)-6-oxo-4-thioxo-6H-1-oxa-3b,5-diaza-cyclopenta[a]pentalen-5-yl]-3,3-dimethyl-butyrylamino}-acetic acid tert-butyl ester (Compound 19)

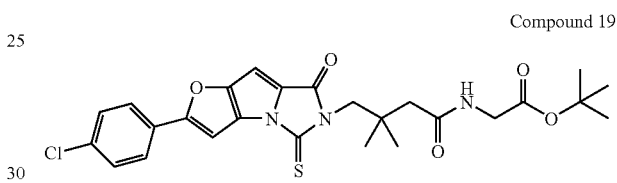

Compound 19

Di-t-butyl dicarbonate, (BOC$_2$O; 109 mg, 0.5 mmol, 2 molequivalents) was dissolved in dry THF (5 ml) and 3-hydroxy-dihydrobenzotriazinone (HODhbt; 49 mg, 0.3 mmol, 1.2 molequivalents) was added thereto, followed by addition of a yellow solution of Et$_3$N (26 mg, 0.25 mmol, 1 molequivalents) and 4-dimethylaminopyridine (DMAP; 3 mg, 0.025 mmol, 0.1 molequivalents). After 1 hour of stirring at 25° C. the yellow color disappeared and DMAP (12 mg, 0.1 mmol, 0.4 molequivalents) was added followed by addition of Compound 11 (105 mg, 0.25 mmol) as a solid. The mixture was stirred at 25° C. for 16 hours, while monitoring the reaction progress by TLC using a 6:4 hexane:ethyl acetate mixture as eluent, until the appearance of a less polar spot of the active ester intermediate was observed.

Chloroform was thereafter added (2.5 ml), followed by addition of glycine tert-butyl ester (65.5 mg, 0.5 mmol, 2 molequivalents) and the mixture was stirred for additional 6 hours. Chloroform was then added and the mixture was washed twice with 2% NaHCO$_3$, twice with 0.2 M HCl, dried over Na$_2$SO$_4$ and the solvents were evaporated under reduced pressure to give a deep-red solid. Purification was carried out by HPLC using a water:acetonitrile gradient as eluent, to give Compound 19 (71 mg, 53% yield) as an orange solid.

$^1$H NMR (CDCl$_3$): δ=7.73 (d, 2H), 7.45 (d, 2H), 7.15 (s, 1H), 6.81 (s, 1H), 4.02 (s, 2H), 4.01 (s, 2H), 2.33 (s, 2H), 1.51 (s, 9H), 1.20 (s, 6H);

MS (ES$^+$): m/z (%)=552 and 554 (MNa$^+$, 48), 530 and 532 (MH$^+$, 25), 496 and 498 (MNa$^+$-(tert-butyl), 18), 474 and 476 (MH$^+$-(tert-butyl), 100).

Preparation of ({4-[2-(4-Chloro-phenyl)-6-oxo-4-thioxo-6H-1-oxa-3b,5-diaza-cyclopenta[a]pentalen-5-yl]-3,3-dimethyl-butyryl}-methyl-amino)-acetic acid methyl ester (Compound 20)

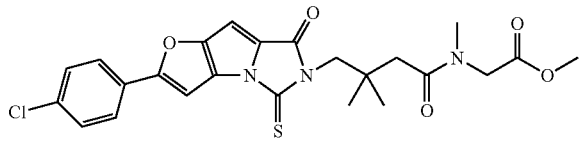

Compound 20

Di-t-butyl dicarbonate, (BOC$_2$O; 218 mg, 1 mmol, 2 molequivalents) was dissolved in dry THF (8 ml) and 3-hydroxy-dihydrobenzotriazinone (HODhbt; 98 mg, 0.6 mmol, 1.2 molequivalents) was added thereto, followed by addition of a yellow solution of Et$_3$N (51 mg, 0.5 mmol, 1 molequivalents) and 4-dimethylaminopyridine (DMAP; 6 mg, 0.05 mmol, 0.1 molequivalents). After 1 hour of stirring at 25° C. the yellow color disappeared and DMAP (25 mg, 0.2 mmol, 0.4 molequivalents) was added, followed by addition of Compound 11 (210 mg, 0.5 mmol) as a solid. The mixture was stirred at 25° C. for 16 hours while monitoring the reaction progress by TLC using a 6:4 hexane:ethyl acetate mixture as eluent, until the appearance of a less polar spot of the active ester intermediate was observed.

Chloroform was thereafter added (6 ml) followed by addition of N-methyl glycine methyl ester hydrochloride (140 mg, 1 mmol, 2 molequivalents), and the reaction reached completion after one additional hour, as indicated by TLC. Chloroform was then added and the mixture was washed twice with 5% NaHCO$_3$, and once with 1M HCl, dried over Na$_2$SO$_4$ and the solvents were evaporated under reduced pressure to give a red solid, which was purified by column chromatography on a packed silica column, using a 6:4 hexane:ethyl acetate mixture as a eluent, to give Compound 20 (212 mg, 84% yield) as a red solid.

$^1$H NMR (CDCl$_3$), isomer 1 (78%): δ=7.69 (d, 2H), 7.41 (d, 2H), 7.12, (s, 1H), 6.75 (s, 1H), 4.14 (s, 2H), 3.99 (s, 2H), 3.74 (s, 3H), 3.09 (s, 3H), 2.48 (s, 2H), 1.21 (s, 6H);

$^1$H NMR (CDCl$_3$), isomer 2 (22%): δ=7.69 (d, 2H), 7.41 (d, 2H), 7.12, (s, 1H), 6.74 (s, 1H), 4.07 (s, 2H), 3.99 (s, 2H), 3.78 (s, 3H), 2.98 (s, 3H), 2.48 (s, 2H), 1.19 (s, 6H);

MS (ES$^+$): m/z (%)=524 and 526 (MNa$^+$, 100), 502 and 504 (MH$^+$, 60), 399 and 401 (MH$^+$-Me-Gly-OMe, 16), 394 (66).

Preparation of ({4-[2-(4-Chloro-phenyl)-6-oxo-4-thioxo-6H-1-oxa-3b,5-diaza-cyclopenta[a]pentalen-5-yl]-3,3-dimethyl-butyryl}-methyl-amino)-acetic acid (Compound 21)

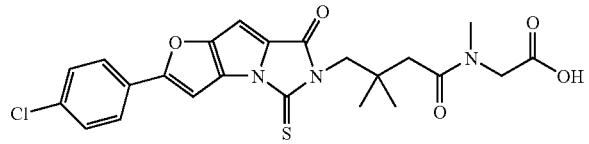

Compound 21

Compound 20 was dissolved in TFA (1.5 ml) and water (0.75 ml) was added thereto. The resulting mixture was stirred at 40° C. for 16 hours. After cooling the mixture to room temperature, water and chloroform were added, followed by addition of 10% NaHCO$_3$ (20 ml), while maintaining an acidic pH of the solution. The organic layer was separated, washed twice with water, dried over Na$_2$SO$_4$ and the solvent was evaporated under reduced pressure to give an orange solid. Chromatography purification was carried out using with a 8:2 ethyl acetate:methanol mixture as eluent to give Compound 21 (38.3 mg, 88% yield) as a yellow solid.

$^1$H NMR (DMSO d$_6$), isomer 1 (68%): δ=7.94 (d, 2H), 7.68 (s, 1H), 7.55 (d, 2H), 7.29 (s, 1H), 3.98 (s, 2H), 3.87 (s, 2H), 3.01 (s, 3H), 2.43 (s, 2H), 1.09 (s, 6H);

$^1$H NMR (DMSO d$_6$), isomer 2 (32%): δ=7.94 (d, 2H), 7.68 (s, 1H), 7.55 (d, 2H), 7.29 (s, 1H), 4.12 (s, 2H), 3.87 (s, 2H), 2.80 (s, 3H), 2.31 (s, 2H), 1.06 (s, 6H);

MS (ES$^+$): m/z (%)=526 and 528 (MK$^+$, 37), 510 and 512 (MNa$^+$, 57), 488 and 490 (MH$^+$, 60), 453 (MH$^+$—Cl, 16), 399 and 401 (MH$^+$-Me-Gly-OH, 100).

Preparation of 1-{4-[2-(4-Chloro-phenyl)-6-oxo-4-thioxo-6H-1-oxa-3b,5-diaza-cyclopenta[a]pentalen-5-yl]-3,3-dimethyl-butyryl}-pyrrolidine-2-carboxylic acid (Compound 22)

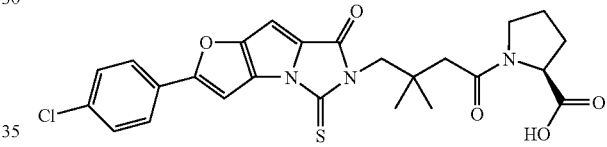

Compound 22

Di-t-butyl dicarbonate, (BOC$_2$O; 218 mg, 1 mmol, 2 molequivalents) was dissolved in dry THF (5 ml) and 3-hydroxy-dihydrobenzotriazinone (HODhbt; 98 mg, 0.6 mmol, 1.2 molequivalents) was added thereto, followed by addition of a yellow solution of Et$_3$N (51 mg, 0.5 mmol, 1 molequivalents) and 4-dimethylaminopyridine (DMAP; 6 mg, 0.05 mmol, 0.1 molequivalents). After 1 hour of stirring at 25° C. the yellow color disappeared and DMAP (25 mg, 0.2 mmol, 0.4 molequivalents) was added, followed by addition of Compound 11 (210 mg, 0.5 mmol) as a solid. The mixture was stirred at 25° C. for 16 hours, while monitoring the reaction progress by TLC using a 6:4 hexane:ethyl acetate mixture as eluent, until the appearance of a less polar spot of the active ester intermediate was observed.

Chloroform was thereafter added (5 ml), followed by addition of a solution of L-proline (115 mg, 1 mmol, 2 molequivalents) and Et$_3$N suspension (202 mg, 2 mmol, 4 molequivalents) in acetonitrile (2 ml), and the reaction was completed after additional 16 hours, as indicated by TLC for the consumption of the active ester. Chloroform was then added and the mixture was washed with water, then with 1M HCl, dried over Na$_2$SO$_4$ and the solvents were evaporated under reduced pressure to give an orange solid. Purification was carried out by HPLC using a water:acetonitrile gradient as eluent, to give Compound 22 (234 mg, 91% yield) as an orange solid.

$^1$H NMR (CD$_3$OD), isomer 1 (78%): δ=7.76 (d, 2H), 7.42 (d, 2H), 7.274 (s, 1H), 6.894 (s, 1H), 4.41 (dd, J=3, 8 Hz, 1H), 3.97 (d, J=14 Hz, 1H), 3.87 (d, J=14 Hz, 1H), 3.66-3.50 (m, 2H), 2.45 (s, 2H), 2.28-2.17 (m, 2H), 2.06-1.89 (m, 2H), 1.19 and 1.15 (s, 6H);

$^1$H NMR (CD$_3$OD), isomer 2 (22%): δ=7.76 (d, 2H), 7.42 (d, 2H), 7.269 (s, 1H), 6.886 (s, 1H), 4.45 (dd, J=3, 8 Hz, 1H), 3.98 (d, J=14 Hz, 1H), 3.85 (d, J=14 Hz, 1H), 3.66-3.50 (m, 2H), 2.45 (s, 2H), 2.28-2.17 (m, 2H), 2.06-1.89 (m, 2H), 1.20 and 1.11 (s, 6H);

MS (ES$^+$): m/z (%)=552 and 554 (MK$^+$, 4), 536 and 538 (MNa$^+$, 34), 514 and 516 (MH$^+$, 100), 399 and 401 (MH$^+$-Pro-OH, 59).

Preparation of 1-{4-[2-(4-Chloro-phenyl)-6-oxo-4-thioxo-6H-1-oxa-3b,5-diaza-cyclopenta[a]pentalen-5-yl]-3,3-dimethyl-butyryl}-pyrrolidine-2-carboxylic acid (Compound 23)

Compound 23

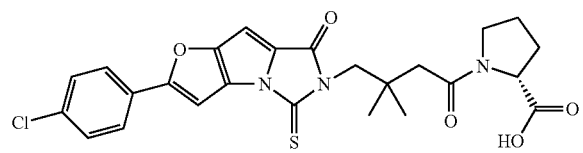

Compound 23 was prepared as described above (see, preparation of Compound 22) using Compound 11 (105 mg, 0.25 mmol) and D-proline (58 mg, 0.5 mmol, 2 molequivalents), to give Compound 23 (86 mg, 67% yield) as an orange solid.

$^1$H NMR (CD$_3$OD), isomer 1 (78%): δ=7.79 (d, 2H), 7.44 (d, 2H), 7.31 (s, 1H), 6.92 (s, 1H), 4.41 (dd, J=3, 8 Hz, 1H), 3.98 (d, J=14 Hz, 1H), 3.88 (d, J=14 Hz, 1H), 3.66-3.50 (m, 2H), 2.46 (s, 2H), 2.29-2.17 (m, 2H), 2.07-1.90 (m, 2H), 1.19 and 1.15 (s, 6H);

$^1$H NMR (CD$_3$OD), isomer 2 (22%): δ 7.79 (d, 2H), 7.44 (d, 2H), 7.31 (s, 1H), 6.91 (s, 1H), 4.49 (dd, J=3, 8 Hz, 1H), 3.99 (d, J=14 Hz, 1H), 3.87 (d, J=14 Hz, 1H), 3.66-3.50 (m, 2H), 2.46 (s, 2H), 2.29-2.17 (m, 2H), 2.07-1.90 (m, 2H), 1.20 and 1.12 (s, 6H);

MS (ES$^+$): m/z (%)=552 and 554 (MK$^+$, 9), 536 and 538 (MNa$^+$, 38), 514 and 516 (MH$^+$, 71), 399 and 401 (MH$^+$-Pro-OH, 100).

Preparation of 2-{1-[2-(4-Chloro-phenyl)-6-oxo-4-thioxo-6H-1-oxa-3b,5-diaza-cyclopenta[a]pentalen-5-ylmethyl]-cyclohexyl}-N,N-diethyl-acetamide (Compound 24)

Compound 24

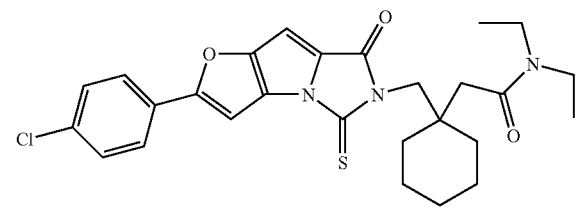

4,4-Pentamethylene-2-pyrrolidinone (765 mg, 5 mmol) was dissolved in acetonitrile (10 ml) and 4-dimethylamino-pyridine (DMAP; 61 mg, 0.5 mmol, 0.1 molequivalents) was added thereto. A solution of di-t-butyl dicarbonate (BOC$_2$O; 1.308 g, 6 mmol, 1.2 molequivalents) in acetonitrile (10 ml) was thereafter added dropwise during 30 minutes, and the resulting mixture was stirred at 25° C., while monitoring the reaction by TLC, using ethyl acetate as eluent and KMNO$_4$ and heating for developing the TLC plate. Stirring was ceased once complete consumption of the pyrrolidinone and appearance of a less polar spot near the front were observed (after about 4 hours). Thereafter, most of the solvent was evaporated under reduced pressure, chloroform was added to the residue and the resulting solution was then washed with 1M HCl, dried over Na$_2$SO$_4$ and the solvents were evaporated under reduced pressure to give 3-oxo-2-aza-spiro[4.5]decane-2-carboxylic acid tert-butyl ester (1.168 grams, 92% yield) as an off-white solid.

3-oxo-2-aza-spiro[4.5]decane-2-carboxylic acid tert-butyl ester (253 mg, 1 mmol) was dissolved in THF (5 ml) and an aqueous solution of 1N LiOH (72 mg/3 ml, 3 molequivalents) was added thereto. The mixture was stirred at 25° C. for 6 hours while monitoring the progress of the reaction by TLC, using a 6:4 hexane:ethyl acetate mixture as eluent and bromocresol for developing the TLC plate. Reaction completion was indicated by the appearance of a more polar spot while the starting material gradually disappeared from the middle of the TLC plate. Thereafter, the THF was evaporated under reduced pressure and the basic aqueous residue was acidified by the addition of 15 drops of concentrated HCl (pH 3) and extracted with ethyl acetate. The aqueous layer was washed with ethyl acetate and the combined organic layer was washed with water, dried over NaSO$_4$ and evaporated under reduced pressure to give [1-(tert-butoxycarbonylamino-methyl)-cyclohexyl]-acetic acid (228 mg, 84% yield) as a colorless solid.

[1-(Tert-butoxycarbonylamino-methyl)-cyclohexyl]-acetic acid (271 mg, 1 mmol) was dissolved in dry dichloromethane (5 ml) and N-(3-dimethylaminopropyl)-N'-ethyl-carbodiimide hydrochloride (EDC-HCl; 576 mg, 3 mmol, 3 molequivalents) and triethylamine (404 mg, 4 mmol, 4 molequivalents) were added thereto. After 10 minutes of stirring, diethylamine (146 mg, 2 mmol, 2 molequivalents) and 4-dimethylamino-pyridine (DMAP; 25 mg, 0.2 mmol, 0.2 molequivalents) were added to the reaction mixture, and the mixture was stirred at 25° C. for 20 hours, while monitoring the reaction by TLC using a 2:8 hexane:ethyl acetate mixture as eluent, and until the appearance of a spot of the amide in the middle of the TLC plate was observed. Chloroform was thereafter added and the mixture was washed with NaHCO$_3$, twice with 1M HCl, dried over Na$_2$SO$_4$ and the solvents were evaporated under reduced pressure to give (1-diethylcarbamoylmethyl-cyclohexylmethyl)-carbamic acid tert-butyl ester (248 mg, 76% yield) as a yellow oil.

(1-Diethylcarbamoylmethyl-cyclohexylmethyl)-carbamic acid tert-butyl ester (320 mg, 0.95 mmol) was dissolved in ethyl acetate (1.5 ml) and a solution of 4N HCl in ethyl acetate (4 ml) was added thereto. The mixture was stirred at 25° C. for 1 hour, and the reaction vessel was thereafter placed in an ice water bath and the reaction mixture was stirred for one additional hour. The mixture was then evaporated to dryness under reduced pressure to give a yellowish solid (228 mg). The crude product was dissolved in water (2 ml) and chloroform (2 ml) was added thereto. Thiophosgene (64 μl, 0.84 mmol, 1 molequivalents) was added to the mixture, followed by addition of NaHCO$_3$ so as to adjust the pH to 7, and the reaction was maintained until the red color disappeared (about 4 hours). Then, chloroform and water were added and the organic and aqueous phases were separated. The aqueous layer was washed with chloroform and the combined organic layer was washed with 1M HCl, dried and evaporated to give N,N-diethyl-2-(1-isothiocyanatomethyl-cyclohexyl)-acetamide (94 mg, 37% yield) as a yellowish oil.

2-(4-Chloro-phenyl)-4H-furo[3,2-b]pyrrole-5-carboxylic acid ethyl ester (15 mg, 0.05 mmol) was prepared as described hereinabove (see, preparation of Compound 4), and placed in a heavy-walled glass tube with a threaded Teflon plug. N,N-diethyl-2-(1-isothiocyanatomethyl-cyclohexyl)-acetamide (84 mg, 0.2 mmol, 4 molequivalents) and $K_2CO_3$ (10 mg, 0.07 mmol, 1.4 molequivalents) were added thereto, the glass tube was sealed and the mixture was heated while stirring at 120° C. for 6 hours. The mixture was then dissolved in chloroform, washed with water, dried over $Na_2SO_4$ and the solvent was evaporated under reduced pressure. The purified product was isolated by HPLC, using an acetonitrile:water gradient as eluent, to give Compound 24 (5.16 mg, 20% yield) as an orange solid.

$^1$H NMR (CDCl$_3$): δ 7.73 (d, 2H), 7.45 (d, 2H), 7.15 (s, 1H), 6.76 (s, 1H), 4.17 (s, 2H), 3.38 (q, 4H), 2.54 (s, 2H), 2.00-1.25 (m, 10H), 1.19 (brs, 6H);

MS (ES$^+$): m/z (%)=534, 536 (MNa$^+$, 0.64), 512, 514 (MH$^+$, 0.95), 443, 445 (33), 319, 321 (100).

Preparation of ethyl 4-[6-oxo-4-thioxo-2-(3-trifluoromethyl-phenyl)-6H-1-oxa-3b,5-diaza-cyclopenta[a]pentalen-5-yl]-butyric acid ethyl ester (Compound 25)

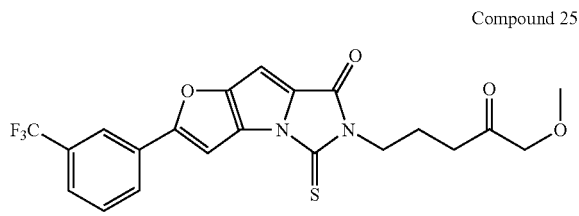

Compound 25

Ethyl azidoacetate was prepared as described above (see, preparation of Compound 1 hereinabove).

A solution of 5-(3-(trifluoromethyl)phenyl)-furfural (300 mg, 1.249 mmol) and ethyl azidoacetate (1.3 grams, 9.99 mmol, 8 molequivalents) in cold toluene (5 ml, 0° C.) was added to a solution of sodium ethoxide (about 10 mmol) in ethanol (6 ml) over a time period of 30 minutes, and the resulting mixture was stirred for another hour while keeping the temperature under 5° C.

To the cooled (0° C.) reaction mixture a solution of ammonium chloride was added and the resulting mixture was poured onto ice-water. The aqueous phase was then extracted twice with ether, the combined organic phase was dried (Na$_2$SO$_4$) and was evaporated under reduced pressure to afford 607 mg of a crude yellow solid. Recrystallization of the crude from ethanol yielded 140 mg of a yellow solid (having a 85% purity, as determined by HPLC). The remaining crude product was purified by column chromatography on silica, using hexane as an eluent, to give 2-azido-3-[5-(3-trifluoromethyl-phenyl)-furan-2-yl]-acrylic acid ethyl ester (35% yield).

$C_{16}H_{12}F_3N_3O_3$ (Mol. Wt.: 351.28) $^1$H NMR (CDCl$_3$): δ=7.91 (bs, 1H), 7.82 (m, 2H), 7.20 (d, J=3.3 Hz, 1H), 6.92 (s, 1H), 6.85 (d, J=4 Hz, 1H), 4.34 (q, 2H), 1.41 (t, 3H);

The isolated 2-azido-3-[5-(3-trifluoromethyl-phenyl)-furan-2-yl]-acrylic acid ethyl ester was heated to 125° C. in p-xylene (5 ml) for 1 hour. The solvent was thereafter evaporated under reduced pressure to give 39.6 mg (96% yield) of 2-(3-trifluoromethyl-phenyl)-4H-furo[3,2-b]pyrrole-5-carboxylic acid ethyl ester as a brownish solid.

$C_{16}H_{12}F_3NO3$ (Mol. Wt.: 323.27);

$^1$H NMR (CDCl$_3$): δ=8.06 (bs 1H), 7.94 (m, 1H), 7.59 (m, 2H), 7.41 (s, 1H), 7.28 (s, 1H), 4.34 (q, 2H), 1.40 (t, 3H).

The isolated 2-(3-trifluoromethyl-phenyl)-4H-furo[3,2-b]pyrrole-5-carboxylic acid ethyl ester (110 mg, 0.34 mmol), 4-isothiocyanato-butyric acid ethyl ester (588 mg, 3.4 mmol) and anhydrous K$_2$CO$_3$ (fine powder, 70.33 mg, 0.51 mmol) were mixed together in a sealed tube, provided with a magnetic stirrer, and the mixture was heated to 110° C. for 5 hours. The mixture was cooled, ethanol was added (5 ml) and the product was filtered and washed with small portions of ethanol. The crude residue was recrystallized from ethanol to afford 124.2 mg of pure Compound 25 (60% yield).

$^1$H-NMR (300 MHz, CDCl$_3$): δ=8.305 (bs, 1H), 7.95 (m, 1H), 7.64 (m, 2H), 7.25 (s, 1H), 6.81 (s, 1H), 4.2 (q, 2H), 4.0 (t, 2H), 2.42 (t, 2H), 2.4 (pent, 2H), 1.28 (t, 3H).

Preparation of ethyl 4-[6-oxo-4-thioxo-2-(3-trifluoromethyl-phenyl)-6H-1-oxa-3b,5-diaza-cyclopenta[a]pentalen-5-yl]-butyric acid (Compound 26)

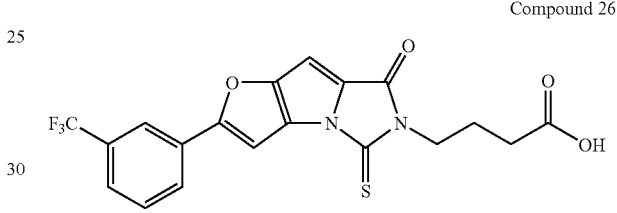

Compound 26

Compound 25 (100 mg, 0.22 mmol, prepared as described hereinabove) was dissolved in a mixture of trifluoroacetic acid and water (4:1; 3 ml) and the solution was heated to 70° C. for 7 hours.

The solution was cooled and allowed to precipitate for one hour. The precipitate was filtered and washed with small portions of ethanol. The crude residue was recrystallized from ethanol and was further purified by preparative HPLC (using a mobile phase of 0.01 TFA in 85% acetonitrile and water) to give 70 mg of pure Compound 26 (80% yield).

$^1$H-NMR (300 MHz, CDCl$_3$): δ=8.05 (bs, 1H), 7.96 (m, 1H), 7.66-7.58 (m, 2H), 7.25 (s, 1H), 6.82 (s, 1H), 4.02 (d, J=6.6 Hz, 2H), 2.51 (d, J=7.5 Hz, 2H), 2.22-2.09 (m, 2H);

MS (ES$^+$): m/z (%)=423 [MH$^+$]

Preparation of {3-[2-(4-chloro-phenyl)-6-oxo-4-thioxo-6H-1-oxa-3b,5-diaza-cyclopenta[a]pentalen-5-yl]-propyl}-phosphonic acid diethyl ester (Compound 27)

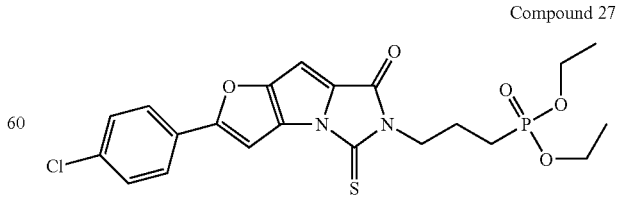

Compound 27

(3-Bromopropyl)phosphonic acid diethyl ester (300 mg, 1.15 mmol) and sodium azide (150 mg, 2.3 mmol) were dissolved in acetone (10 ml) and the solution was refluxed for 12 hours under nitrogen atmosphere, then cooled to room temperature, filtered, and dried under vacuum to afford (3-azidopropyl)phosphonic acid diethyl ester (250 mg, 98% yield) as a colorless liquid.

(3-Azidopropyl)phosphonic acid diethyl ester (240 mg, 1.08 mmol) and activated Pd/C (20 mg) were suspended in methanol (50 ml) and stirred under $H_2$ atmosphere at 40 psi for 3 hours. The black suspension was filtered on Celite, and the solvent was removed under vacuum to give pure (3-aminopropyl)phosphonic acid diethyl ester (205 mg, 99% yield).

$^1$H-NMR (300 MHz, CDCl$_3$): δ=4.13 (m, 4H), 2.85 (t, 2H), 2.42 (s, 2H), 1.81 (m, 2H), 1.35 (t, J=6.9 Hz, 6H).

3-(amino propyl)phosphonic acid diethyl ester (700 mg, 3.59 mmol) was dissolved in chloroform and water (1:1.25, 20 ml), thiophosgene (414 mg, 3.59 mmol) was thereafter added and the resulting mixture was stirred for one minute at room temperature. NaHCO$_3$ powder was added slowly in small portions until a stable neutral pH was reached, and the organic phase was separated. The aqueous layer was extracted three times with chloroform (3×10 ml) and the combined organic phase was dried over Na$_2$SO$_4$ and the solvent was evaporated under reduced pressure. The crude product was purified by silica gel flash chromatography using a methylene chloride:methanol mixture as eluent, to give pure (3-isothiocyanopropyl)phosphonic acid diethyl ester (514 mg, 60% yield).

$^1$H-NMR (300 MHz, CDCl$_3$): δ=4.15 (m, 4H), 3.67 (t, J=6.6 Hz), 1.94-1.84 (m, 4H), 1.36 (t, J=6.9 Hz, 6H);

$^{31}$P-NMR δ:30.5.

2-(4-Chloro-phenyl)-4H-furo[3,2-b]pyrrole-5-carboxylic acid ethyl ester (60.97 mg, 0.21 mmol), prepared by the procedure described above (see, Compound 4), (3-isothiocyanopropyl)phosphonic acid diethyl ester (500 mg, 2.1 mmol) and a fine powder of anhydrous K$_2$CO$_3$ (27.6 mg, 0.2 mmol) were mixed together in a sealed tube, provided with a magnetic stirrer, and the mixture was heated at 110° C. for 2 hours. The mixture was then cooled to room temperature, ethanol (2 ml) was added, and the formed precipitate was filtered. The compound was recrystallized from ethanol to give of Compound 27 (60 mg, 60% yield).

$^1$H-NMR (300 MHz, CDCl$_3$): δ=7.68 (d, 8.4 Hz, 2H), 7.41 (d, 8.4 Hz, 2H), 7.09 (s, 1H), 6.74 (s, 1H), 4.13 (m, 4H), 3.95 (t, 6.9 Hz, 2H), 2.08 (m, 2H), 1.85 (m, 2H), 1.32 (t, 7.2 Hz, 3H).

Preparation of 2-(4-Chloro-phenyl)-5-(3-methoxypropyl)-4-thioxo-4,5-dihydro-1-oxa-3b,5-diaza-cyclopenta[a]pentalen-6-one (Compound 28)

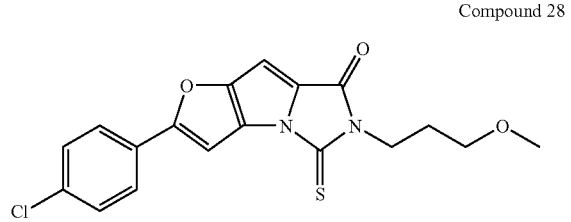

Compound 28

Thiophosgene (1.54 grams, 1.02 ml, 13.4 mmol, 1 molequivalent) was added to a mixture of chloroform (10 ml) and water (20 ml), and a solution of methoxypropylamine (1.19 grams, 1.364 ml, 13.4 mmol) in chloroform (10 ml) was added thereto during 5 minutes. The mixture was stirred vigorously at 25° C. and NaHCO$_3$ was added so as to adjust the pH to 7-8. After 2 hours the pink color disappeared, chloroform and water were added, and the organic and aqueous phases were separated. The aqueous layer was washed with chloroform and the combined organic phase was washed with water, dried over Na$_2$SO$_4$ and the solvents were evaporated under reduced pressure to give 1-isothiocyanato-3-methoxy-propane (578 mg, 33% yield) as yellowish oil. TLC analysis of the product using a 6:4 hexane:ethyl acetate mixture as eluent, indicated a non-polar spot.

2-(4-Chloro-phenyl)-4H-furo[3,2-b]pyrrole-5-carboxylic acid ethyl ester (29 mg, 0.1 mmol) was prepared as described hereinabove (see, preparation of Compound 4), and placed in a heavy-walled glass tube with a threaded Teflon plug. 1-Isothiocyanato-3-methoxy-propane (131 mg, 1. mmol, 10 molequivalents) and triethylamine (202 mg, 2 mmol, 20 molequivalents) were added thereto, the tube was sealed and the mixture was heated while stirring at 120° C. for 6 hours. The mixture was then cooled to room temperature, dissolved in chloroform and the solvents were evaporated under reduced pressure. The crude residue was dissolved in dichloromethane and was purified by column chromatography using a 95:5 hexane:ethyl acetate mixture as eluent, to give Compound 28 (13 mg, 35% yield) as an orange solid.

$^1$H NMR (DMSO d$_6$): δ=7.94 (d, 2H), 7.68 (s, 2H), 7.55 (d, 2H), 7.31 (s, 1H), 3.85 (t, 2H), 3.39 (t, 2H), 1.89 (pent, 2H), 3.22 (s, 3H);

MS (ES$^+$): m/z (%)=397 and 399 (MNa$^+$, 70), 375 and 377 (MH$^+$, 24), 343 and 345 (33), 309 (27), 214 and 216 (80), 158 (100).

Preparation of 2-(4-chloro-phenyl)-5-(1,5-dimethyl-3-oxo-2-phenyl-2,3-dihydro-1H-pyrazol-4-yl)-4-thioxo-4,5-dihydro-1-oxa-3b,5-diaza-cyclopenta[a]pentalen-6-one (Compound 29)

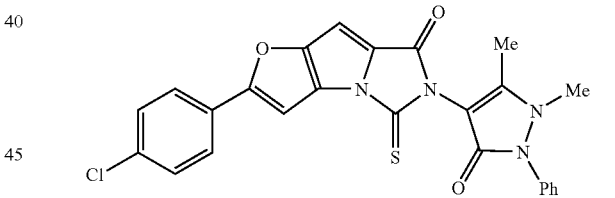

Compound 29

4-Aminoantipyrine (2.03 grams, 10 mmol) was dissolved in chloroform (20 ml) and water (25 ml) was added thereto. thiophosgene (0.84 ml, 11 mmol, 1.1 molequivalents) was then added while vigorously stirring the reaction mixture, followed by addition of sodium bicarbonate (powdered) in small portions until a pH of 7-7.5 was reached and a red brown color developed. The organic phase was then extracted with chloroform and the aqueous layer was washed several times with chloroform. The combined organic phase was dried over Na$_2$SO$_4$ and the organic solvents were evaporated under reduced pressure to give 2.3 grams of 4-isothiocyanatoantipyrine (94% yield).

2-(4-chloro-phenyl)-4H-furo[3,2-b]pyrrole-5-carboxylic acid ethyl ester (64 mg, 0.22 mmol, 1 molequivalent) was prepared as described hereinabove (see, preparation of Compound 4) and was placed in a heavy-walled glass tube with a threaded Teflon plug. 4-isothiocyanatoantipyrine (543 mg, 2.2 mmol, 10 molequivalents) and grinded anhydrous potassium carbonate (61 mg, 0.44 mmol, 2 molequivalents) were added, the glass tube was sealed and the mixture was stirred and heated at 140° C. for 32 hours. Chloroform and with a 5% citric acid solution were then added to the mixture, the organic phase was extracted with chloroform and the aqueous phase was washed with chloroform several times. The combined organic phase was dried over $Na_2SO_4$ and the organic solvents were evaporated under reduced pressure. The crude product was purified by preparative high-pressure liquid chromatography using a water/acetonitrile gradient as a mobile phase, to give 20 mg (19% yield) of Compound 29.

$^1$H NMR (CDCl$_3$): δ=7.757 (d, 2H), 7.643-7.466 (m, 8H), 7.419 (t, 1H), 7.22 (s, 1H), 6.874 (s, 1H), 3.32 (s, 3H), 2.31 (s, 3H).

MS (ES$^+$): m/z (%)=527 and 529 (MK$^+$, 10), 508 and 511 (MNa$^+$, 17), 489 and 491 (MH$^+$, 100).

Preparation of 4-[2-(4-Nitro-phenyl)-4,6-dioxo-6H-1-oxa-3b,5-diaza-cyclopenta[a]pentalen-5-yl]-butyric acid ethyl ester (Compound 30)

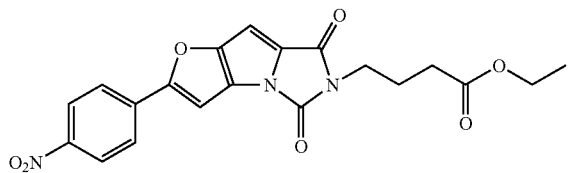

Compound 30

2-(4-Nitro-phenyl)-4H-furo[3,2-b]pyrrole-5-carboxylic acid ethyl ester (25 mg, 0.087 mmol, 1 molequivalent), prepared as described hereinabove (see, preparation of Compound 1), ethyl 4-isocyanatobutyrate (135 mg, 0.87 mmol) and triethylamine (214 μl, 1.74 mmol) were stirred overnight at room temperature. Additional 4-isocyanatobutyrate (130 μl) was added and the mixture was heated to 50° C. and was stirred at this temperature overnight. Once TLC analysis, using a 2:1 hexane:ethyl acetate mixture as eluent, indicated a complete conversion, the crude mixture was purified by column chromatography using a gradient of hexane to hexane:ethyl acetate (9:1) as eluent to give pure Compound 30 (26 mg, 74% yield).

$^1$H NMR (DMSO-d$_6$): δ=8.32 (d, 2H), 8.12 (d, 2H), 7.69 (s, 1H), 7.19 (s, 1H), 4.17 (q, 2H), 4.00 (t, 2H), 2.45, (t, 2H), 2.14 (pent, 2H), 1.31 (t, 3H)

Preparation of 4-[2-(4-nitro-phenyl)-6-oxo-4-thioxo-6H-1-thia-3b,5-diaza-cyclopenta[a]pentalen-5-yl]-butyric acid ethyl ester (Compound 31)

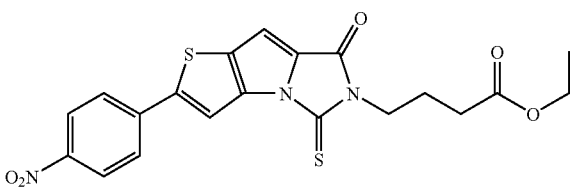

Compound 31

A solution of thiophene-2-carbaldehyde (650 mg, 5.8 mmol) and ethyl azidoacetate (6.89 grams, 53.4 mmol) in dry toluene (40 ml) was added to a cold (−5° C.) solution of sodium ethoxide (about 53 mmol) in ethanol (60 ml) during a time period of one hour, under nitrogen atmosphere. Stirring was continued for another hour while maintaining the temperature under 10° C. The reaction mixture was then cooled to 0° C. and acidified with HCl 0.1 M. After separation of the phases, the aqueous phase was extracted with ether (3×30 ml), the combined organic phase was dried over $Na_2SO_4$ and the organic solvents were evaporated under reduced pressure. The crude product was purified by silica gel flash chromatography to give 718 mg of pure 2-azido-3-thiophen-2-yl-acrylic acid ethyl ester (55% yield).

The resulting azide, 2-azido-3-thiophen-2-yl-acrylic acid ethyl ester (650 mg, 2.88 mmol) was dissolved in toluene (40 ml) and the solution was refluxed for 2 hours. The solution was thereafter cooled, and water (80 ml) was added. After separation of the phases the aqueous phase was extracted with ethyl acetate (3×20 ml), the combined organic phase was dried over $Na_2SO_4$ and the organic solvents were evaporated under reduced pressure. The crude product was purified by silica gel flash chromatography to give 450 mg of pure 4H-thieno[3,2-b]pyrrole-5-carboxylic acid ethyl ester (80% yield).

$^1$H-NMR (300 MHz, CDCl$_3$): δ=9.17 (bs, 1H), 7.32 (d, J=5.1 Hz, 1H), 7.14 (s, 1H), 6.95 (d, J=6.1 Hz, 1H), 4.38 (q, J=7.2 Hz, 2H), 1.39 (t, J=7.2 Hz 3H);

MS (ES$^+$): m/z=226 [M+1]$^+$.

The resulting fused thiophene-pyrrole product, 4H-thieno[3,2-b]pyrrole-5-carboxylic acid ethyl ester (250 mg, 1.28 mmol) and 4-nitro-iodophenol (266 mg, 1.07 mmol) were dissolved in dimethylacetamide (10 ml). Sodium acetate (209.6 mg, 1.6 mmol) and tetrakis-(triphenylphosphine)palladium (61.8 mg, 0.005 mmol) were added thereafter and the reaction mixture was heated at 150° C. while stirring for 24 hours. A solution of HCl 0.1 M (50 ml) and ethyl acetate (20 ml) was then added, the organic and aqueous phases were separated, and the aqueous phase was extracted with ethyl acetate (3×20 ml). The combined organic phase was dried over $Na_2SO_4$ and the organic solvents were evaporated under reduced pressure. The crude product was purified by silica gel flash chromatography to give 105.5 mg of pure 2-(4-nitro-phenyl-4H-thieno[3,2-b]pyrrole-5-carboxylic acid ethyl ester (yield 31.2%).

$^1$H-NMR (300 MHz, CDCl$_3$): δ=9.09 (bs, 1H), 8.29 (d, J=6.9 Hz, 2H), 7.78 (d, J=6.9 Hz, 2H), 7.29 (s, 1H), 7.18 (s, 1H), 4.43 (q, J=7.2 Hz, 2H), 1.43 (t, J=7.2 Hz 3H);

MS (ES$^+$): m/z=317 [M+1]$^+$.

The resulting fused nitrophenylthiophene-pyrrole product 2-(4-nitro-phenyl-4H-thieno[3,2-b]pyrrole-5-carboxylic acid ethyl ester (42 mg, 0.13 mmol), 4-isothiocyanato-butyric acid ethyl ester (230 mg, 1.33 mmol) and finely powdered anhydrous $K_2CO_3$ (27.6 mg, 0.2 mmol) were placed in a sealed tube equipped with a magnetic stirrer, and the mixture was heated while stirring at 110° C. for 5 hours. The reaction mixture was then cooled, absorbed on silica gel, and purified by flash chromatography to give 43 mg of pure Compound 31 (75% yield).

$^1$H-NMR (300 MHz, CDCl$_3$): δ=8.32 (d, J=9.0 Hz, 2H), 7.96 (s, 1H), 7.85 (d, J=9.0 Hz, 2H), 7.08 (s, 1H), 4.16 (q, J=7.2 Hz, 2H), 4.02 (t, J=6.9 Hz, 2H), 2.45 (t, J=7.2 Hz, 2H), 2.14 (m, 2H), 1.29 (t, J=7.2 Hz, 3H);

MS (ES$^+$): m/z (%)=417 (MH$^+$).

Preparation of 4-[2-(4-Nitro-phenyl)-6-oxo-4-thioxo-6H-1-thia-3b,5-diaza-cyclopenta[a]pentalen-5-yl]-butyric acid (Compound 32)

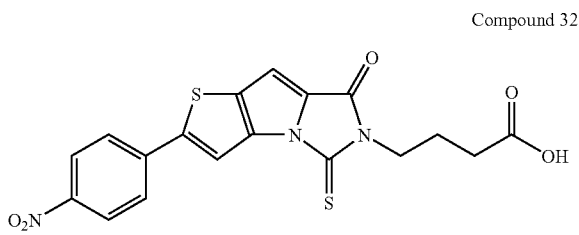

Compound 32

Compound 31 (20 mg, 0.046 mmol) was dissolved in a mixture of TFA and water (4:1, 2 ml) and the resulting solution was heated at 70° C. for 5 hours, while monitoring the reaction progress by TLC using a 6:4 hexane:ethyl acetate mixture as eluent. The mixture was cooled to room temperature and left intact for one hour. The formed precipitate was thereafter filtered and washed with small portions of ethanol. The crude residue was recrystallized from ethanol to give pure Compound 32 (10 mg, 56% yield).

$^1$H-NMR (300 MHz, CDCl$_3$): δ=8.32 (d, 9.0 Hz, 2H), 7.96 (s, 1H), 7.85 (d, 9.0 Hz, 2H), 7.09 (s, 1H), 4.04 (t, 6.9 Hz, 2H), 2.55 (t, 7.2 Hz, 2H), 2.14 (m, 2H);

MS (ES$^+$): m/z (%)=414 [M-H]$^-$.

Preparation of ethyl 4-[2-(4-nitro-phenoxy)-6-oxo-4-thioxo-6H-1-oxa-3b,5-diaza-cyclopenta[a]pentalen-5-yl]-butyric acid ethyl ester (Compound 33)

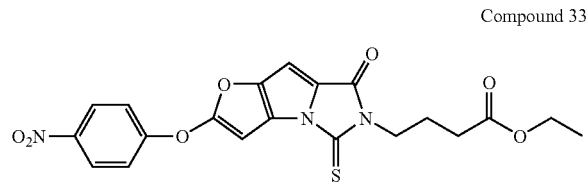

Compound 33

Nitrophenol (43.6 mg, 0.31 mmol) and 5-bromofurfural (50 mg, 0.28 mmol) were dissolved in dry DMF (10 ml), anhydrous K$_2$CO$_3$ (81 mg, 0.39 mmol) was added thereto and the resulting mixture was heated under nitrogen atmosphere at 80° C. for 5 hours. The solvent was then evaporated under reduced pressure and a mixture of water (40 ml) and ether (10 ml) was added. After separation of the phases the aqueous phase was extracted with ether (2×10 ml), the combined organic phase was dried over Na$_2$SO$_4$ and the organic solvents were evaporated under reduced pressure. The crude product was purified by silica gel flash chromatography to give 25 mg of pure 5-(4-nitro-phenoxy)-furan-2-carbaldehyde (38% yield).

$^1$H-NMR (300 MHz, CDCl$_3$): δ=9.52 (s, 1H), 8.33 (d, J=6.9 Hz, 2H), 7.30 (m, 3H), 5.94 (d, J=3.6 Hz, 1H);

MS (ES$^+$): m/z=234 [M+1]$^+$.

Absolute ethanol (20 ml) was added to 5-(4-nitro-phenoxy)-furan-2-carbaldehyde (275 mg, 1.18 mmol) and the mixture was heated to 70° C. until a limpid solution was obtained. Azido-acetic acid ethyl ester (1.827 grams, 14.2 mmol) and DBU (286.9 mg, 1.89 mmol) were then added and the mixture was heated at 70° C. for one and a half hours. The solvent was thereafter removed under reduced pressure and a solution of HCl 0.1 M (50 ml) and ethyl acetate (20 ml) were added. After separation of the phases the aqueous phase was extracted with ethyl acetate (2×20 ml), the combined organic phase was dried over Na$_2$SO$_4$ and the organic solvents were evaporated under reduced pressure. The crude product was purified by silica gel flash chromatography to give 148.5 mg of pure 2-azido-3-(5-(4-nitrophenoxy)-furan-2-yl)-acrylic acid ethyl ester (36.5% yield).

The above obtained product, 2-azido-3-(5-(4-nitrophenoxy)-furan-2-yl)-acrylic acid ethyl ester (20 mg, 0.06 mmol), was dissolved in toluene (20 ml) and the solution was refluxed for 2 hours. The solution was cooled and water (40 ml) was added thereto. After separation of the phases the aqueous phase was extracted with ethyl acetate (2×10 ml), the combined organic phase was dried over Na$_2$SO$_4$ and the solvent was evaporated under reduced pressure. The crude product was purified by silica gel flash chromatography to give 15.2 mg of pure 2-(4-nitro-phenoxy)-4H-furo[3,2-b]pyrrole-5-carboxylic acid ethyl ester (80% yield).

$^1$H-NMR (300 MHz, CDCl$_3$): δ=8.30 (d, J=6.9 Hz, 2H), 7.20 (d, J=6.9 Hz, 2H), 6.83 (s, 1H), 6.05 (s, 1H), 4.37 (q, J=7.2 Hz, 2H), 1.61 (bs, 1H), 1.41 (t, J=7.2 Hz 3H);

MS (ES$^+$): m/z=317 [M+1]$^+$.

The above obtained product, 2-(4-nitro-phenoxy)-4H-furo[3,2-b]pyrrole-5-carboxylic acid ethyl ester (20 mg, 0.06 mmol), 4-isothiocyanato-butyric acid ethyl ester (109.5 mg, 0.63 mmol) and finely powdered anhydrous K$_2$CO$_3$ (13.1 mg, 0.09 mmol) were placed in a sealed tube equipped with a magnetic stirrer and the mixture was heated at 110° C. for 5 hours. The mixture was then cooled, absorbed on silica gel, and purified by flash chromatography to give 15.2 mg of pure Compound 33 (80% yield).

$^1$H-NMR (300 MHz, CDCl$_3$): δ=8.31 (d, J=6.9 Hz, 2H), 7.26 (d, J=6.9 Hz, 2H), 6.76 (s, 1H), 6.39 (s, 1H), 4.17 (q, J=7.2 Hz, 2H), 3.99 (t, J=7.2 Hz, 2H), 2.44 (t, J=7.2 Hz, 2H), 2.11 (pent, J=7.2 Hz, 2H) 1.29 (t, J=7.2 Hz, 3H);

MS (ES$^+$): m/z=444 [M+1]$^+$.

Preparation of 5-(1,1-Dioxo-tetrahydro-thiophen-3-yl)-2-(4-nitro-phenyl-4-thioxo-4,5-dihydro-1-oxa-3b,5-diaza-cyclopenta[a]pentalen-6-one (Compound 34)

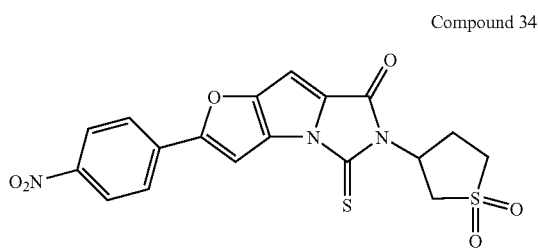

Compound 34

2-(4-Nitrophenyl)-4H-furo[3,2-b]pyrrole-5-carboxylic acid ethyl ester (30 mg, 0.1 mmol, 1 molequivalent), prepared as described hereinabove (see, preparation of Compound 1), is place in a heavy-walled glass tube with a threaded Teflon plug, and 3-isothiocyanato-tetrahydro-thiophene 1,1-dioxide (177 mg, 1.0 mmol, 10 molequivalents) and triethylamine (TEA; 202 mg, 2 mmol, 20 molequivalent) are added thereto. The glass tube is sealed and the mixture is heated at 130° C. while stirring overnight (18 hours). Additional isothiocyanate (10 molequivalents) is then added and stirring is continued at 130° C. for 6 additional hours. Chloroform is then added to the mixture and the purified product is isolated by column chromatography on silica, using a 9:1 hexane:ethyl acetate mixture as eluent, to give Compound 34.

Preparation of 4-[2-(4-Nitro-phenyl)-6-oxo-4-thioxo-6H-1-oxa-3b,5-diaza-cyclopenta[a]pentalen-5-yl]-butyronitrile (Compound 35)

Compound 35

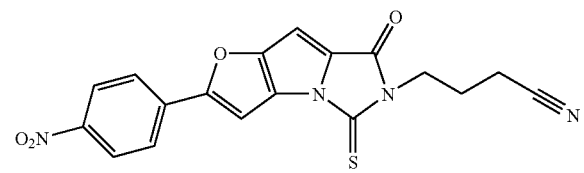

A solution of 4-bromo-butyronitrile (300 mg, 2.02 mmol) and sodium azide (263 mg, 4.05 mmol) in acetone (10 ml) is refluxed for 12 hours under nitrogen atmosphere, cooled to room temperature, filtered, and the solvent is removed under vacuum to give 4-azido-butyronitrile as a colorless liquid.

To a solution of the 4-azido-butyronitrile (3.3 grams, 0.03 mol) and ammonium chloride (3.71 grams, 0.07 mol) in ethyl alcohol (80 ml) and water (27 ml), zinc powder (2.6 grams, 0.04 mol) is added and the mixture is refluxed while vigorously stirring. After the reaction is completed, as indicated by TLC, ethyl acetate (200 ml) and aqueous ammonia (10 ml) are added thereto. The reaction mixture is filtered, and the filtrate is washed with brine, dried over anhydrous sodium sulfate, and the solvent is removed under reduced pressure. The crude residue is purified by a flash chromatography to give 4-amino-butyronitrile.

4-Amino-butyronitrile (500 mg, 5.95 mmol) is dissolved in a mixture of chloroform and water (1:1.25, 40 ml), thiophosgene (684 mg, 5.95 mmol) is added thereto and the mixture is stirred for one minute at room temperature. NaHCO₃ powder is added slowly in small portions until a stable neutral pH is reached. The stirring is then interrupted and the organic phase separated. The aqueous phase is extracted with chloroform (3×10 ml), the combined organic phase is dried over Na₂SO₄ and the solvent is evaporated under reduced pressure. The crude product is purified by silica gel flash chromatography to give 4-isothiocyanato-butyronitrile.

2-(4-nitro-phenyl)-4H-furo[3,2-b]pyrrole-5-carboxylic acid ethyl ester (60.97 mg, 0.21 mmol), prepared as described hereinabove (see, preparation of Compound 1), 4-isothiocyanato-butyronitrile (664 mg, 2.1 mmol) and a fine powder of anhydrous K₂CO₃ (27.6 mg, 0.2 mmol) are mixed together in a sealed tube, provided with a magnetic stirrer, and the mixture is heated at 110° C. for 2 hours. The mixture is cooled to room temperature, ethanol is added (2 ml), and the formed precipitate is filtered. The crude product is recrystallized from ethanol to give Compound 35.

Preparation of 2-(4-Nitro-phenyl)-5-[3-(2H-tetrazol-5-yl)-propyl]-4-thioxo-4,5-dihydro-1-oxa-3b,5-diaza-cyclopenta[a]pentalen-6-one (Compound 36)

Compound 36

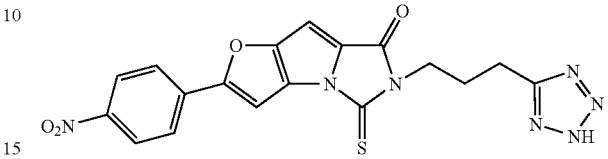

Sodium azide (76 mg, 1.17 mmol) and triethylamine hydrochloride (161 mg, 1.17 mmol) are added to a solution of Compound 35 (462.5 mg, 1.25 mmol) dissolved in DME (15 ml) and the suspension is refluxed for 48 hours. The mixture is then cooled to room temperature and the solvent is removed under reduced pressure. Water (30 ml) and ethyl acetate (30 ml) are added thereto and the aqueous phase is extracted three more times with ethyl acetate. The combined organic extracts are dried over Na₂SO₄ and the solvent is evaporated under reduced pressure. The crude product is recrystallized from ethanol to give Compound 36.

Preparation of 4-[2-(4-Nitro-phenyl)-6-oxo-4-thioxo-6H-1-thia-3,3b,5-triaza-cyclopenta[a]pentalen-5-yl]-butyric acid ethyl ester (Compound 37)

Compound 37

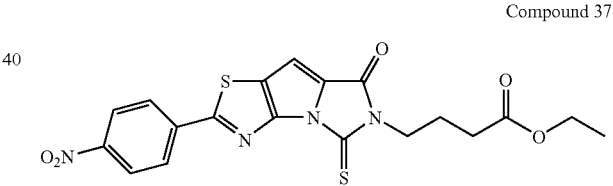

As depicted in Scheme 24 below, anhydrous Co(OAc)₂ (0.021 mmol, 5%) and SALEN (2,2'-(1,4-diiminobutane-1,4-diyl)diphenol, 0.041 mmol, 0.1 molequivalent) in 0.5 ml dry dioxane are placed in a flame-dried flask, and the mixture is stirred for 10 minutes at room temperature. A solution of thiazole (0.411 mmol) in 1 ml dry dioxane, anhydrous Cs₂CO₃ (0.493 mmol, 1.2 molequivalents) and CuI (0.822 mmol, 2 molequivalents) are thereafter added consecutively to the reaction mixture under argon. A solution of 4-nitrophenyl iodide (0.493 mmol, 1.2 molequivalents) in dry dioxane (0.5 ml) is then added dropwise and the resulting mixture is heated to 150° C. under argon, while monitoring the reaction progress by TLC. Once the reaction is completed (after about 10 hours), the resulting mixture is diluted with chloroform (20 ml) and filtered through a celite pad. The organic solvents are evaporated under reduced pressure and the crude product is purified by flash column chromatography, using a hexane:ethyl acetate mixture as eluent, to give pure 2-[4-nitrophenyl] thiazole.

Scheme 24

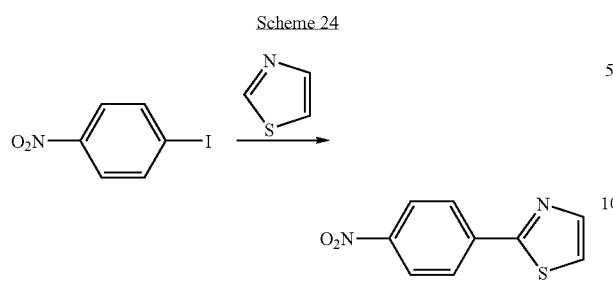

Scheme 26

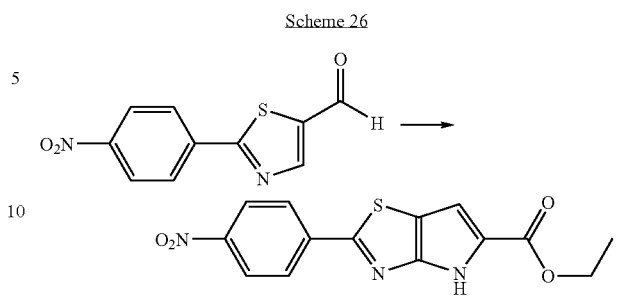

As depicted in Scheme 25 below, 2-(4-nitrophenyl)thiazole (19.9 mmol) dissolved in ether (20 ml) is added dropwise over 1 hour to a stirred and cooled (−78° C.) solution of butyl lithium (1.5 M) in n-hexane (20 ml, 29.9 mmol), diluted with ether (50 ml). The mixture is stirred at −78° C. for 30 minutes and then a solution of N-formylmorpholine (29.9 mmol) in ether (30 ml) is added dropwise over a time period of 15 minutes. After 30 minutes at −78° C., the mixture is washed with saturated aqueous $NaHCO_3$ (30 ml) and extracted with ether (2×20 ml). The organic phase is dried over $Na_2SO_4$ and the solvent is removed under reduced pressure to give the crude 2-(4-Nitro-phenyl)-thiazole-5-carbaldehyde.

As depicted in Scheme 27 below, ethyl 2-(4-nitrophenyl)-4H-pyrrolo[2,3-d]thiazole-5-carboxylate (0.1 mmol) is placed in a heavy-walled glass tube equipped with a threaded Teflon plug, and ethyl 4-isothiocyanatobutyrate (1.03 mmol, 10 molequivalents) and triethylamine (2 mmol, 20 molequivalents) are added thereto. The glass tube is sealed and the reaction mixture is heated at 130° C. while stirring overnight (18 hours). Additional isothiocyanate (10 drops, 10 molequivalents) is added thereafter and heating is continued while stirring at 130° C. for 6 additional hours. The mixture is then dissolved in chloroform and the purified final product is isolated by column chromatography on silica, using a 9:1 hexane:ethyl acetate mixture as eluent.

Scheme 25

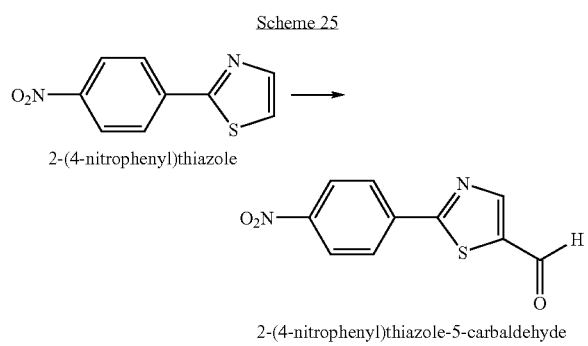

2-(4-nitrophenyl)thiazole 2-(4-nitrophenyl)thiazole-5-carbaldehyde

Scheme 27

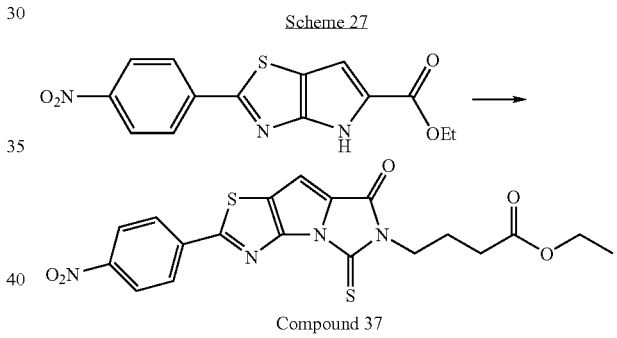

Compound 37

As depicted in Scheme 26 below, dimethoxyethane (DME; 6 ml) is added to the crude 5-(4-nitrophenyl)-thiazole-5-carbaldehyde (0.25 mmol, 1 molequivalent) and the mixture is heated at 75° C. until the solution becomes homogeneous (approximately after 10 minutes). Ethyl azidoacetate (2.2 mmol, 8.6 molequivalents) is added to the hot solution, followed by addition of DBU (0.53 mmol, 2.1 molequivalents), and the mixture is stirred at 75° C. while monitoring the reaction progress by TLC. Once the reaction is completed (within about half an hour, indicated by complete consumption of the starting aldehyde) the product is extracted with chloroform, the chloroform solution is washed twice with 0.1 M HCl, and the combined organic phase is dried over $Na_2SO_4$. The solvent is thereafter evaporated under reduced pressure to give the crude product, which is purified by column chromatography using a 6:4 hexane:dichloromethane mixture as an eluent.

The resulting azido derivative is heated in p-xylene (5 ml) at 145° C. for one hour, and the solvent is thereafter evaporated under reduced pressure to give 2-(4-nitrophenyl)-4H-pyrrolo[2,3-d]-thiazole-5-carboxylic acid ethyl ester.

Preparation of ethyl 4-[2,3-(3-nitro-phenyl)-6-oxo-4-thioxo-6H-1-oxa-3b,5-diaza-cyclopenta[a]pentalen-5-yl]-butyric acid ethyl ester (Compound 38)

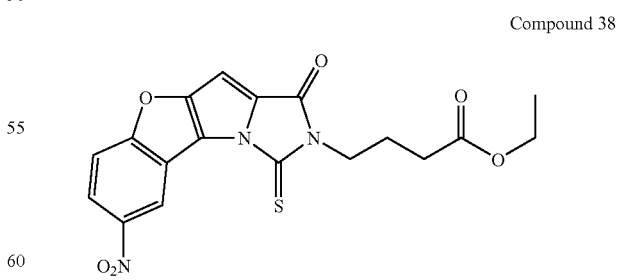

Compound 38

2-Iodo-4-nitrophenol (30 mg, 0.11 mmol) and propargyl alcohol (19 mg, 0.33 mmol) were suspended in a mixture of water (1 ml) and acetonitrile (0.2 ml). Triethylamine (34.3 mg, 0.34 mmol), Pd/C (10%, 2.6 mg, 5.6 μmol), triphenylphosphine (5.9 mg, 22.6 μmol) and copper iodide (2.15 mg, 11.3 µmol) were then added and the heterogeneous mixture was heated at 80° C. while stirring for 3 hours. After cooling the reaction mixture was filtered over celite, and a mixture of water (40 ml) and ethyl acetate (20 ml) was added to the filtrate. After separation of the phases the aqueous phase was extracted with ethyl acetate (2×10 ml) and the combined organic phase was washed with a saturated solution of NaHCO$_3$, then brine, dried over Na$_2$SO$_4$ and the solvent was evaporated under reduced pressure. The crude product was purified by silica gel flash chromatography to give 17.2 mg of pure 4-nitro-benzofuran-2-yl-methanol (78% yield).

$^1$H-NMR (300 MHz, CD$_3$OD): δ=8.54 (d, J=2.4 Hz, 1H), 8.21 (q, J=9.3, 2.4 Hz, 1H), 7.65 (d, J=2.4 Hz 1H), 6.92 (s, 1H), 4.72 (s 1H);

MS (ES$^+$): m/z=194 [M+1]$^+$.

The above obtained product, 4-nitro-benzofuran-2-yl-methanol (110 mg, 0.57 mmol), was dissolved in dry dichloromethane (8 ml) containing a small amount of molecular sieves. Pyridinium chlorochromate (306 mg, 1.42 mmol) was added in portions over a period of ten minutes, and the resulting mixture was stirred under nitrogen atmosphere for 5 hours at room temperature. The suspension was then filtered over celite, and the filtrate was absorbed on silica gel and purified by flash chromatography to give 74.5 mg of pure 4-nitro-benzofuran-2-carbaldehyde (68.5% yield).

$^1$H-NMR (300 MHz, CD$_3$OD): δ=9.94 (s, 1H), 8.59 (d, J=2.4 Hz, 1H), 8.26 (q, J=9.3, 2.4 Hz, 1H), 7.67 (d, J=2.4 Hz 1H), 7.04 (s, 1H), MS m/z (ES$^+$) [M+1]$^+$192.

A solution of 4-nitro-benzofuran-2-carbaldehyde (140 mg, 073 mmol) and ethyl azidoacetate (756 mg, 5.86 mmol) in dry toluene (10 ml) was added to a cold (at −5° C.) solution of sodium ethoxide (about 5.8 mmol) in ethanol (15 ml) over a period of one hour under nitrogen atmosphere. Stirring was continued for an additional hour while maintaining the temperature under 10° C. The solution was then cooled to 0° C. and acidified with 0.1 M HCl solution. After separation of the phases the aqueous phase was extracted with ether (3×30 ml), the combined organic phase was dried over Na$_2$SO$_4$ and the solvent was evaporated under reduced pressure. The crude product was purified by silica gel flash chromatography to give 33 mg of pure 2-azido-3-(4-nitrobenzofuran)-2-yl-acrylic acid ethyl ester (15% yield).

The above obtained product, 2-azido-3-(4-nitrobenzofuran)-2-yl-acrylic acid ethyl ester (30 mg, 0.1 mmol), was dissolved in toluene (10 ml) and the solution was refluxed for 2 hours. The solution was cooled and water (30 ml) was added thereto. After separation of the phases the aqueous phase was extracted with ethyl acetate (3×10 ml), the combined organic phase was dried over Na$_2$SO$_4$ and the solvent was evaporated under reduced pressure. The crude product was purified by silica gel flash chromatography to give 17.5 mg of pure 3H-8-Oxa-3-aza-4-nitro-cyclopenta[α]indene-2-carboxylic acid ethyl ester (65% yield).

$^1$H-NMR (300 MHz, CD$_3$OD): δ=8.66 (d, J=2.4 Hz, 1H) 8.28 (q, J=9.3, 2.4 Hz, 1H), 7.73 (d, J=2.4 Hz 1H), 6.92 (s, 1H), 4.41 (q, J=7.2 Hz, 2H), 1.43 (t, J=7.2 Hz 3H);

MS (ES$^+$): m/z=275 [M+1]$^+$.

The above obtained product, 3H-8-Oxa-3-aza-4-nitro-cyclopenta[a]indene-2-carboxylic acid ethyl ester (10.5 mg, 0.04 mmol), 4-isothiocyanato-butyric acid ethyl ester (230 mg, 0.4 mmol) and finely powdered anhydrous K$_2$CO$_3$ (66 mg, 0.4 mmol) were placed in a sealed tube, equipped with a magnetic stirrer, and the mixture was heated at 110° C. for 2 hours. The mixture was then cooled, absorbed on silica gel, and purified by preparative TLC, using a 7:3 mixture of hexane:ethyl acetate as eluent, to give 10.4 mg of pure Compound 38 (65% yield).

$^1$H-NMR (300 MHz, CDCl$_3$): δ=9.21 (d, J=2.4 Hz, 1H), 8.41 (dd, J=9.0, 2.4 Hz, 1H), 7.72 (d, J=9.0 Hz, 1H), 6.95 (s, 1H), 4.17 (q, J=7.2 Hz, 2H), 4.08 (t, J=6.9 Hz, 2H), 2.48 (t, J=7.2 Hz, 2H), 2.13 (m, 2H), 1.29 (t, J=7.2 Hz, 3H);

MS (ES$^+$): m/z=424 [M$^+$Na]$^+$.

Preparation of 4-[2-(4-Nitro-phenyl)-7-oxo-4-thioxo-4,5-dihydro-7H-1-oxa-3b,5,6-triaza-cyclopenta[a] inden-6-yl]-butyric acid ethyl ester (Compound 41) and its regioisomer ethyl 4-[2-(4-nitro-phenyl)-7-oxo-4-thioxo-6,7-dihydro-1-oxa-3b,5,6-triaza-cyclopenta[a]inden-5-yl]-butyric acid ethyl (Compound 41)

2-(4-Nitro-phenyl)-4H-furo[3,2-b]pyrrole-5-carboxylic acid ethyl ester is prepared from commercially available 5-(4-nitro-phenyl)furfural and ethyl azidoacetate according to the process described hereinabove for the thiazole analog.

As depicted in Scheme 28 below, 2-(4-nitro-phenyl)-4H-furo[3,2-b]pyrrole-5-carboxylic acid ethyl ester (0.1 mmol) is dissolved in 2-propanol (10 ml), hydrazine (0.11 mmol) is added thereto and the mixture is heated to 80° C. and stirred while monitoring the reaction progress by TLC. Once the reaction is completed (the starting material is no longer detected), the pure product, 2-(4-Nitro-phenyl)-4H-furo[3,2-b]pyrrole-5-carboxylic acid hydrazide, is isolated by flash chromatography.

Scheme 28

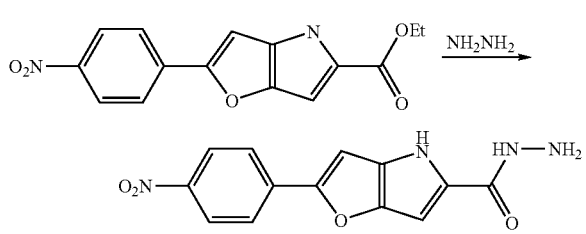

As depicted in Scheme 29 below, a solution of thiophosgen (1.2 molequivalents) in THF is added dropwise at room temperature to a stirred solution of the corresponding hydrazide, 2-(4-nitrophenyl)-4H-furo[3,2-b]pyrrole-5-carbohydrazide, prepared as described hereinabove (1.5 molequivalents), and Na$_2$CO$_3$ in dry THF. The mixture is stirred for 12 hours, and thereafter a mixture of ethyl acetate and water is added. The organic phase is washed with diluted HCl and brine and concentrated wider reduced pressure. The pure product, 2-(4-nitro-phenyl)-4-thioxo-5,6-dihydro-4H-1-oxa-3b,5,6-triaza-cyclopenta[a]inden-7-one, is obtained after purification by flash chromatography.

Scheme 29

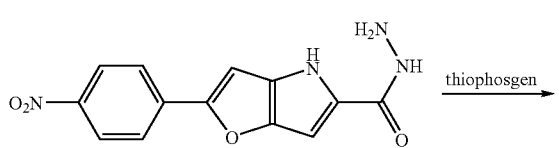

-continued

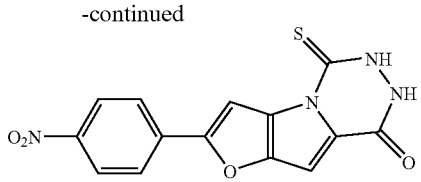

Ethyl bromobutyrate (1 molequivalent) is added in one portion to a solution of 2-(4-nitro-phenyl)-4-thioxo-5,6-dihydro-4H-1-oxa-3b,5,6-triaza-cyclopenta[a]inden-7-one (1.5 molequivalents) in DMF (50 ml). Potassium carbonate (1.5 molequivalents) is then added and the reaction mixture is stirred at room temperature overnight and then heated to 70° C. for 30 minutes. A mixture of ethyl acetate and water is thereafter added, the phases are separated and the aqueous phase is extracted with ethyl acetate. The combined organic phase is washed with water, dried over $Na_2SO_4$ and the solvent is evaporated under reduced pressure to give two isomeric products, as presented in Scheme 30 below. The two isomers, Compound 41 and compound 42 re separated by flash chromatography.

Scheme 30

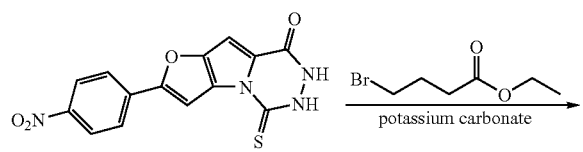

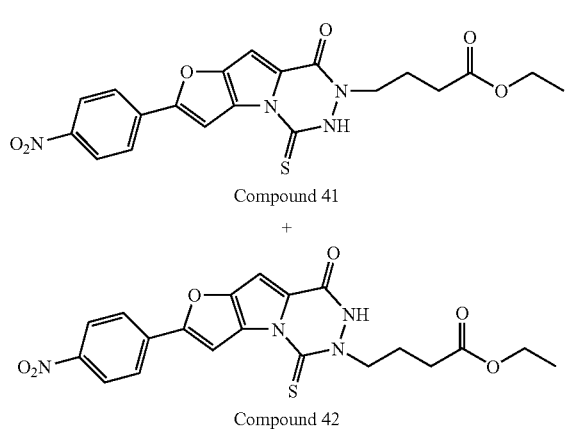

Compound 41

+

Compound 42

Preparation of ethyl 4-[2-(4-nitro-phenyl)-7-oxo-4-thioxo-6,7-dihydro-1-oxa-3b,5,6-triaza-cyclopenta[a]inden-5-yl]-butyric acid ethyl (Compound 42)

2-(4-Nitro-phenyl)-4H-furo[3,2-b]pyrrole-5-carboxylic acid ethyl ester is prepared from commercially available 5-(4-nitro-phenyl)furfural and ethyl azidoacetate as described hereinabove.

As depicted in Scheme 31 below, 2-(4-nitro-phenyl)-4H-furo[3,2-b]pyrrole-5-carboxylic acid ethyl ester (0.1 mmol) is dissolved in 2-propanol (10 ml) and hydrazine (0.11 mmol) is added. The resulting mixture is heated at 80° C., while monitoring the reaction progress by TLC. Once the reaction is completed (the starting material is no longer detected), the solvents are evaporated under reduced pressure, dioxane (20 ml) is added to the crude mixture, followed by addition of ethyl 4-bromobutyrate (0.1 mmol) and triethylamine (0.1 mmol), and the resulting mixture is heated to reflux, while monitoring the reaction progress by TLC. Once the reaction is completed (the starting material is no longer detected), the solvent is evaporated, and a mixture of ethyl acetate and water is added. The phases are separated, and the aqueous phase is extracted with ethyl acetate. The combined organic phase is dried over $Na_2SO_4$, and the solvents are evaporated under reduced pressure to give crude 4-{N'-[2-(4-Nitro-phenyl)-4H-furo[3,2-b]pyrrole-5-carbonyl]-hydrazino}-butyric acid ethyl ester which is purified by column chromatography.

Scheme 31

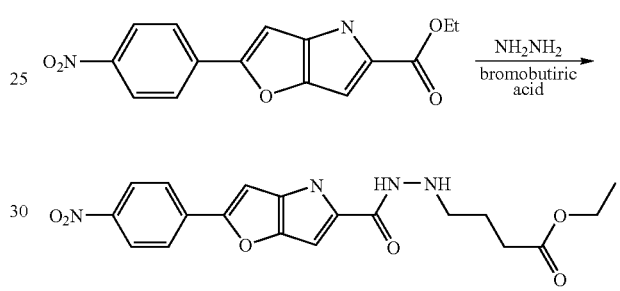

As depicted in Scheme 32 below, a solution of thiophosgen (1.2 molequivalents) in THF is added dropwise, at room temperature, to a stirred solution of ethyl 4-(2-(2-(4-nitrophenyl)-4H-furo[3,2-b]pyrrole-5-carbonyl)hydrazinyl)butanoate (1.5 molequivalents) and $Na_2CO_3$ in dry THF. The mixture is stirred for 12 hours, and thereafter a mixture of ethyl acetate and water is added thereto. The organic phase is washed with diluted HCl and brine and is thereafter concentrated under reduced pressure. The pure product is obtained after purification by flash chromatography.

Scheme 32

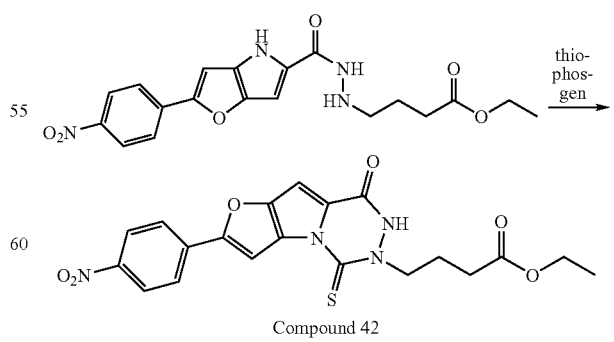

Compound 42

The following describes the preparation of exemplary compounds of the Model Ib subfamily.

Preparation of 4-[5-(4-Nitro-phenyl)-1-oxo-3-thioxo-1H-4-oxa-2,3a-diaza-cyclopenta[a]pentalen-2-yl]-butyric acid ethyl ester (Compound 39)

Compound 39

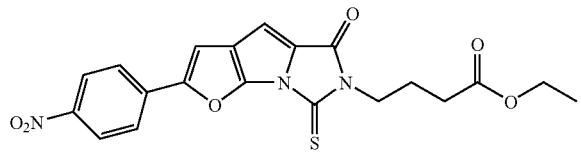

Compound 39 is prepared according to General Procedure IV as described hereinabove.

Preparation of 4-[2-(4-Nitro-phenyl)-5-oxo-7-thioxo-5H-furo[3,2-d]imidazo[1,5-a]imidazol-6-yl]-butyric acid ethyl ester (Compound 40)

Compound 40

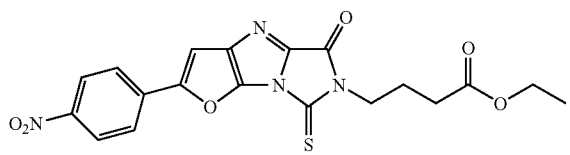

Compound 40 is prepared according to General Procedure V as described hereinabove.

Preparation of Compounds of Model II

Preparation of 3-amino-6-substituted-6H-thiazolo[4,5-c]isothiazole-5-one/thione—General Procedure VI

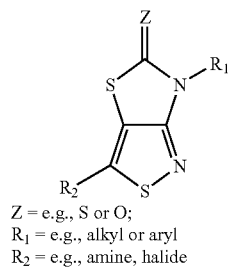

Z = e.g., S or O;
$R_1$ = e.g., alkyl or aryl
$R_2$ = e.g., amine, halide

N-substituted-iso(thio/oxo)cyanate is added to a solution of malononitrile and sulfur in DMF. Triethylamine is added dropwise while maintaining the temperature below 50° C., and monitoring the reaction progress by TLC. Once the reaction is completed the mixture is poured onto ice-water and the product is partially crystallized. After cooling to 4° C. overnight the product is filtered, washed with cooled ethanol and dried to give pure 4-amino-3-substituted-2-oxo/thioxo-2,3-dihydro-thiazole-5-carbonitrile.

4-amino-3-substituted-2-oxo/thioxo-2,3-dihydro-thiazole-5-carbonitrile is added to a solution of triethylamine in DMF and $H_2S$ is vigorously bubbled through the mixture. The reaction mixture is then stirred for one additional hour until complete conversion is indicated by TLC or HPLC analysis. The reaction mixture is then poured onto an ice-water mixture and maintained at 4° C. overnight. Thereafter the obtained precipitate is filtered, washed with water and subsequently with ether and then dried to give 4-Amino-3-substituted-2-oxo/thioxo-2,3-dihydro-thiazole-5-carbothioic acid amide.

An excess of iodine ($I_2$) in ethanol is added dropwise to a stirred solution of 4-amino-3-substituted-2-oxo/thioxo-2,3-dihydro-thiazole-5-carbothioic acid amide in ethanol, at 25° C., while monitoring the reaction progress by TLC. Once the reaction is completed, a solution of $Na_2S_2O_3$ is added, so as to remove excess of $I_2$, and the resulting solution is neutralized with a 5% solution of $NaHCO_3$. A mixture of water and ethyl acetate is added thereafter, phases are separated and the aqueous phase is extracted with ethyl acetate. The combined organic extracts are washed with brine, dried over $Na_2SO_4$ and the solvents are evaporated under reduced pressure to give a crude product, which is precipitation in acetonitrile to give 3-amino-6-substituted-6H-thiazolo[4,5-c]isothiazole-5-one/thione.

Preparation of 6-substituted-3-(5-substituted-furan-2-yl)-6H-thiazolo[4,5-c]isothiazole-5-one/thione— General Procedure VII

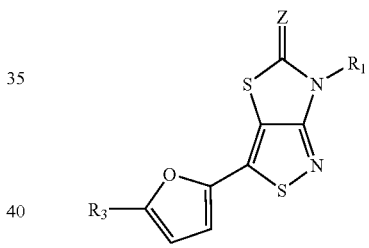

Z = e.g., S or O;
$R_1$ = e.g., alkyl or aryl
$R_3$ = e.g., alkyl or aryl

3-Amino-6-substituted-6H-thiazolo[4,5-c]isothiazole-5-one/thione is dissolved in dry acetonitrile, under nitrogen atmosphere, and the solution is cooled to −10° C. Nitrosyltetrafluoroborate ($NOBF_4$) in dry acetonitrile is then added. The mixture is stirred for one hour at −10° C., and a mixture of 2-substituted-furan and $CuCl_2$ dihydrate in acetonitrile (1 ml) is thereafter added dropwise. The resulting mixture is allowed to warm to 0° C., and stirring continues while monitoring the reaction by TLC. Once the reaction is completed, a mixture of ethyl acetate and water is added, and after separation of the phases the organic phase is dried over $Na_2SO_4$, and the solvent is evaporated under reduced pressure to give the crude product. Purification by column chromatography using fine silica and a 4:1 hexane:ethyl acetate mixture as eluent gives 6-substituted-3-(5-substituted-furan-2-yl)-6H-thiazolo[4,5-c]isothiazole-5-one/thione.

The following describes the preparation of exemplary compounds of the Model II subfamily.

111

Preparation of ethyl 4-(3-amino-5-thioxo-thiazolo[4,5-c]isothiazol-6-yl)-butyric acid ethyl ester (Compound 43)

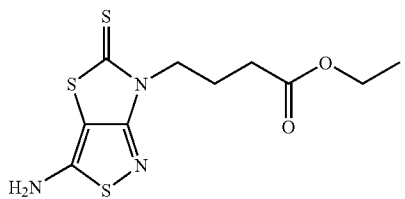

Compound 43

Compound 43 was prepared according to the procedure described in German Patent No. DE 152937, as depicted in Scheme 33 below. Ethyl 4-isothiocyanatobutyrate (236 μl, 1.513 mmol) was added to a solution of malononitrile (100 mg, 1.513 mmol) and sulfur (48.5 mg, 1.513 mmol) in DMF (20 ml). Triethylamine (210 μl, 1.513 mmol) was added dropwise while maintaining the temperature below 50° C., and the reaction progress was monitored by TLC. Once the reaction was completed (after about one and a half hours) the mixture was poured onto ice-water and the product was partially crystallized. After cooling to 4° C. overnight the product was filtered, washed with cooled ethanol and dried to give pure 4-(4-amino-5-cyano-2-thioxo-thiazol-3-yl)-butyric acid ethyl ester [$C_{10}H_{13}N_3O_2S_2$ (271)] as a light yellow solid (47% yield).

$^1$H NMR (CDCl$_3$): δ=6.04 (bs, 2H, NH$_2$), 4.21 (m, 4H), 2.49 (t, 2H), 1.97 (m, 2H); 1.31 (t, 3H);

MS (ES$^+$): m/z (%)=294 ([M+Na]$^+$, 50.4), 272 (MH$^+$, 91.5), 226 (100).

4-(4-Amino-5-cyano-2-thioxo-thiazol-3-yl)-butyric acid ethyl ester (1.947 mg, 7.18 mmol) was added to a solution of triethylamine (1 ml, 7.18 mmol) in DMF (50 ml). H$_2$S was vigorously bubbled through the mixture until the solution became green. The reaction mixture was then stirred for one additional hour until complete conversion was indicated by HPLC analysis. The reaction mixture was poured thereafter onto ice-water, the resulting mixture was cooled at 4° C. overnight and the obtained precipitate was filtered, washed with water, then with ether and then dried to give pure 4-(4-amino-5-thiocarbamoyl-2-thioxo-thiazol-3-yl)-butyric acid ethyl ester [$C_{10}H_{15}N_3O_2S_3$ (Mol. Wt. 305)] as a yellow solid (90% yield).

$^1$H NMR (DMSO): δ=8.96 (s, 2H), 8.26 (bs, 2H, NH$_2$), 4.22 (t, 2H), 4.03 (q, 2H), 2.38 (t, 2H), 1.88 (m, 2H); 1.17 (t, 3H);

MS (ES$^+$): m/z (%)=328 ([M+Na]$^+$, 28), 306 (MH$^+$, 100), 289 (54).

An excess of iodine (I$_2$) in ethanol was added dropwise to a stirred solution of 4-(4-amino-5-thiocarbamoyl-2-thioxo-thiazol-3-yl)-butyric acid ethyl ester (360 mg, 1.18 mmol) in ethanol (25 ml), at 25° C., while monitoring the reaction progress by TLC. Once the reaction was completed, (upon stirring overnight at 25° C.), a solution of Na$_2$S$_2$O$_3$ was added, so as to remove excess of I$_2$, and the resulting solution was neutralized with a 5% solution of NaHCO$_3$. A mixture of water and ethyl acetate was added thereafter, phases were separated and the aqueous phase was extracted with ethyl acetate. The combined organic extracts were washed with brine, dried over Na$_2$SO$_4$ and the solvents were evaporated under reduced pressure to give yellow oil. Precipitation in acetonitrile gave 342 mg of Compound 43 (95% yield).

112

$^1$H NMR (CDCl3): δ=4.57 (bs, 2H), 4.33 (t, 2H), 4.1 (q, 2H), 2.4 (t, 2H), 2.15 (m, 2H); 1.23 (t, 3H);

MS (ES$^+$): m/z (%)=326 ([M+Na]$^+$, 68), 304 (MH$^+$, 80), 258 (10).

Scheme 33

Preparation of ethyl 4-(3-iodo-5-thioxo-thiazolo[4,5-c]isothiazol-6-yl)-butyric acid ethyl ester (Compound 44)

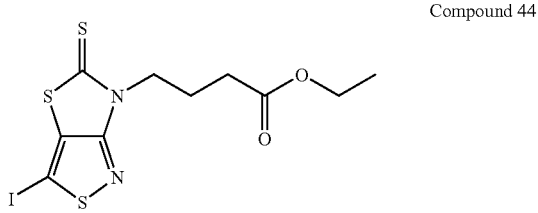

Compound 44

Compound 43 (280 mg, 0.925 mol) was suspended in 270 μl HCl (12 M) and water (400 μl). After stirring for 15 minutes the solution was cooled to 0° C. and sodium nitrite (127.6 mg, 1.85 mmol), dissolved in 1 ml water, was added dropwise. Stirring was continued for additional half an hour while maintaining the temperature below −5° C. Potassium iodide (307 mg, 1.85 mmol) dissolved in 1 ml water was added to the resulting mixture, which then turned dark brown. The reaction mixture was allowed to warm to 25° C. and stirring was continued overnight. Ethyl acetate was thereafter added, the phases were separated and the aqueous phase was further extracted with ethyl acetate. The combined organic phase was dried over $Na_2SO_4$, and the solvent was evaporated under reduced pressure to give 450 mg of the crude product. Purification by column chromatography using fine silica and a 4:1 hexane:ethyl acetate mixture as eluent gave 50 mg of Compound 44 (13% yield) as a white solid.

MS (ES⁺): m/z (%)=437 (M+Na, 100), 415 (MH⁺, 58.5), 369 (67.5).

Preparation of 4-{3-[5-(4-nitro-phenyl)-furan-2-yl]-5-thioxo-thiazolo[4,5-c]isothiazol-6-yl}-butyric acid ethyl ester (Compound 45)

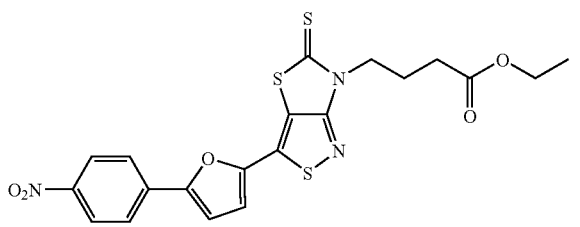

Compound 45

As depicted in Scheme 34 below, Compound 43 (30 mg, 0.2 mmol) was dissolved in dry acetonitrile (2 ml), under nitrogen atmosphere, and the solution was cooled to −10° C. Nitrosyltetrafluoroborate ($NOBF_4$, 28 mg, 0.24 mmol) in dry acetonitrile (1 ml) was then added and the resulting mixture immediately turned red. The mixture was stirred for one hour at −10° C., and a mixture of 2-(4-nitrophenyl) furan (75 mg, 0.4 mmol) and $CuCl_2$ dihydrate (5 mg) in acetonitrile (1 ml) was thereafter added dropwise. The resulting mixture was allowed to warm to 0° C., and stirring was continues while monitoring the reaction by TLC. Once the reaction was completed (after about one hour), a mixture of ethyl acetate and water was added, and after separation of the phases the organic phase was dried over $Na_2SO_4$, and the solvent was evaporated under reduced pressure to give 130 mg of the crude red product. Purification by column chromatography using fine silica and a 4:1 hexane:ethyl acetate mixture as eluent gave 16 mg of Compound 45 as a red oily solid (15-20% yield). The product was further purified by preparative HPLC using an acetonitrile:water gradient as a mobile phase.

¹H NMR (CDCl₃): δ=8.33 (d, 2H), 8.03 (d, 2H), 7.27 (d, 2H), 7.24 (d, 2H), 4.46 (t, 2H), 4.12 (q, 2H), 2.24 (t, 2H), 2.15 (m, 2H); 1.23 (t, 3H);

MS (ES⁺): m/z (%)=498 (M+Na, 41), 476 (MH⁺, 31.5), 447 (46).

Scheme 34

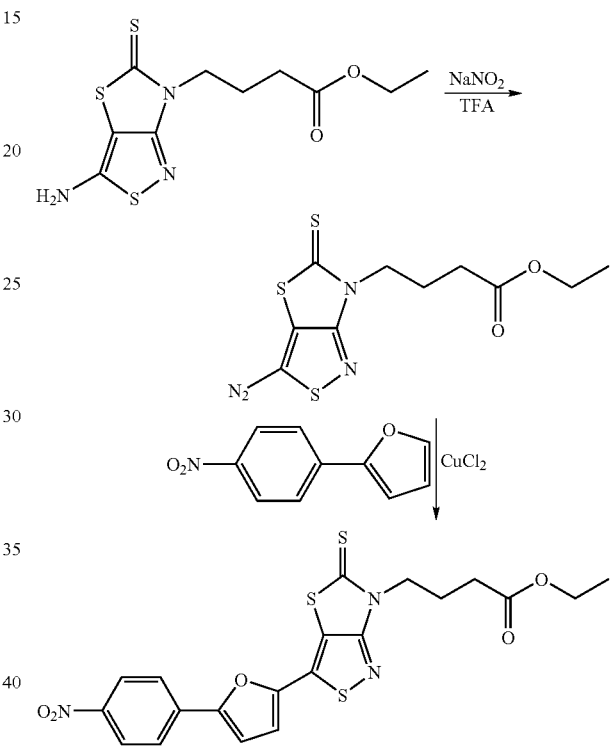

Preparation of Compounds of Model III

The following describes the preparation of exemplary compounds of the subfamily presented by Model III above.

Preparation of 4-(6-phenyl-4-thioxo-7-oxa-1-thia-2,3,4a-triaza-dicyclopenta[a,cd]pentalen-3-yl)-butyric acid ethyl ester (Compound 46)

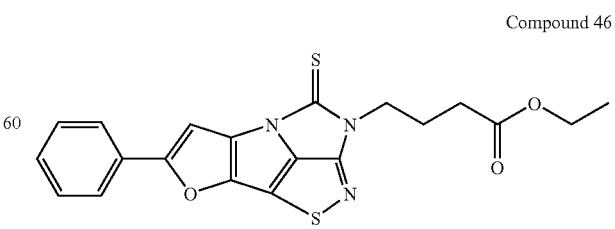

Compound 46

As depicted in Scheme 35 below, 2-phenyl-4,5-dihydro-furo[3,2-c]pyridine-6-carboxylic acid (0.015 mol) is added in portions to a mixture of sodium hydride (60% dispersion in mineral oil, 0.045 mol) in anhydrous DMF (35 ml) under a nitrogen stream at 0° C. After 15 minutes phenylacetyl disulfide (0.02 mol) is added portion-wise, and the reaction is then heated to 50° C. and kept at that temperature overnight. The reaction mixture is then cooled to room temperature and poured onto crushed ice, turned acidic with 2N HCl, and extracted with ethyl acetate. The organic phase is separated, washed with brine, and dried over Na$_2$SO$_4$. The solvent is evaporated under reduced pressure and the obtained residue is triturated with hexane and filtered. The obtained crude residue is then refluxed in the presence of HCl 6N and water to give 7-mercapto-2-phenyl-4,5-dihydro-furo[3,2-c]pyridine-6-carboxylic acid.

Scheme 35

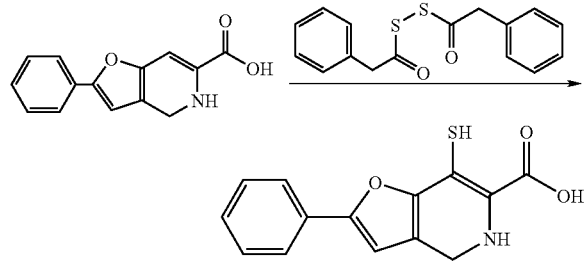

As depicted in Scheme 36 below, 7-mercapto-2-phenyl-4,5-dihydro-furo[3,2-c]pyridine-6-carboxylic acid is then refluxed in the presence of thionyl chloride (SOCl$_2$) and catalytic amount of pyridine for a few hours, while monitoring the reaction progress by TLC. Once the reaction is completed, the thionyl chloride is evaporated under reduced pressure, the product is dissolved in DMF (20 ml), and ammonia gas is bubbled through the solution at 0° C. for one hour. The reaction is thereafter quenched on crushed ice and extracted with ethyl acetate. The organic phase is washed with brine, dried over Na$_2$SO$_4$, and the solvent is evaporated under reduced pressure to give a crude product. Purification by silica gel column chromatography gives (Z)-ethyl 4-(amino (6-mercapto-2-phenyl-4H-furo[3,2-b]pyrrol-5-yl)methyl-eneamino)butanoate.

Scheme 36

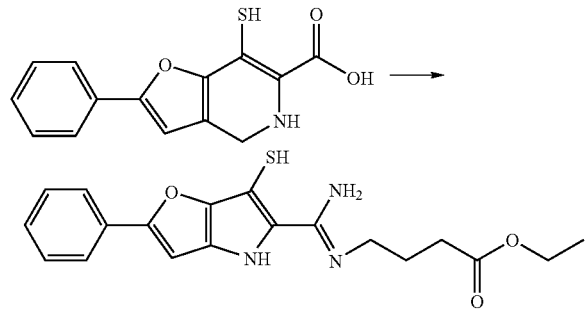

Hydrogen peroxide (30%, 0.05 mol) is then added dropwise at 40° C., and after one hour the reaction mixture is cooled to room temperature and poured into water, and 4-(5-Phenyl-7H-4-oxa-3-thia-2,7-diaza-cyclopenta[a]pentalen-1-ylamino)-butyric acid ethyl ester is collected by filtration.

Scheme 37

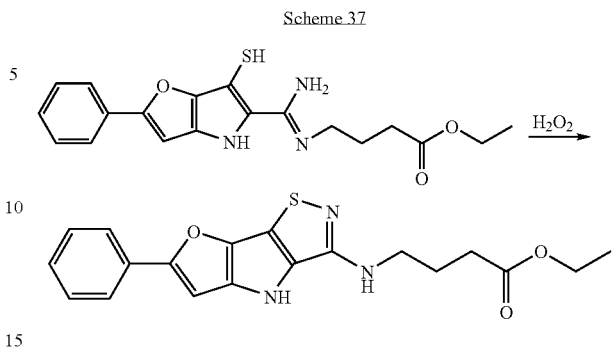

As depicted in Scheme 38 below, 4-(5-phenyl-7H-4-oxa-3-thia-2,7-diaza-cyclopenta[a]pentalen-1-ylamino)-butyric acid ethyl ester (0.01 mol) is added to a mixture of water and chloroform (1:1), and the mixture is vigorously stirred to form a suspension. A solution of thionyl chloride (CSCl$_2$, 0.011 mol) in chloroform is added to the suspension and NaHCO$_3$ is added thereafter until the pH is about 7.5. After one hour of stirring the phases are separated and the aqueous layer is extracted with chloroform. The combined organic phase is dried over Na$_2$SO$_4$ and the solvent is evaporated under reduced pressure to give a crude 4-(6-phenyl-4-thioxo-7-oxa-1-thia-2,3,4a-triaza-dicyclopenta[a,cd]pentalen-3-yl)-butyric acid ethyl ester (Compound 46) which is purified by column chromatography.

Scheme 38

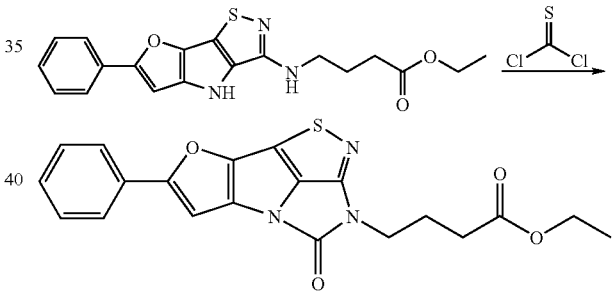

Preparation of Compounds of Model IV

Preparation of 4-(6-(4-nitrophenyl)-2-thioxo-7-oxa-1-thia-3,4-diaza-s-indacen-3-yl)-butyric acid (Compound 47)

Compound 47

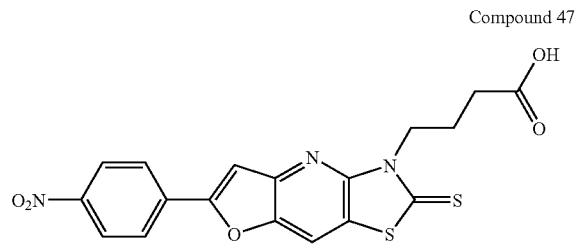

3-Bromo-2-formylfuran (5 grams, 0.29 mol) of and sodium azide (5 grams, 0.077 mol) are dissolved in dimethyl sulfoxide (DMF, 100 ml). The reaction mixture was slowly stirred for 48 hours at 65° C., and thereafter cooled and poured into water (150 ml). The solution is extracted with ether (4×30 ml), and the combined ether phase is dried over magnesium sulfate and evaporated under reduced pressure to dryness. The crude mixture is purified by chromatography column packed with silica using a gradient of hexane to hexane:ethyl acetate (5:1) as eluent. The pure product was obtained as yellow solid (45%).

3-Azido-2-formylfuran (200 mg, 1.458 mmol) was dissolved in dry ether and triphenylphosphine (383 mg, 1.458 mmol) was added thereto. The mixture was stirred at room temperature for 30 minutes and a white solid precipitated was formed. The solid was filtered to give 3-imino(triphenyl) phosphorane-furan-2-carbaldehyde (90% yield) as a pure solid.

$^1$H-NMR (CDCl$_3$): δ=7.6-7.8 (m, 15H), 7.51 (s, 1H), 7.42 (d, 1H), 5.94 (d, 1H), 4.14 (t, 2H), 2.39 (t, 2H), 2.01 (t, 2H);

MS (ES$^+$): m/z (%)=573 (MH)$^+$ (49%).

3-Imino(triphenyl)phosphorane-furan-2-carbaldehyde (19.3 mg, 0.052 mmol), 4-(4-oxo-2-thioxo-thiazolidin-3-yl)-butyric acid (12 mg, 0.0.52 mmol) and Et$_3$N (15 µl, 0.104 mmol) were dissolved in xylene (5 ml) and the mixture was heated slowly to 100° C. for one hour, and then heated to 150° C. for three additional hours. The product, 4-(2-thioxo-7-oxa-1-thia-3,4-diaza-s-indacen-3-yl)-butyric acid, was purified by preparative HPLC using an acetonitrile:water mixture containing 0.01% TFA as eluent, to give a yellowish solid.

MS (ES$^+$): m/z (%)=317 (M+K)$^+$, 301 (M+Na)$^+$, 279 (MH)$^+$.

4-(2-Thioxo-7-oxa-1-thia-3,4-diaza-s-indacen-3-yl)-butyric acid (0.2 mmol) was dissolved in dry acetonitrile (2 ml) under nitrogen atmosphere, and the solution was cooled to −10° C. Nitrosyltetrafluoroborate (NOBF$_4$, 0.24 mmol) mixed in dry acetonitrile (1 ml) was added thereto, and the mixture turned red immediately. The resulting mixture was stirred for one hour at −10° C., and a mixture of nitrobenzene (0.4 mmol) and a solution of CuCl$_2$ dihydrate (15 mmol) in acetonitrile (1 ml) was added dropwise. The reaction mixture was allowed to warm-up to 0° C., and TLC analysis using a 1:1 hexane:ethyl acetate mixture as eluent indicated complete conversion after 0.5-1.0 hours. Thereafter ethyl acetate and water were added, the organic and aqueous layers were separated, the organic layer was dried over Na$_2$SO$_4$ and the solvent was evaporated under reduced pressure to give the crude product 4-[6-(4-nitro-phenyl)-2-thioxo-7-oxa-1-thia-3,4-diaza-s-indacen-3-yl]-butyric acid which was further purified by column chromatography using fine silica and a 4:1 hexane:ethyl acetate mixture as eluent.

Scheme 39

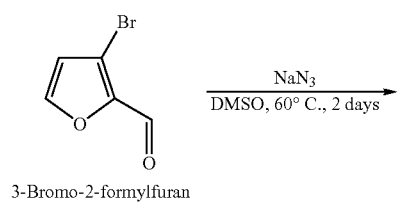

3-Bromo-2-formylfuran

-continued

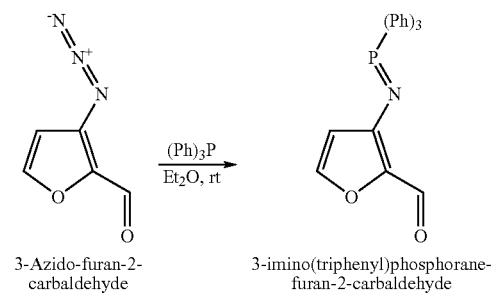

3-Azido-furan-2-carbaldehyde 3-imino(triphenyl)phosphorane-furan-2-carbaldehyde

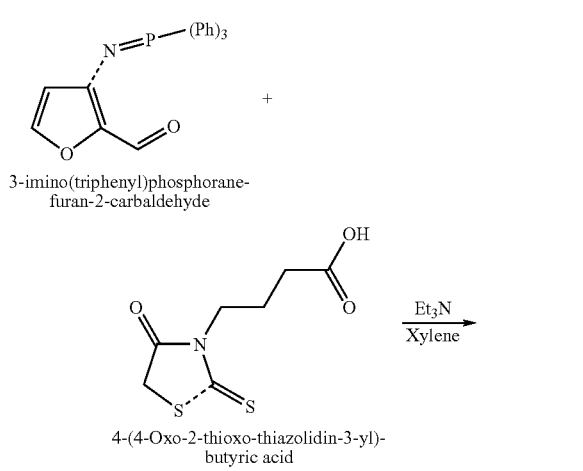

3-imino(triphenyl)phosphorane-furan-2-carbaldehyde 4-(4-Oxo-2-thioxo-thiazolidin-3-yl)-butyric acid

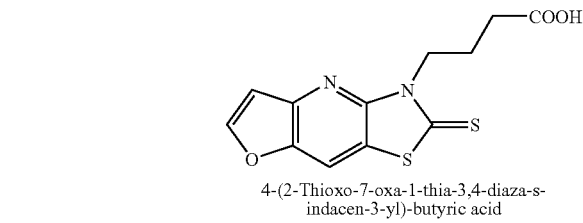

4-(2-Thioxo-7-oxa-1-thia-3,4-diaza-s-indacen-3-yl)-butyric acid

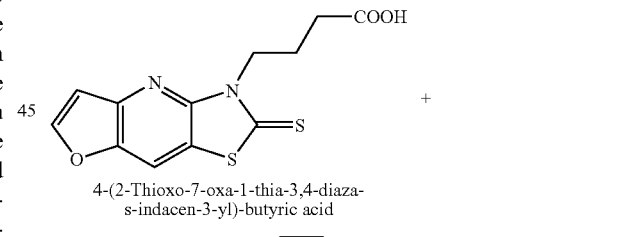

4-(2-Thioxo-7-oxa-1-thia-3,4-diaza-s-indacen-3-yl)-butyric acid

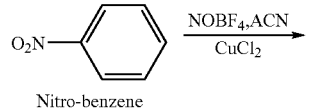

Nitro-benzene

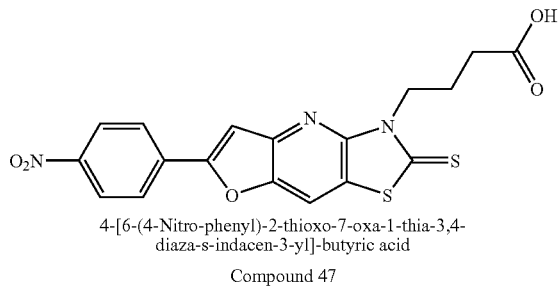

4-[6-(4-Nitro-phenyl)-2-thioxo-7-oxa-1-thia-3,4-diaza-s-indacen-3-yl]-butyric acid Compound 47

Preparation of 4-[2-(4-Chloro-phenyl)-4,7-dioxo-5-thioxo-4,7-dihydro-1-oxa-4a,6-diaza-s-indacen-6-yl]-butyric acid ethyl ester (Compound 48)

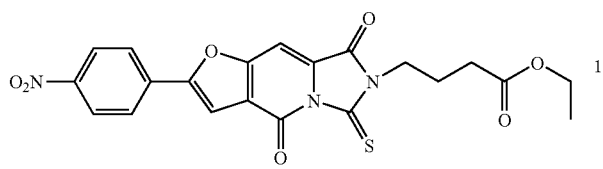

Compound 48

As depicted in Scheme 40 below, 2-thiohydantoin (1.4 grams, 12 mmol) was dissolved in DMF (50 ml) and ethyl bromobutyrate (0.48 ml, 3.4 mmol, 0.28 molequivalents) and $K_2CO_3$ (2.07 grams, 15 mmol, 1.5 molequivalents) were added thereto. The mixture was stirred at room temperature for 2 hours and then additional ethyl bromobutyrate (0.48 ml, 3.4 mmol, 0.28 molequivalents) was added and the reaction mixture was stirred for 16 hours until all starting material was consumed, as indicated by TLC. Thereafter methylene chloride was added followed by addition of water, the organic phase was extracted, the aqueous layer was washed 5 times with methylene chloride and the combined organic phase was washed 10 times in order to remove residual DMF, dried over $Na_2SO_4$ and the solvent was evaporated under reduced pressure to afford a black oil. The crude product was purified by liquid chromatography using silica gel 60 (230-400 mesh) and a 6:4 hexane:methylene chloride mixture, a 5.8:4:0.2 hexane:methylene chloride:ethyl acetate mixture, a 5.5:4:0.5 hexane:methylene chloride:ethyl acetate mixture, a 5:4:1 hexane:methylene chloride:ethyl acetate mixture, a 4:4:2 hexane:methylene chloride:ethyl acetate mixture and a 3:4:3 hexane:methylene chloride:ethyl acetate mixture, sequentially, as eluents. Pure 4-(5-oxo-2-thioxo-imidazolidin-1-yl)-butyric acid ethyl ester (884 mg, 32% yield) was obtained as a yellowish oil.

$^1$H NMR (CDCl$_3$): δ=7.13 (br s), 4.14 (q, 2H), 4.07 (s, 2H), 3.89 (t, 2H), 2.39 (t, 2H), 2.03 (pent, 2H), 1.26 (t, 2H);

MS (ES$^+$): m/z (%)=270 (MK$^+$, 15), 253 (MNa$^+$, 58), 231 (MH$^+$, 15), 185 (57), 157 (98).

As further depicted in Scheme 40 below, NaH (88 mg of 60% oil dispersion, 53 mg, 2.2 mmol) is added in four portions over 10 minutes under a nitrogen atmosphere to a solution of 4-(5-oxo-2-thioxo-imidazolidin-1-yl)-butyric acid ethyl ester (230 mg, 1 mmol) and ethyl 5-(4-chlorophenyl)-2-formyl-3-furoate (293 mg, 1.05 mmol obtained from Maybridge Ltd.; Cat. No. SP 00067) in anhydrous THF (20 ml). After the ensuing mildly exothermic reaction is completed, the reaction mixture is refluxed for 8-10 hours while monitoring the reaction progress by TLC analysis using an ethyl acetate:hexane mixture as eluent. Thereafter the solvent is removed under reduced pressure, and 6 M HCl (50 ml) is added to the residue while cooling the reaction vessel. Ether (50 ml) is added and the resulting heterogeneous mixture is stirred vigorously at 0° C. for 20 minutes, filtered, washed with ether and water and the solvents are removed under heat at 50° C. overnight to give Compound 48.

Scheme 40

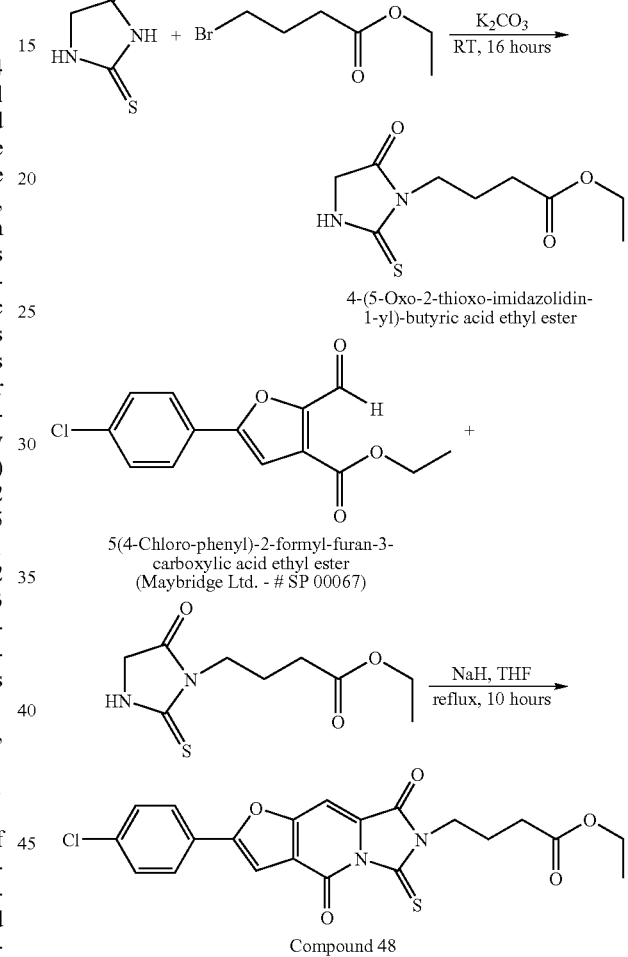

4-(5-Oxo-2-thioxo-imidazolidin-1-yl)-butyric acid ethyl ester

5(4-Chloro-phenyl)-2-formyl-furan-3-carboxylic acid ethyl ester
(Maybridge Ltd. - # SP 00067)

Compound 48

Table 2 below presents the chemical structures of the exemplary compounds which have been prepared and characterized as described hereinabove.

TABLE 2

| Compound No. | Compound Structure |
|---|---|
| 1 | 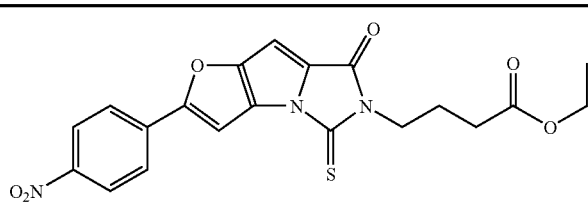 |

TABLE 2-continued
| Compound No. | Compound Structure |
|---|---|
| 2 | 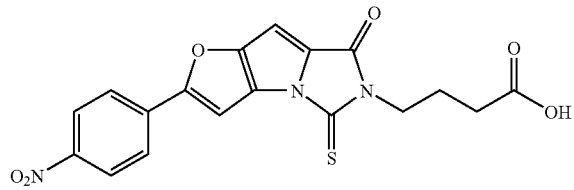 |
| 3 | 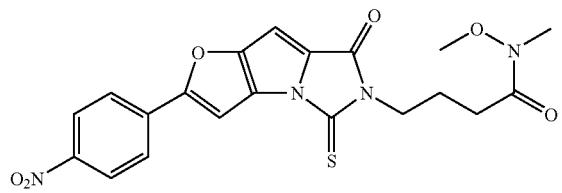 |
| 4 | 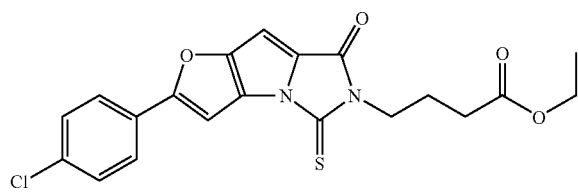 |
| 5 | 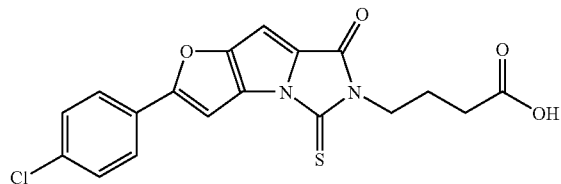 |
| 6 | 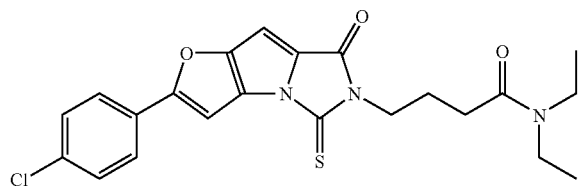 |
| 7 | 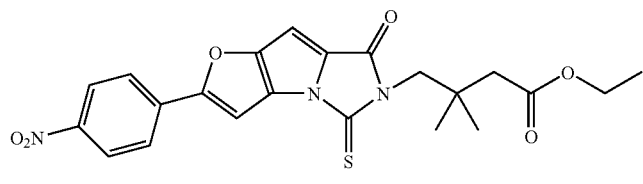 |
| 8 | 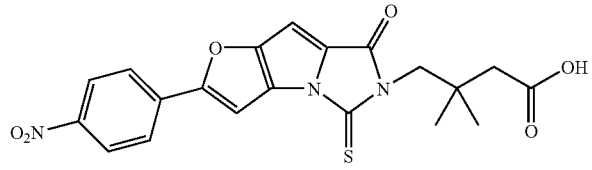 |
| 9 | 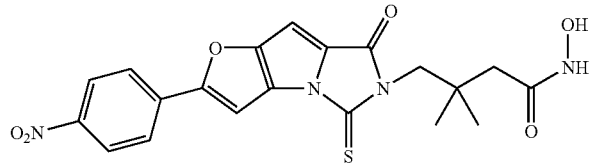 |

TABLE 2-continued
| Compound No. | Compound Structure |
|---|---|
| 10 | 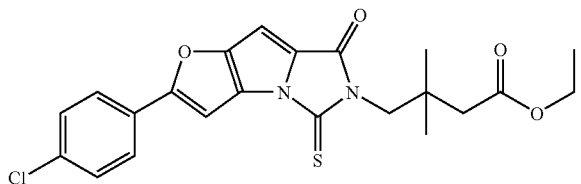 |
| 11 | 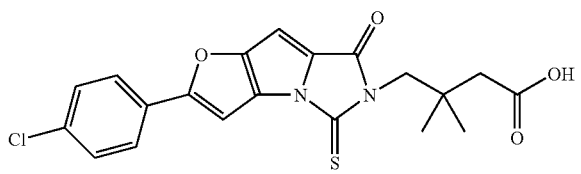 |
| 12 | 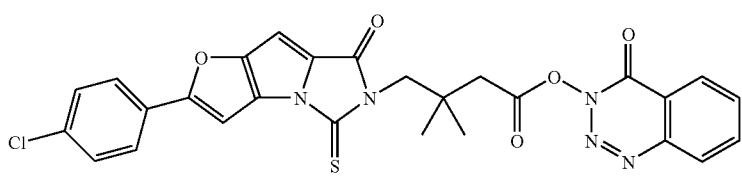 |
| 13 | 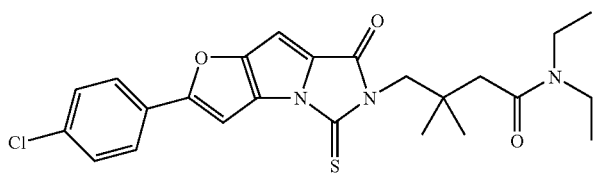 |
| 14 | 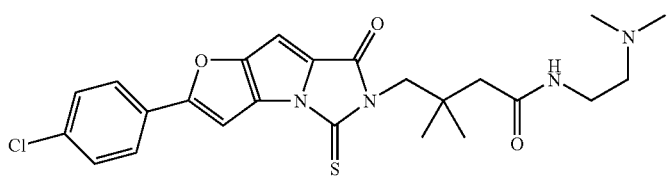 |
| 15 | 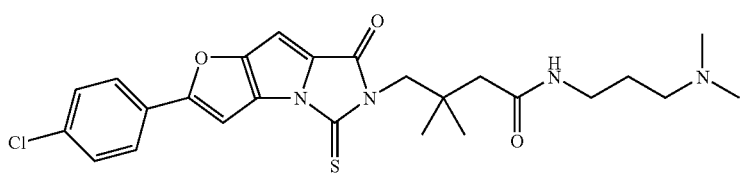 |
| 16 | 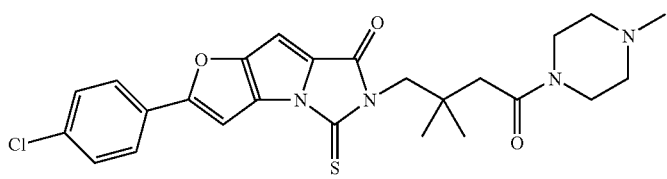 |
| 17 | 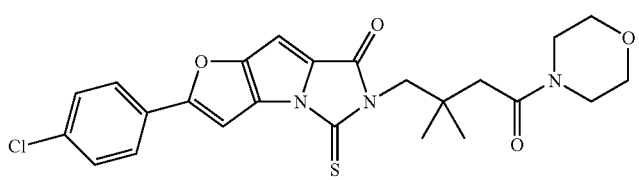 |

TABLE 2-continued
| Compound No. | Compound Structure |
| --- | --- |
| 18 | 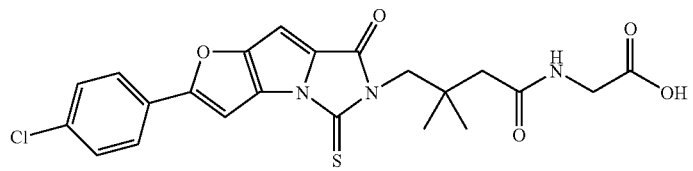 |
| 19 | 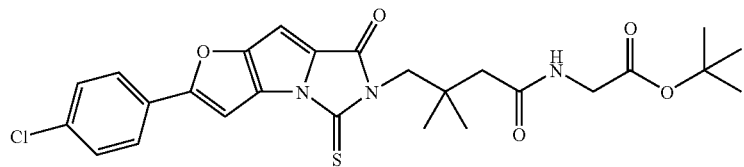 |
| 20 | 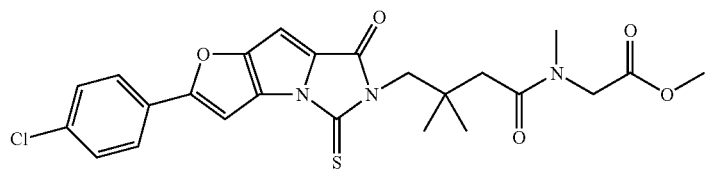 |
| 21 | 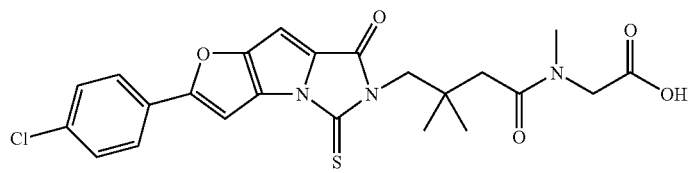 |
| 22 | 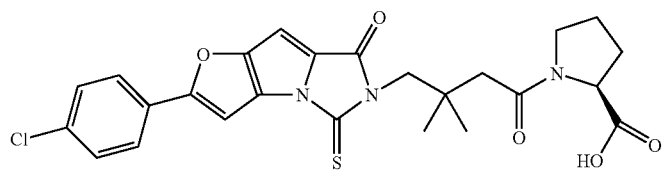 |
| 23 | 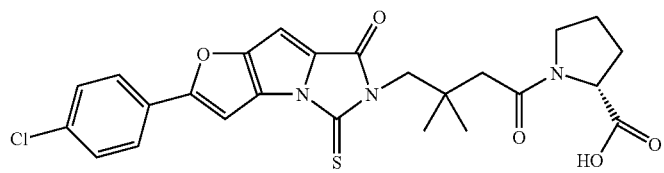 |
| 24 | 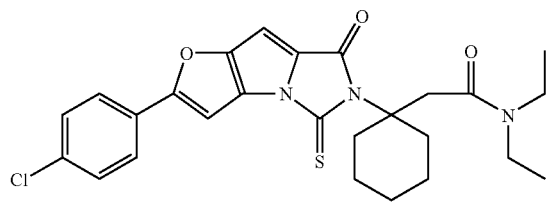 |
| 25 | 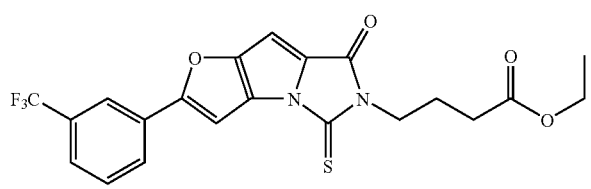 |

TABLE 2-continued
| Compound No. | Compound Structure |
|---|---|
| 26 | 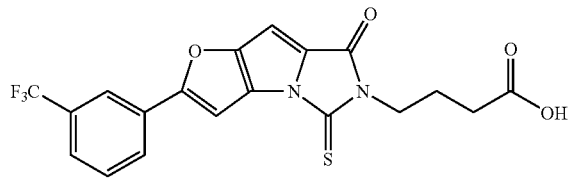 |
| 27 | 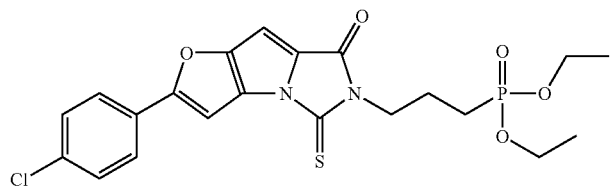 |
| 28 | 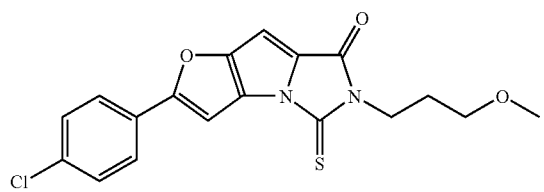 |
| 29 | 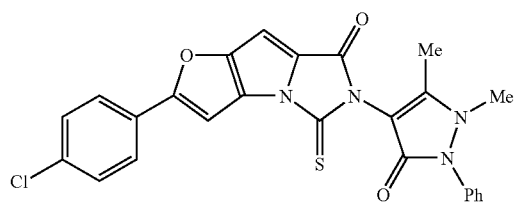 |
| 30 | 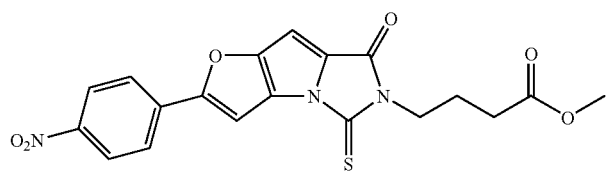 |
| 31 | 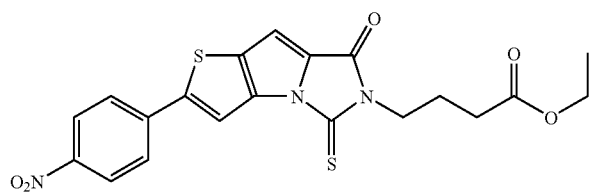 |
| 32 | 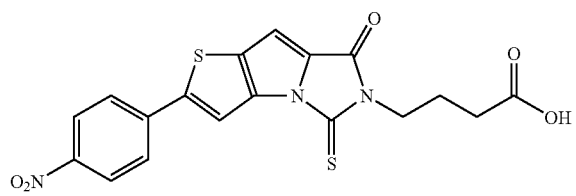 |
| 33 | 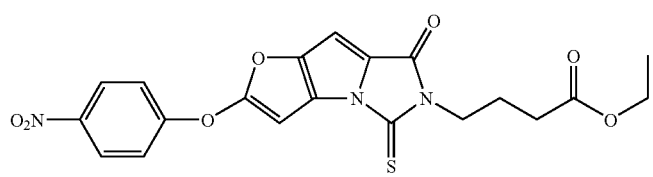 |

TABLE 2-continued

| Compound No. | Compound Structure |
|---|---|
| 38 | 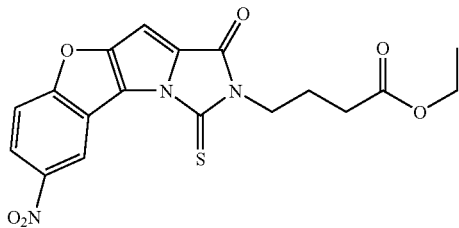 |
| 43 | 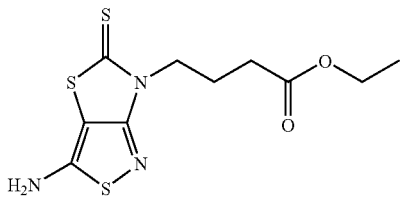 |
| 44 | 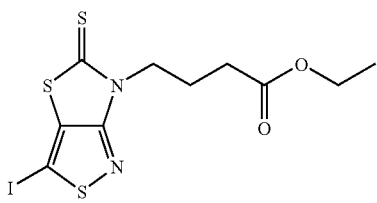 |
| 45 | 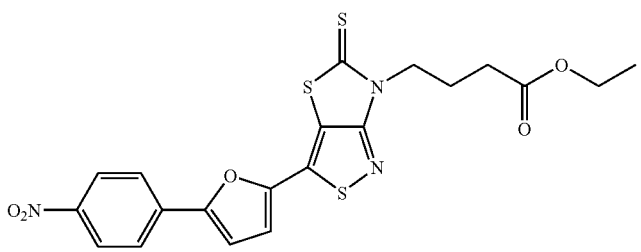 |
| 47 | 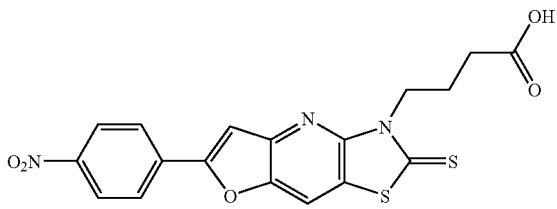 |
| 48 | 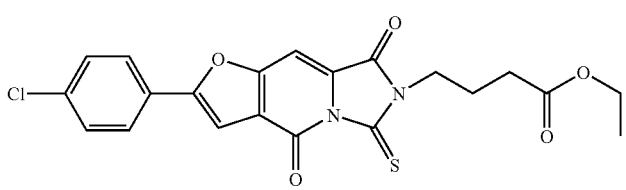 |

Activity Assays

Materials and Experimental Methods

Pro-heparanase (H60) activation in a cell-based assay: Chinese hamster ovary (CHO) cells were grown in complete F12 medium supplemented with 10% fetal calf serum (FCS). The cells were plated onto a 96-well tissue culture plate (Costar cat. No. 3596) at a density of 24,000 cells per well. The plates were incubated for 24 hours in a 37° C. humidified incubator with 5% $CO_2$. Following 24 hours in culture, 200 ng per well of purified recombinant human pro-heparanase (H60, as described in U.S. Pat. No. 6,475,763) was applied to the cells. The plates were further incubated for additional 4 hours. The pro-heparanase was allowed to internalize by the cells and further processed to generate the active 53 kDa heparanase. At the end of the incubation, the cells were lysed by three consecutive cycles of freezing and thawing in a −80° C.

freezer and a 37° C. shaker. Formation of active heparanase was detected by determination of heparanase activity in dimethylmethylene blue (DMB) assay as described in U.S. Pat. No. 6,190,875.

The rigidified compounds described herein were tested for inhibition of pro-heparanase activation in the cell-based assay described above. Compounds exhibiting inhibition of more than 80% of the positive control (containing only 1% DMSO), were considered as active. $IC_{50}$ was calculated from inhibition curves of all active compounds. The assay results are presented in Table 3 below.

Heparanase (H53) assay: The rigidified compounds described herein were tested for inhibition of heparanase activity in the DMB assay described in U.S. Pat. No. 6,190,875. $IC_{50}$ was calculated from inhibition curves of all active compounds. The assay results are presented in Table 3 below.

Enzyme-linked immunosorbent assay (ELISA) for determination of binding of vascular endothelial growth factor (VEGF) to heparin: 96-well microplates were coated for 2 hours. at 23-25° C. with 5 µg/ml heparin-albumin (Rimon Biotech) and blocked with 1% bovine serum albumin (BSA) in phosphate buffer (PBS) with 0.05% Tween and 0.01% thimerosal for 2 hours. VEGF was added to the plates at a concentration of 10 ng/ml and the plates were thereafter incubated for 45 minutes at 23-25° C. The amount of VEGF bound to heparin was detected using anti-VEGF monoclonal antibody (Sigma Cat. No. V4758) at a concentration of 0.26 µg/ml and secondary antibodies Sheep anti-mouse IgG linked to horseradish peroxidase (1:2000) using 3,3',5,5'-tetramethylbenzidine (TMB, Pierce Cat. No. 34021) as a substrate for peroxidase. The plates were read at 450 nm with a reference wavelength of 630 nm using a VERSAmax plate reader. For determination of inhibition of VEGF binding, solutions of 1% of the tested compounds in DMSO were pre-incubated with VEGF prior to application to the plates, for 45 minutes at 23-25° C. Percent inhibition was calculated as compared with a control pre-incubated with a solution of 1% DMSO and the results are presented in Table 3 below.

ELISA for determination of binding of β-FGF to heparin: 96-well microplates were coated for 2 hours at 23-25° C. with 5 µg/ml heparin-albumin (Rimon Biotech) and blocked with 1% BSA in PBS, with 0.05% Tween, and 0.01% thimerosal for 2 hours. β-FGF was added to the plates at a concentration of 10 ng/ml and plates were incubated for 45 minutes at 23-25° C. The amount of β-FGF bound to heparin was detected using anti-FGF monoclonal antibody (Sigma Cat. No. F6162) at a concentration of 2.5 ng/ml and secondary antibodies Sheep anti-mouse IgG linked to horseradish peroxidase (1:3000) TMB (Pierce Cat. No. 34021) was used as a substrate for peroxidase. The plates were read at 450 nm with a reference wavelength of 630 nm using a VERSAmax plate reader. For determination of inhibition of β-FGF binding, compounds in 1% DMSO were pre-incubated with β-FGF prior to application to the plates, for 45 minutes at 23-25° C. Percent inhibition was calculated as compared with the control pre-incubated with 1% DMSO and the results are presented in Table 3 below.

In-vitro assay for inhibition of cell invasion: The ability of the rigidified compounds described herein to inhibit cell invasion was determined quantitatively using BD Biocoat FluoroBlok Invasion System (BD, cat No. FAL354165). MDA-MB231 breast cancer cells, human prostatic cancer PC3 cells and A375 melanoma cells were used for this assay. Cells ($5 \times 10^4$ cells/ml) were pre-incubated with the compounds for 48 hours prior to the assay, at 37° C. and a 5% $CO_2$ atmosphere.

Serial dilutions of each compound starting from a concentration which was previously found to be non-toxic to the cells (using Oxygen Biosensor System, BD), were prepared in DMSO and added to the cells to a final concentration of 1% DMSO. At the end of the pre-incubation, cells at each compound concentration were counted and $2 \times 10^4$ cells/well in basic medium were applied onto the top chamber of the insert of the Invasion system. 750 µl complete medium with 5% fetal calf serum was added to the bottom chambers. The tested compound was applied to the top and bottom chambers. Invasion plates were incubated for 22 hours at 37° C. and a 5% $CO_2$ atmosphere.

At the end of the incubation, medium was aspirated from the upper chambers and the inserts were transferred to a plate containing Calcein AM (Molecular Probes), 4 µg/ml and incubated for 90 minutes at 37° C. and a 5% $CO_2$ atmosphere.

Fluorescence of invaded cells was read in a fluorescence plate reader BMG POLARstar Galaxy, BMG at excitation/emission wavelength of 485/530 nm. The $IC_{50}$ value for inhibition was determined from inhibition curves and the results are presented in Table 3 below.

Experimental Results

Table 3 below summarizes the results obtained in all the assays described hereinabove for representative exemplary compounds according to the present embodiments. The tested compounds were representative compounds of the various subfamilies of rigidified compounds described hereinabove, and were each characterized by certain structural features in terms of the position of the rigidification, the substituents on the rhodanine-like residue and/or the substituents the second aryl residue.

As can be seen in Table 3, these rigidified compounds were found to posses the desired heparanase activity inhibition characteristics.

Specifically, most of the tested compounds were found active in inhibiting pro-heparanase (H60) in cell-based assays and were further proven effective in modulating the binding of vascular endothelial growth factor (VEGF) to heparin, and modulating the binding of β-FGF to heparin.

Rigidified compounds were shown to bind to a heparin-binding domain and interfere with the interaction of heparin or heparan sulfate with its binding sites. Binding of these compounds prevents the change in conformation of the pro-heparanase caused due to interaction with heparan sulfate, and thus indirectly inhibits the proteolytic activity which is required in the maturation process of heparanase.

Some of the rigidified compounds of the present invention that inhibit heparin binding were found to have a dual effect. In addition to their inhibition of pro-heparanase activation they also inhibit heparanase activity. Table 3 presents results of $IC_{50}$ towards inhibition of pro-heparanase activation (H60) and heparanase activity inhibition (H53). From the structure analysis of these inhibitors, it is obvious that only compounds with an acidic group show dual activity (see Compounds 2, 5, 11, 21, 22, 23 and 26).

Rigidified compounds that prevent interaction of the heparin or heparan sulfate with the heparin-binding domain either through interaction with one or more of the heparin-binding domains or by direct binding to glycosaminoglycans, were tested for their ability to inhibit other heparin-binding proteins—fibroblast growth factor (β-FGF) and vascular endothelial growth factor (VEGF).

The results presented in Table 3 below show that rigidified compounds operating through binding to the heparin-binding domain were found to inhibit both β-FGF and to VEGF binding to heparin. Some rigidified compounds, such as Compounds 1, 3, 4, 6, 7, 10, 12, 13, 14, 15, 16, 17, 19, 20, 24, 25, 28, 29 and 31 exhibited sub-micromolar inhibition towards both growth factors. In contrast to the structural requirements of heparanase inhibition, these compounds do not bear an acidic moiety. These inhibitors are highly advantageous, as they do not only inhibit cell migration, invasion and indirect neovascular response through inhibition of heparanase activation, but also directly inhibit the induction of neovascularization in pathological situations through inhibition of VEGF and β-FGF (Vlodavsky I et al; *Cell. Molec. Aspects, Acad. Press. Inc.* pp. 327-343, 1993, Thunberg L et al; *FEBS. Lett.*, 117, 203-206, 1980).

These rigidified compounds can be useful for treatment of other diseases in which heparin-binding proteins have a crucial role such as inflammation (e.g. selectins), cardiovascular diseases (e.g. lipoprotein lipases), central nervous system diseases (e.g. beta-amyloid, prion proteins) and viral diseases (e.g. viral attachment proteins such as gp120).

While conducting each of the protocols described hereinabove for determining the various activities of the rigidified compounds presented herein involved incubation of the tested compounds, with a corresponding substrate, the results presented herein demonstrate that the rigidified compounds presented herein can exert their activity in the absence of light and hence are biologically active in the presence and in the absence of light.

The structure-activity relationship (SAR) of the rigidified compounds presented herein is similar to the SAR of the corresponding non-rigidified rhodanine derivatives taught in U.S. patent application Ser. No. 10/916,598. Thus, for example, compounds wherein $R_1$ (see Formula II) is an unsubstituted or a substituted alkyl-chain, terminally substituted by one or more acidic moieties such as, for example, a carboxylic acid (C-carboxylate), a sulfonic acid (sulfonate), a phosphonic acid (phosphonate) or a boronic acid (borate), and derivatives thereof, such as esters, amides and hydroxyamides thereof were shown to have improved efficacy.

It is further shown that acidic derivatives of a 3,3-dimethyl-butyl are highly efficacious.

TABLE 3

| Compound | IC50 H60 (μM) | IC50 H53 (μM) | IC50 VEGF (μM) | IC50 FGF (μM) | IC50 Invasion MB231/PC3/A3 75 (μM) |
|---|---|---|---|---|---|
| 1 | ND | NI | 0.13 | 0.14 | ND/ND/ND |
| 2 | 1.0 | 9.0 | 1.8 | 1.7 | 2.6/ND/ND |
| 3 | ND | NI | 0.25 | 0.09 | ND/ND/ND |
| 4 | 0.76 | NI | 0.13 | 0.06 | ND/ND/ND |
| 5 | 1.0 | 11.8 | 6.0 | 2.1 | ND/ND/ND |
| 6 | 1.2 | NI | 0.16 | 0.15 | 0.17/ND/ND |
| 7 | 2.6 | ND | 0.1 | 0.05 | ND/ND/ND |
| 8 | 0.78 | ND | ND | ND | ND/ND/ND |
| 9 | 0.17 | ND | ND | ND | ND/ND/ND |
| 10 | 1.5 | NI | 0.17 | 0.20 | ND/ND/ND |
| 11 | 0.27 | 37.0 | 1.2 | 1.8 | 0.75/1.4/ND |
| 12 | 0.35 | ND | 0.26 | 0.16 | ND/ND/ND |
| 13 | 1.4 | NI | 0.55 | 0.22 | ND/ND/ND |
| 14 | 0.12 | ND | 0.26 | 0.47 | ND/ND/ND |
| 15 | 0.16 | NI | 0.18 | 0.44 | ND/ND/ND |
| 16 | 0.09 | NI | 0.29 | 0.20 | 0.035/ND/ND |
| 17 | 0.15 | NI | 0.42 | 0.87 | ND/ND/ND |
| 18 | 0.46 | NI | 2.0 | 1.4 | ND/ND/ND |
| 19 | 0.42 | ND | 0.51 | 0.50 | ND/ND/ND |
| 20 | 0.32 | NI | 0.42 | 0.35 | ND/ND/ND |
| 21 | 1.0 | 66.2 | 7.3 | 6.5 | ND/ND/ND |
| 22 | 0.23 | 34.8 | 2.4 | 2.8 | 0.022/0.05/2.0 |
| 23 | 0.82 | ND | 9.3 | 7.9 | ND/ND/ND |
| 24 | 1.5 | NI | 0.09 | 0.15 | ND/ND/ND |
| 25 | 2.7 | NI | 0.14 | 0.12 | ND/ND/ND |
| 26 | 0.78 | 10.2 | 4.8 | 1.7 | ND/ND/ND |
| 27 | 0.26 | ND | 0.3 | ND | ND/ND/ND |
| 28 | 6.6 | NI | 0.17 | 0.02 | ND/ND/ND |
| 29 | 0.37 | NI | 0.48 | 0.81 | ND/ND/ND |
| 30 | 3.9 | NI | 0.1 | ND | ND/ND/ND |
| 31 | 0.56 | 74.0 | 0.07 | 0.28 | ND/ND/ND |
| 32 | 0.70 | 27.0 | ND | ND | ND/ND/ND |
| 33 | 16 | NI | ND | ND | ND/ND/ND |
| 38 | NI | NI | 22.5 | 11.5 | ND/ND/ND |
| 43 | 25 | NI | NI | NI | ND/ND/ND |
| 44 | 7 | NI | NI | NI | ND/ND/ND |
| 45 | NI | NI | 15 | NI | ND/ND/ND |

NI = no inhibition;
ND = not determined

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A rigidified compound having the general Formula Va:

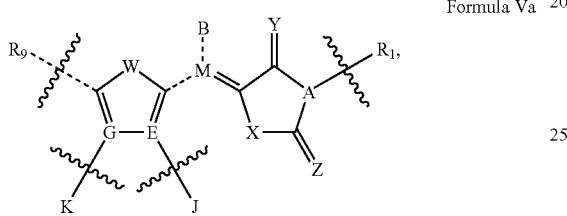

Formula Va wherein:

the compound has a core structure which consists of a rhodanine analog being covalently attached to a first aryl or heteroaryl and of 1-5 linking moieties, at least one of said linking moieties connecting at least two radicals of E and X, such that said core structure has one or zero free-to-rotate bonds, wherein the wavy lines indicate a part of said rhodanine analog and a part of said first aryl or heteroaryl which are included in said core structure, wherein:

the dashed lines indicate either a Z-configuration or an E-configuration of B with respect to Y;

A is N;

X is NRb;

Y, Z and W are each independently O or S;

M is C;

B is selected from the group consisting of hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl;

E and G are each independently CRs;

J and K are absent;

Rb and Rs are each independently hydrogen, a substituted or unsubstituted alkyl, a substituted or unsubstituted cycloalkyl, and a substituted or unsubstituted aryl;

$R_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic, a 3,3-dimethyl-butyramide, a 3,3-dimethyl-butyric acid, a 3,3-dimethyl-butyric ester and a moiety having the general Formula II:

—$(CH_2)n$-CH(Rq)-$Q_1$     Formula II;

and $R_9$ is a substituted or unsubstituted aryl having a general Formula IVa:

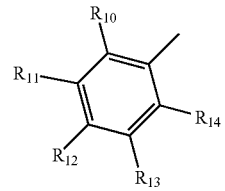

Formula IVa wherein:

each of $R_{10}$-$R_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of $R_{10}$-$R_{14}$ form a five- or six-membered ring;

Rq is selected from the group consisting of hydrogen, alkyl and $Q_2$;

$Q_1$ and $Q_2$ are each independently selected from the group consisting of hydrogen, C-carboxylate, amide, sulfonate, sulfonamide, phosphonate, phosphonamide, borate and silyl; and each of said substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide, wherein when $R_1$ is said substituted alkyl, said substituted alkyl comprises at least one substituent selected from the group consisting of halo, nitro, alkoxy, aryloxy, hydroxy, thiohydroxy, thioalkoxy, thioaryloxy, alkyl, aryl, heteroaryl, trihaloalkyl, C-carboxylate, O-carboxylate, oxo, C-amide, N-amide, S-sulfonamide and N-sulfonamide, with the proviso that the rigidified compound is not 2-(3-methoxy-phenyl)-5-(3-morpholin-4-yl-propyl)-4-thioxo-4,5-dihydro-1-thia-3b,5-diaza-cyclopenta[a]pentalen-6-one or 5-(3-morpholin-4-yl-propyl)-2-(3-nitro-phenyl)-4-thioxo-4,5-dihydro-1-thia-3b,5-diaza-cyclopenta[a]pentalen-6-one.

2. A rigidified compound according to claim 1, wherein at least one of said linking moieties connects radicals of B and Y.

3. A rigidified compound according to claim 1, wherein at least one of said linking moieties connects radicals of W and Y.

4. A rigidified compound according to claim 1, wherein at least one of said linking moieties connects radicals of J and Y.

5. A rigidified compound according to claim 1, wherein at least one of said linking moieties connects radicals of J and B.

6. A rigidified compound according to claim 1, wherein at least one of said linking moieties connects radicals of W and B.

7. A rigidified compound according to claim 1, wherein one of said linking moieties connects radicals of B and Y and one of said linking moieties connects radicals of E and X.

8. A rigidified compound according to claim 1, wherein $R_1$ is said moiety having the general Formula II.

9. A rigidified compound according to claim 1, wherein $R_1$ is a substituted or unsubstituted heteroaryl.

10. A rigidified compound according to claim 1, wherein $R_1$ is a substituted or unsubstituted aryl.

11. A rigidified compound according to claim 1, being selected from the group consisting of:
ethyl 4-[2-(4-nitro-phenyl)-6-oxo-4-thioxo-6H-1-oxa-3b,5-diaza-cyclopenta[a]pentalen-5-yl]-butyric acid ethyl ester (Compound 1);
4-[2-(4-nitro-phenyl)-6-oxo-4-thioxo-6H-1-oxa-3b,5-diaza-cyclopenta[a]pentalen-5-yl]-butyric acid (Compound 2);
N-methoxy-N-methyl-4-[2-(4-nitro-phenyl)-6-oxo-4-thioxo-6H-1-oxa-3b,5-diaza-cyclopenta[a]pentalen-5-yl]-butyramide (Compound 3);
ethyl 4-[2-(4-chloro-phenyl)-6-oxo-4-thioxo-6H-1-oxa-3b,5-diaza-cyclopenta[a]pentalen-5-yl]-butyric acid ethyl ester (Compound 4);
4-[2-(4-chloro-phenyl)-6-oxo-4-thioxo-6H-1-oxa-3b,5-diaza-cyclopenta[a]pentalen-5-yl]-butyric acid (Compound 5);
4-[2-(4-chloro-phenyl)-6-oxo-4-thioxo-6H-1-oxa-3b,5-diaza-cyclopenta[a]pentalen-5-yl]-N,N-diethyl-butyramide (Compound 6);
3,3-dimethyl-4-[2-(4-nitro-phenyl)-6-oxo-4-thioxo-6H-1-oxa-3b,5-diaza-cyclopenta[a]pentalen-5-yl]-butyric acid ethyl ester (Compound 7);
3,3-Dimethyl-4-[2-(4-nitro-phenyl)-6-oxo-4-thioxo-6H-1-oxa-3b,5-diaza-cyclopenta[a]pentalen-5-yl]-butyric acid (Compound 8);
N-hydroxy-3,3-dimethyl-4-[2-(4-nitro-phenyl)-6-oxo-4-thioxo-6H-1-oxa-3b,5-diaza-cyclopenta[a]pentalen-5-yl]-butyramide (Compound 9);
4-[2-(4-Chloro-phenyl)-6-oxo-4-thioxo-6H-1-oxa-3b,5-diaza-cyclopenta[a]pentalen-5-yl]-3,3-dimethyl-butyric acid ethyl ester (Compound 10);
4-[2-(4-chloro-phenyl)-6-oxo-4-thioxo-6H-1-oxa-3b,5-diaza-cyclopenta[a]pentalen-5-yl]-3,3-dimethyl-butyric acid (Compound 11);
4-[2-(4-Chloro-phenyl)-6-oxo-4-thioxo-6H-1-oxa-3b,5-diaza-cyclopenta[a]pentalen-5-yl]-3,3-dimethyl-butyric acid 4-oxo-4H-benzo[d][1,2,3]triazin-3-yl ester (Compound 12);
4-[2-(4-Chloro-phenyl)-6-oxo-4-thioxo-6H-1-oxa-3b,5-diaza-cyclopenta[a]pentalen-5-yl]-N,N-diethyl-3,3-dimethyl-butyramide (Compound 13);
4-[2-(4-Chloro-phenyl)-6-oxo-4-thioxo-6H-1-oxa-3b,5-diaza-cyclopenta[a]pentalen-5-yl]-N-(2-dimethylamino-ethyl)-3,3-dimethyl-butyramide (Compound 14);
4-[2-(4-Chloro-phenyl)-6-oxo-4-thioxo-6H-1-oxa-3b,5-diaza-cyclopenta[a]pentalen-5-yl]-N-(3-dimethylamino-propyl)-3,3-dimethyl-butyramide (Compound 15);
2-(4-Chloro-phenyl)-5-[2,2-dimethyl-4-(4-methyl-piperazin-1-yl)-4-oxo-butyl]-4-thioxo-4,5-dihydro-1-oxa-3b,5-diaza-cyclopenta[a]pentalen-6-one (Compound 16);
2-(4-Chloro-phenyl)-5-(2,2-dimethyl-4-morpholin-4-yl-4-oxo-butyl)-4-thioxo-4,5-dihydro-1-oxa-3b,5-diaza-cyclopenta[a]pentalen-6-one (Compound 17);
{4-[2-(4-Chloro-phenyl)-6-oxo-4-thioxo-6H-1-oxa-3b,5-diaza-cyclopenta[a]pentalen-5-yl]-3,3-dimethyl-butyrylamino}-acetic acid (Compound 18);
{4-[2-(4-Chloro-phenyl)-6-oxo-4-thioxo-6H-1-oxa-3b,5-diaza-cyclopenta[a]pentalen-5-yl]-3,3-dimethyl-butyrylamino}-acetic acid tert-butyl ester (Compound 19);
({4-[2-(4-Chloro-phenyl)-6-oxo-4-thioxo-6H-1-oxa-3b,5-diaza-cyclopenta[a]pentalen-5-yl]-3,3-dimethyl-butyryl}-methyl-amino)-acetic acid methyl ester (Compound 20);
({4-[2-(4-Chloro-phenyl)-6-oxo-4-thioxo-6H-1-oxa-3b,5-diaza-cyclopenta[a]pentalen-5-yl]-3,3-dimethyl-butyryl}-methyl-amino)-acetic acid (Compound 21);
1-{4-[2-(4-Chloro-phenyl)-6-oxo-4-thioxo-6H-1-oxa-3b,5-diaza-cyclopenta[a]pentalen-5-yl]-3,3-dimethyl-butyryl}-pyrrolidine-2-carboxylic acid (Compound 22);
1-{4-[2-(4-Chloro-phenyl)-6-oxo-4-thioxo-6H-1-oxa-3b,5-diaza-cyclopenta[a]pentalen-5-yl]-3,3-dimethyl-butyryl}-pyrrolidine-2-carboxylic acid (Compound 23);
2-{1-[2-(4-Chloro-phenyl)-6-oxo-4-thioxo-6H-1-oxa-3b,5-diaza-cyclopenta[a]pentalen-5-ylmethyl]-cyclohexyl}-N,N-diethyl-acetamide (Compound 24);
4-[6-oxo-4-thioxo-2-(3-trifluoromethyl-phenyl)-6H-1-oxa-3b,5-diaza-cyclopenta[a]pentalen-5-yl]-butyric acid ethyl ester (Compound 25);
ethyl 4-[6-oxo-4-thioxo-2-(3-trifluoromethyl-phenyl)-6H-1-oxa-3b,5-diaza-cyclopenta[a]pentalen-5-yl]-butyric acid (Compound 26);
{3-[2-(4-chloro-phenyl)-6-oxo-4-thioxo-6H-1-oxa-3b,5-diaza-cyclopenta[a]pentalen-5-yl]-propyl}-phosphonic acid diethyl ester (Compound 27);
2-(4-Chloro-phenyl)-5-(3-methoxy-propyl)-4-thioxo-4,5-dihydro-1-oxa-3b,5-diaza-cyclopenta[a]pentalen-6-one (Compound 28);
2-(4-chloro-phenyl)-5-(1,5-dimethyl-3-oxo-2-phenyl-2,3-dihydro-1H-pyrazol-4-yl)-4-thioxo-4,5-dihydro-1-oxa-3b,5-diaza-cyclopenta[a]pentalen-6-one (Compound 29);
4-[2-(4-Nitro-phenyl)-4,6-dioxo-6H-1-oxa-3b,5-diaza-cyclopenta[a]pentalen-5-yl]-butyric acid ethyl ester (Compound 30);
4-[2-(4-nitro-phenyl)-6-oxo-4-thioxo-6H-1-thia-3b,5-diaza-cyclopenta[a]pentalen-5-yl]-butyric acid ethyl ester (Compound 31);
4-[2-(4-Nitro-phenyl)-6-oxo-4-thioxo-6H-1-thia-3b,5-diaza-cyclopenta[a]pentalen-5-yl]-butyric acid (Compound 32);
5-(1,1-Dioxo-tetrahydro-thiophen-3-yl)-2-(4-nitro-phenyl)-4-thioxo-4,5-dihydro-1-oxa-3b,5-diaza-cyclopenta[a]pentalen-6-one (Compound 34);
4-[2-(4-Nitro-phenyl)-6-oxo-4-thioxo-6H-1-oxa-3b,5-diaza-cyclopenta[a]pentalen-5-yl]-butyronitrile (Compound 35); and
2-(4-Nitro-phenyl)-5-[3-(2H-tetrazol-5-yl)-propyl]-4-thioxo-4,5-dihydro-1-oxa-3b,5-diaza-cyclopenta[a]pentalen-6-one (Compound 36).

12. A pharmaceutical composition comprising, as an active ingredient, a rigidified compound according to claim 1 and a pharmaceutically acceptable carrier.

13. A pharmaceutical composition according to claim 12, being packaged in a packaging material and identified in print, in or on said packaging material, for use in inhibiting an activity of heparanase, inhibiting heparanase activation and/or inhibiting heparin binding protein.

14. A method of treating pancreatic cancer in a subject in need thereof, the method comprising administering to the subject a therapeutically effective amount of a rigidified compound having the general Formula Va:

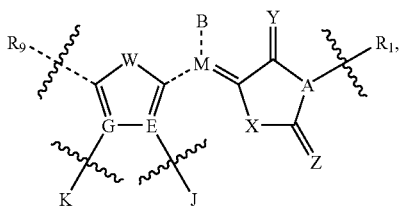

Formula Va wherein:
the compound has a core structure which consists of a rhodanine analog being covalently attached to a first aryl or heteroaryl and of 1-5 linking moieties, at least one of said linking moieties connecting at least two radicals of E and X, such that said core structure has one or zero free-to-rotate bonds,
wherein the wavy lines indicate a part of said rhodanine analog and a part of said first aryl or heteroaryl which are included in said core structure;
wherein:
the dashed lines indicate either a Z-configuration or an E-configuration of B with respect to Y;
A is N;
X is NRb;
Y, Z and W are each independently O or S;
M is C;
B is selected from the group consisting of hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl;
E and G are each independently CRs;
J and K are absent;
Rb and Rs are each independently hydrogen, a substituted or unsubstituted alkyl, a substituted or unsubstituted cycloalkyl, and a substituted or unsubstituted aryl;
$R_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic, a 3,3-dimethyl-butyramide, a 3,3-dimethyl-butyric acid, a 3,3-dimethyl-butyric ester and a moiety having the general Formula II:

—(CH$_2$)$n$-CH(Rq)-Q$_1$  Formula II;

and
$R_9$ is a substituted or unsubstituted aryl having a general Formula IVa:

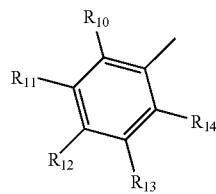

Formula IVa wherein:
each of $R_{10}$-$R_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of $R_{10}$-$R_{14}$ form a five- or six-membered ring;
Rq is selected from the group consisting of hydrogen, alkyl and Q$_2$;
Q$_1$ and Q$_2$ are each independently selected from the group consisting of hydrogen, C-carboxylate, amide, sulfonate, sulfonamide, phosphonate, phosphonamide, borate and silyl; and
each of said substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide.

15. A method of inhibiting heparanase activation, the method comprising contacting an inactive heparanase with a rigidified compound having the general Formula Va:

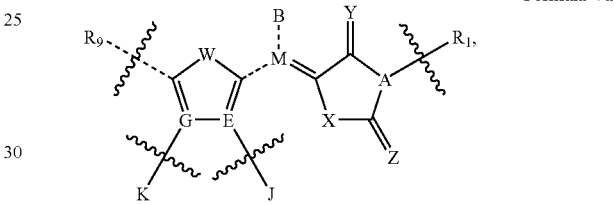

Formula Va wherein:
the compound has a core structure which consists of a rhodanine analog being covalently attached to a first aryl or heteroaryl and of 1-5 linking moieties, at least one of said linking moieties connecting at least two radicals of E and X, such that said core structure has one or zero free-to-rotate bonds,
wherein the wavy lines indicate a part of said rhodanine analog and a part of said first aryl or heteroaryl which are included in said core structure;
wherein:
the dashed lines indicate either a Z-configuration or an E-configuration of B with respect to Y;
A is N;
X is NRb;
Y, Z and W are each independently O or S;
M is C;
B is selected from the group consisting of hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl;
E and G are each independently CRs;
J and K are absent;
Rb and Rs are each independently hydrogen, a substituted or unsubstituted alkyl, a substituted or unsubstituted cycloalkyl, and a substituted or unsubstituted aryl;
$R_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic, a 3,3-dimethyl-butyramide, a 3,3-dimethyl-butyric acid, a 3,3-dimethyl-butyric ester and a moiety having the general Formula II:

—(CH$_2$)n-CH(Rq)-Q$_1$  Formula II;

and

R$_9$ is a substituted or unsubstituted aryl having a general Formula IVa:

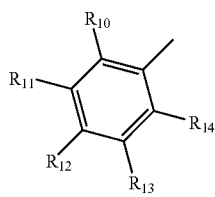

Formula IVa wherein:
each of R$_{10}$-R$_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of R$_{10}$-R$_{14}$ form a five- or six-membered ring;

Rq is selected from the group consisting of hydrogen, alkyl and Q$_2$;

Q$_1$ and Q$_2$ are each independently selected from the group consisting of hydrogen, C-carboxylate, amide, sulfonate, sulfonamide, phosphonate, phosphonamide, borate and silyl; and each of said substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide.

16. A method of inhibiting heparanase activity, the method comprising contacting the heparanase with a rigidified compound having the general Formula Va:

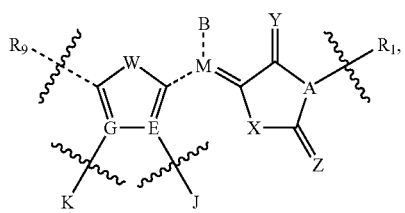

Formula Va wherein:
the compound has a core structure which consists of a rhodanine analog being covalently attached to a first aryl or heteroaryl and of 1-5 linking moieties, at least one of said linking moieties connecting at least two radicals of E and X, such that said core structure has one or zero free-to-rotate bonds, wherein the wavy lines indicate a part of said rhodanine analog and a part of said first aryl or heteroaryl which are included in said core structure;

wherein:
the dashed lines indicate either a Z-configuration or an E-configuration of B with respect to Y;
A is N;
X is NRb;
Y, Z and W are each independently O or S;
M is C;
B is selected from the group consisting of hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl;
E and G are each independently CRs;
J and K are absent;
Rb and Rs are each independently hydrogen, a substituted or unsubstituted alkyl, a substituted or unsubstituted cycloalkyl, and a substituted or unsubstituted aryl;
R$_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic, a 3,3-dimethyl-butyramide, a 3,3-dimethyl-butyric acid, a 3,3-dimethyl-butyric ester and a moiety having the general Formula II:

—(CH$_2$)n-CH(Rq)-Q$_1$  Formula II;

and

R$_9$ is a substituted or unsubstituted aryl having a general Formula IVa:

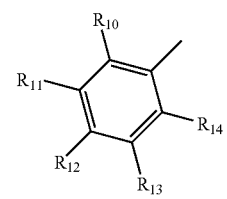

Formula IVa wherein:
each of R$_{10}$-R$_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of R$_{10}$-R$_{14}$ form a five- or six-membered ring;

Rq is selected from the group consisting of hydrogen, alkyl and Q$_2$;

Q$_1$ and Q$_2$ are each independently selected from the group consisting of hydrogen, C-carboxylate, amide, sulfonate, sulfonamide, phosphonate, phosphonamide, borate and silyl; and each of said substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide.

17. A method of inhibiting heparin binding protein, the method comprising contacting the heparin binding protein with a rigidified compound having the general Formula Va:

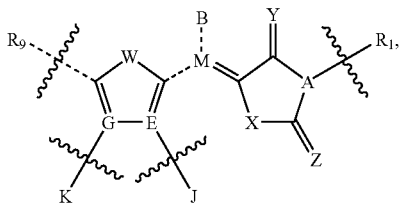

Formula Va wherein:
the compound has a core structure which consists of a rhodanine analog being covalently attached to a first aryl or heteroaryl and of 1-5 linking moieties, at least one of said linking moieties connecting at least two radicals of E and X, such that said core structure has one or zero free-to-rotate bonds,
wherein the wavy lines indicate a part of said rhodanine analog and a part of said first aryl or heteroaryl which are included in said core structure;
wherein:
the dashed lines indicate either a Z-configuration or an E-configuration of B with respect to Y;
A is N;
X is NRb;
Y, Z and W are each independently O or S;
M is C;
B is selected from the group consisting of hydroxy, thiohydroxy, alkoxy, thioalkoxy, amine, hydrogen, a substituted or unsubstituted alkyl, a substituted or unsubstituted cycloalkyl, a substituted or unsubstituted aryl and a substituted or unsubstituted heteroaryl;
E and G are each independently CRs;
J and K are absent;
Rb and Rs are each independently hydrogen, a substituted or unsubstituted alkyl, a substituted or unsubstituted cycloalkyl, and a substituted or unsubstituted aryl;
$R_1$ is selected from the group consisting of hydrogen, a substituted or unsubstituted alkyl, a substituted or unsubstituted cycloalkyl, a substituted or unsubstituted alkenyl, a substituted or unsubstituted allyl, a substituted or unsubstituted aryl, a substituted or unsubstituted heteroaryl, a substituted or unsubstituted heteroalicyclic, a 3,3-dimethyl-butyramide, a 3,3-dimethyl-butyric acid, a 3,3-dimethyl-butyric ester and a moiety having the general Formula II:

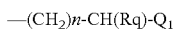
—$(CH_2)n$-CH(Rq)-$Q_1$    Formula II;

and
$R_9$ is a substituted or unsubstituted aryl having a general Formula IVa:

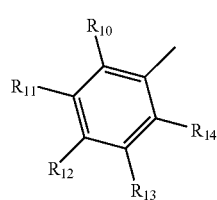

Formula IVa wherein:
each of $R_{10}$-$R_{14}$ is independently selected from the group consisting of hydrogen, alkyl, hydroxy, thiohydroxy, alkoxy, thioalkoxy, halo, nitro, trihaloalkyl, C-carboxylate, O-carboxylate, C-amide, N-amide, S-sulfonamide and N-sulfonamide, or, alternatively, at least two of $R_{10}$-$R_{14}$ form a five- or six-membered ring;
Rq is selected from the group consisting of hydrogen, alkyl and $Q_2$;
$Q_1$ and $Q_2$ are each independently selected from the group consisting of hydrogen, C-carboxylate, amide, sulfonate, sulfonamide, phosphonate, phosphonamide, borate and silyl; and
each of said substituted alkyl, substituted cycloalkyl, substituted alkenyl, substituted allyl, substituted aryl and substituted heteroaryl independently comprises at least one substituent selected from the group consisting of halo, nitro, alkoxy, aryloxy, hydroxy, thiohydroxy, thioalkoxy, thioaryloxy, alkyl, aryl, heteroaryl, heteroalicyclic, trihaloalkyl, C-carboxylate, O-carboxylate, oxo, C-amide, N-amide, S-sulfonamide and N-sulfonamide.

18. A pharmaceutical composition according to claim 12, being packaged in a packaging material and identified in print, in or on said packaging material, for use in the treatment of pancreatic cancer.

19. A rigidified compound according to claim 1, wherein:
Y is O; and
Z is S.

20. A rigidified compound according to claim 19, wherein B and Rs are each hydrogen.

21. A rigidified compound according to claim 20, wherein $R_{10}$, $R_{11}$, $R_{13}$ and $R_{14}$ are each hydrogen.

22. A rigidified compound according to claim 21, wherein $R_{12}$ is selected from the group consisting of nitro, halo and trihaloalkyl.

23. A rigidified compound according to claim 20, wherein $R_1$ has said general Formula II, and wherein n is 2, and Rq is hydrogen.

24. A rigidified compound according to claim 23, wherein $Q_1$ is selected from the group consisting of C-carboxylate and amide.

25. A rigidified compound according to claim 20, wherein $R_1$ is selected from the group consisting of 3,3-dimethyl-butryamide, 3,3-dimethylbutyric acid and 3,3-dimethylbutyric ester.

26. A rigidified compound according to claim 20, wherein $R_1$ is selected from the group consisting of butyric acid, butyric acid ethyl ester, N-methoxy-N-methyl-butyramide, N,N-diethyl-butyramide, 3,3-dimethyl-butyric acid, 3,3-dimethyl-butyric acid ethyl ester, N-hydroxy-3,3-dimethyl-butyramide, 3,3-dimethyl-butyric acid 4-oxo-4H-benzo[d][1,2,3]triazin-3-yl ester, N,N-diethyl-3,3-dimethyl-butyramide, N-(2-dimethylamino-ethyl)-3,3-dimethyl-butyramide, N-(3-dimethylamino-propyl)-3,3-dimethyl-butyramide, 3,3-dimethyl-1-(4-methyl-piperazin-1-yl)-butan-1-one, 3,3-dimethyl-1-morpholin-4-yl-butan-1-one, (3,3-dimethyl-butyrylamino)-acetic acid, (3,3-dimethyl-butyrylamino)-acetic acid tert-butyl ester, [(3,3-dimethyl-butyryl)-methyl-amino]-acetic acid, [(3,3-dimethyl-butyryl)-methyl-amino]-acetic acid methyl ester, 1-(3,3-dimethyl-butyryl)-pyrrolidine-2-carboxylic acid, N,N-diethyl-2-(1-methyl-cyclohexyl)-acetamide, propyl-phosphonic acid diethyl ester and 1-methoxy-propane.

27. A rigidified compound according to claim 1, wherein $R_1$ is selected from the group consisting of butyric acid, butyric acid ethyl ester, N-methoxy-N-methyl-butyramide, N,N-diethyl-butyramide, 3,3-dimethyl-butyric acid, 3,3- dimethyl-butyric acid ethyl ester, N-hydroxy-3,3-dimethyl-butyramide, 3,3-dimethyl-butyric acid 4-oxo-4H-benzo[d][1,2,3]triazin-3-yl ester, N,N-diethyl-3,3-dimethyl-butyramide, N-(2-dimethylamino-ethyl)-3,3-dimethyl-butyramide, N-(3-dimethylamino-propyl)-3,3-dimethyl-butyramide, 3,3-dimethyl-1-(4-methyl-piperazin-1-yl)-butan-1-one, 3,3-dimethyl-1-morpholin-4-yl-butan-1-one, (3,3-dimethyl-butyrylamino)-acetic acid, (3,3-dimethyl-butyrylamino)-acetic acid tert-butyl ester, [(3,3-dimethyl-butyryl)-methyl-amino]-acetic acid, [(3,3-dimethyl-butyryl)-methyl-amino]-acetic acid methyl ester, 1-(3,3-dimethyl-butyryl)-pyrrolidine-2-carboxylic acid, N,N-diethyl-2-(1-methyl-cyclohexyl)-acetamide, propyl-phosphonic acid diethyl ester and 1-methoxy-propane.

* * * * *